United States Patent [19]

Lin

[11] Patent Number: 5,618,698
[45] Date of Patent: *Apr. 8, 1997

[54] PRODUCTION OF ERYTHROPOIETIN

[75] Inventor: Fu-Kuen Lin, Thousand Oaks, Calif.

[73] Assignee: Kirin-Amgen, Inc., Thousand Oaks, Calif.

[*] Notice: The portion of the term of this patent subsequent to Aug. 15, 2012, has been disclaimed.

[21] Appl. No.: 468,381

[22] Filed: Jun. 6, 1995

Related U.S. Application Data

[63] Continuation of Ser. No. 113,179, Oct. 23, 1987, Pat. No. 5,441,868, which is a continuation of Ser. No. 675,298, Nov. 30, 1984, Pat. No. 4,703,008, which is a continuation-in-part of Ser. No. 655,841, Sep. 28, 1984, which is a continuation-in-part of Ser. No. 582,185, Feb. 21, 1984, abandoned, which is a continuation-in-part of Ser. No. 561,024, Dec. 13, 1983.

[51] Int. Cl.⁶ .......................... C12P 71/02; C12N 15/27
[52] U.S. Cl. .......................... 435/69.4; 435/69.6; 435/325; 536/23.51
[58] Field of Search .......................... 435/240.2, 177.3, 435/320.1, 69.4, 240.1, 69.1, 69.6; 536/23.5, 23.51

[56] References Cited

U.S. PATENT DOCUMENTS

| | | | |
|---|---|---|---|
| 3,033,753 | 5/1962 | White et al. | 536/345 |
| 3,865,801 | 2/1975 | Chiba et al. | 536/357 |
| 4,237,224 | 12/1980 | Cohen et al. | 435/61.1 |
| 4,254,095 | 3/1981 | Fisher et al. | 436/513 |
| 4,264,731 | 4/1981 | Shine | 435/91.41 |
| 4,273,875 | 6/1981 | Manis | 435/91.4 |
| 4,293,652 | 10/1981 | Cohen | 435/172.3 |
| 4,303,650 | 12/1981 | Takezawa et al. | 603/391 |
| 4,338,397 | 7/1982 | Gilbert et al. | 435/69.1 |
| 4,358,535 | 11/1982 | Falkow et al. | 435/5 |
| 4,377,513 | 3/1983 | Sugimoto et al. | 527/395 |
| 4,394,443 | 7/1983 | Weissman et al. | 435/6 |
| 4,397,840 | 8/1983 | Takezawa et al. | 361/399 |
| 4,399,216 | 8/1983 | Axel et al. | 435/6 |
| 4,411,994 | 10/1983 | Gilbert et al. | 435/69.7 |
| 4,442,205 | 4/1984 | Hamer et al. | 435/69.3 |
| 4,465,624 | 8/1984 | Chiba et al. | 530/375 |
| 4,468,464 | 8/1984 | Cohen et al. | 435/320.1 |
| 4,503,151 | 3/1985 | Paddock | 435/69.1 |
| 4,558,005 | 12/1985 | Goldwasser et al. | 435/7.92 |
| 4,558,006 | 12/1985 | Egrie | 435/7.94 |
| 4,568,488 | 2/1986 | Lee-Huang | 562/397 |
| 4,667,016 | 5/1987 | Lai et al. | 530/397 |
| 4,677,195 | 6/1987 | Hewick et al. | 530/397 |
| 4,695,542 | 9/1987 | Yokata et al. | 435/69.4 |
| 4,703,008 | 10/1987 | Lin | 435/240.2 |
| 4,710,473 | 12/1987 | Morris | 435/320.1 |
| 4,757,006 | 7/1988 | Toole et al. | 435/61.6 |

FOREIGN PATENT DOCUMENTS

| | | |
|---|---|---|
| 0070685 | 1/1983 | European Pat. Off. |
| 0070687 | 1/1983 | European Pat. Off. |
| 0077670 | 4/1983 | European Pat. Off. |
| 0093619 | 11/1983 | European Pat. Off. |
| 0116446 | 8/1984 | European Pat. Off. |
| 0117058 | 8/1984 | European Pat. Off. |
| 0117059 | 8/1984 | European Pat. Off. |
| 0117060 | 8/1984 | European Pat. Off. |
| 0123294 | 10/1984 | European Pat. Off. |
| 0136490 | 4/1985 | European Pat. Off. |
| 3316297A1 | 11/1983 | Germany |
| 3348298C2 | 11/1983 | Germany |
| 2085887 | 5/1982 | United Kingdom |
| 83/04053 | 11/1983 | WIPO |
| 85/01961 | 5/1985 | WIPO |
| 85/03079 | 7/1985 | WIPO |
| 85/04419 | 10/1985 | WIPO |
| 86/03520 | 6/1986 | WIPO |

OTHER PUBLICATIONS

Abraham et al., "Nucleotide Sequence of a Bovine Clone Encoding the Angiogenic Protein, Basic Fibroblast Growth Factor," *Science*, 233, 545–548 (Aug. 1, 1986).

Adamson, "The Polycythemias: Diagnosis and Treatment," *Hosp. Practice*, 18(12), 49–57 (Dec. 1983).

Aebi et al., "Sequence Requirements for Splicing of Higher Eukaryotic Nuclear Pre–mRNA," *Cell*, 47, 555–565 (Nov. 21, 1986).

Agarwal et al., "A General Method for Detection and Characterization of an mRNA using an Oligonucleotide Probe," *J. Biol. Chem.*, 256, 1023–1028 (Jan. 25, 1981).

Anderson et al., "Isolation of a genomic clone for bovine pancreatic trypsin inhibitor by using a unique–sequence synthetic DNA probe," *P.N.A.S. (USA)*, 80, 6838–6842 (Nov. 1983).

Antonsson et al., "Posttranslational Modifications of Fibromodulin," *J. Biol. Chem.*, 266(25), 16859–16861 (1991).

Baciu et al., "Erythropoietin Interaction with the Mature Red Cell Membrane," *Ann. N.Y. Acad. Sci.*, 414, 66–72 (1983).

(List continued on next page.)

*Primary Examiner*—James Martinell
*Attorney, Agent, or Firm*—Marshall, O'Toole, Gerstein, Murray & Borun

[57] ABSTRACT

Disclosed are novel polypeptides possessing part or all of the primary structural conformation and one or more of the biological properties of mammalian erythropoietin ("EPO") which are characterized in preferred forms by being the product of procaryotic or eucaryotic host expression of an exogenous DNA sequence. Illustratively, genomic DNA, cDNA and manufactured DNA sequences coding for part or all of the sequence of amino acid residues of EPO or for analogs thereof are incorporated into autonomously replicating plasmid or viral vectors employed to transform or transfect suitable procaryotic or eucaryotic host cells such as bacteria, yeast or vertebrate cells in culture. Upon isolation from culture media or cellular lysates or fragments, products of expression of the DNA sequences display, e.g., the immunological properties and in vitro and in vivo biological activities of EPO of human or monkey species origins. Disclosed also are chemically synthesized polypeptides sharing the biochemical and immunological properties of EPO. Also disclosed are improved methods for the detection of specific single stranded polynucleotides in a heterologous cellular or viral sample prepared from, e.g., DNA present in a plasmid or viral-borne cDNA or genomic DNA "library".

9 Claims, 27 Drawing Sheets

OTHER PUBLICATIONS

Baron et al., "Antibodies against the Chemically Synthesized Genome-Linked Protein of Poliovirus React with Native Virus-Specific Proteins," *Cell*, 28, 395–404 (Feb. 1982).

Beaucage et al., "Deoxynucleoside Phosphoramidites—A new Class of Key Intermediates for Deoxypolynucleotide Synthesis," *Tetrahedron Letters*, 22(20), 1859–1862 (1981).

Benedum et al., "The primary structure of bovine chromogranin A: a representative of a class of acidic secretory proteins common to a variety of peptidergic cells," *EMBO J.* (7), 1495–1502 (1986).

Bennetzen et al., "Codon Selection in Yeast," *J. Biol. Chem.*, 257(6), 3026–3031 (Mar. 25, 1982).

Bentley et al., "Human immunoglobulin variable region genes-DNA sequences of two $V_k$ genes and a pseudogene," *Nature* 288, 730–733 (Dec. 1980).

Benton et al., "Screening λgt Recombinant Clones by Hybridization to single Plaques in situ," *Science* 196, 180–182 (Apr. 8, 1977).

Berzofsky et al., "Topographic Antigenic Determinants Recognized by Monoclonal Antibodies to Sperm Whale Myoglobin," *J. Biol. Chem.* 257(6), 3189–3198 (Mar. 25, 1982).

Berzofsky et al., "Properties of Monoclonal Antibodies Specific for Determinants of a Protein Antigen, Myoglobin," *J. Biol. Chem.* 255(23), 11188–11191 (Dec. 10, 1980).

Betsholtz et al., "cDNA sequence and chromosomal localization of human platelet-derived growth factor A-chain and its expression in tumour cell lines," *Nature* 320, 695–699 (Apr. 24, 1986).

Billat et al., "In Vitro and In Vivo Regulation of Hepatic Erythropoiesis by Erythropoietin and Glucocorticoids in the Rat Fetus," *Exp. Hematol.*, 10(1), 133–140 (1982).

Blattner et al., "Charon Phages: Safer Derivatives of Bacteriophage Lambda for DNA Cloning," *Science*, 196, 161–169 (Apr. 8, 1977).

Bos et al., "Eukaryotic Expression of Cloned cDNA Coding for Influenza Viral Glycoproteins Using an SV40 Vector: Use of Recombinant DNA Mutants to Study Structure-Function Relationships[1]," *Proc. Symp. Mol. Biol. Negat. Strand Viruses Meeting*, pp. 125–130, Compans et al., eds., Acad. Press (1984).

Bray et al., "Human cDNA clones for four species of Gα-signal transduction protein," *P.N.A.S.* (USA), 83, 8893–8897 (Dec. 1986).

Breslow et al., "Isolation and characterization of cDNA clones for human apolipoprotein A–I," *P.N.A.S.* (USA), 79, 6861–6865 (Nov. 1982).

Broome et al., "Immunological screening method to detect specific translation products," *P.N.A.S.* (USA), 75(6), 2746–2749 (Jun. 1978).

Browne, et al., "Erythropoietin: Gene Cloning, Protein Structure, and Biological Properties," *Cold Spring Harbor Symposia on Quantitative Biology*, LI,693–702 (1986).

Canaani et al., "Regulated expression of human interferon β1 gene after transduction into cultured mouse and rabbit cells," *P.N.A.S.* (USA), 79, 5166–5170 (Sep. 1982).

Chan et al., "Construction and selection of recombinant plasmids containing full-length complementary DNAs corresponding to rat insulins I and II," *P.N.A.S.* (USA), 76(10), 5036–5040 (Oct. 1979).

Chia et al., "The construction of cosmid libraries of eukaryotic DNA using the Homer series of vectors," *Nucleic Acids Res.* 10(8), 2503–2520 (1982).

Chiba et al., "Stabilization of Urinary Erythropoietin," *Biochem. and Biophys. Res. Commun.*, 47(6), 1372–1377 (1972).

Chirgwin et al., "Isolation of Biologically Active Ribonucleic Acid from Sources Enriched in Ribonuclease," *Biochemistry*, 18(24), 5294–5299 (1979).

Chisholm, "On the Trail of the Magic Bullet: Monoclonal antibodies promise perfectly targeted chemicals," *High Technology*, vol. 2(1), 57–63 (Jan. 1983).

Chomczynski et al., "Alkaline Transfer of DNA to Plastic Membrane," *Biochem. Biophys. Res. Commun.*, 122(1), 340–44 (Jul. 18, 1984).

Choo et al., "Molecular cloning of the gene for human anti-haemophilic factor IX," *Nature*, 299, 178–180 (Sep. 9, 1982).

Choppin et al., "Characterization of Erythropoietin Produced by IW32 Murine Erythroleukemia Cells," *Blood*, 64(2), 341–347 (Aug. 1984).

Chou et al., "Prediction of the Secondary Structure of Proteins from their Amino Acid Sequence," *Advances in Enzymology*, 47, 45–47 (1978).

Chou et al., "Empirical Predictions of Protein Conformation," *Ann. Rev. Biochem.*, 47, 251–276 (1978).

Chou et al., "Prediction of Protein Conformation," *Biochem.*, 13(2), 222–245 (1974).

Christman et al., "Amplification of expression of hepatitis B surface antigen in 3T3 cells cotransfected with a dominant-acting gene and cloned viral DNA," *P.N.A.S.* 79, 1815–1819 (Mar. 1982).

Claus-Walker et al., "Spinal Cord Injury and Serum Erythropoietin," *Arch. Phys. Med. Rehabil.*, 65, 370–374 (Jul. 1984).

Colby et al., "Immunological Differentiation Between *E. coli* and CHO Cell-Derived Recombinant and Natural Human β-Interferons[1]," *J. Immunol.* 133(6) 3091–3095 (1984).

Collen et al., "Biological Properties of Human Tissue-Type Plasminogen Activator Obtained by Expression of Recombinant DNA in Mammalian Cells," *J. of Pharmacology and Exp. Therapeutics*, 231 (1), 146–152 (1984).

Colman, "Cells that secrete foreign proteins," *TIBS*, 435–437 (Dec. 1982).

Comb et al., "Primary structure of the human Met- and Leu-enkephalin precursor and its mRNA," *Nature*, 295, 663–666 (Feb. 25, 1982).

Congote, "Regulation of Fetal Liver Erythropoiesis," *J. of Steroid Biochemistry*, 3, 423–428 (1977).

Congote, "Extraction from Fetal Bovine Serum of Erythrotropin, an Erythroid Cell-Stimulating Factor," *Anal. Biochem.*, 140, 428–433 (1984).

Congote, "Isolation of Two Biologically Active Peptides, Erythrotropin I and Erythrotropin II from Fetal Calf Intestine," *Biochem. Biophys. Res. Comm.*, 115(2), 477–483 (Sep. 15, 1983).

Congote et al., "The Erythrotropins, New Erythroid Cell Stimulating Factors Extracted From Human and Bovine Fetal Tissues," Abstract 364, Proceedings 7th International Congress of Endocrinology (Quebec City, Quebec, Jul. 1–7, 1984).

Contrera et al., "Extraction of erythropoietin from Kidneys of Hypoxic and Phenylhydrazine-treated rats," *Blood*, 25(5), 809–816 (May 1965).

Costantini et al., "Introduction of a Rabbit Betaglobin Gene into the Mouse Gem Line," *Nature*, 294, 92–94 (Nov. 5, 1981).

Costantini et al., "Gene Transfer into the Mouse Germ-Line," *J. Cell Physiol. Supp.* 1, 219–226 (1982).

Cotes et al., "Changes in serum immunoreactive erythropoietin during the menstrual cycle and normal pregnancy," *Brit. J. Obstet. Gynaecol.*, 90, 304–311 (Apr. 1983).

Cotes et al., "Bio-Assay of Erythropoietin in Mice made Polycythaemic by Exposure to Air at a Reduced Pressure," *Nature*, 191, 1065–1067 (Sep. 9, 1961).

Dainiak et al., "Mechanisms of Abnormal Erythropoiesis in Malignancy," *Cancer*, 51(6), 1101–1106 (1983).

Das et al., "Use of synthetic oligonucleotide probes complementary to genes for human HLA–DRα and β as extension primers for the isolation of 5′-specific genomic clones," *P.N.A.S. (USA)*, 80, 1531–1535 (Mar. 1983).

Davis et al., "A Manual for Genetic Engineering, Advanced Bacterial Genetics", Cold Spring Harbor Laboratory, Cold Spring Harbor, NY (1983), pp. 55–58 & 174–176.

Davis et al., "Active Influenza Virus Neuraminidase is Expressed in Monkey Cells from cDNA Cloned in Simian Virus 40 Vectors," *Proc. Nat'l. Acad. Sci. (USA)*, 80, 3976–3980 (1983).

Derynck et al., "Human transforming growth factor–βcomplementary DNA sequence and expression in normal and transformed cells," *Nature*, 316, 701–705 (Aug. 22, 1985).

Derynck et al., "Human Transforming Growth Factor–α,: Precursor Structure and Expression in *E. coli*,"*Cell*, 38, 287–297 (Aug. 1984).

Dessypris et al., "Effect of pure erythropoietin on DNA-synthesis by human marrow day 15 erythroid burst forming units in short-term liquid culture," *Brit. J. Haematol.* 56, 295–306 (1984).

Devos et al., "Purification of Recombinant Glycosylated Human Gamma Interferon Expressed in Transformed Chinese Hamster Ovary Cells," *J. Interferon Research*, 4, 461–468 (1984).

Docherty et al., "Sequence of human tissue inhibitor of metalloproteinases and its identity to erythroid-potentiating activity," *Nature*, 318, 66–69 (Nov. 7, 1985).

Dordal et al., "Function and Composition of the Carbohydrate Portion of Human Urinary Erythropoietin," *Experimental Hematology*, 10, Supp. 11, p. 133, Abstract No. 222 (1982).

Dordal et al., "The Role of Carbohydrate in Erythropoietin Action," *Endocrinology*, 116(6), 2293–2299 (1985).

Dreesman et al., "Antibody to hepatitis B surface antigen after a single inoculation of uncoupled synthetic HBsAg peptides," *Nature*, 295, 158–160 (Jan. 14, 1982).

Dunn et al., "Use of a computer model in the understanding of erythropoietic control mechanisms," Chemical Abstracts, 91, 190417r (1979).

Dunn, "Current Concepts in Erythropoiesis", John Wiley & Sons, Chichester, England, 1983.

Dunn et al., "Serum erythropoietin titers during prolonged bedrest; relevance to the anaemia of space flight," *Eur. J. Appln. Physiol.*, 52, 178–182 (1984).

Dunn et al., "Erythropoietin Bioassays Using Fetal Mouse Liver Cells: Validations and Technical Improvements," *Exp. Hematol.*, 11 (7), 590–600 (Aug. 1983).

Edman et al. "A Protein Sequenator," *Eur. J. Biochem.* 1, 80–91 (1967).

Emmanouel et al., "Metabolism of pure human erythropoietin in the rat," *Am. J. Physiol.*, 247 (1 Pt 2), F168–76 (1984).

Eschbach et al., "Correction by Erythropoietin (EPO) Therapy of the Anemia of Chronic Renal Failure (CRF) in Sheep," *Clin. Res.* 29(2), 518A (1981).

Eschbach et al., "The Anemia of Chronic Renal Failure in Sheep," *J. Clin. Invest.*, 74(2), 434–441 (Aug. 1984).

Espada et al., "Purification of Human Urinary Erythropoietin," *Fed. Proc.* 41, 1159 (1982).

Fan et al., "Construction and Characterization of Moloney Murine Leukemia Virus Mutants Unable to Synthesize Glycosylated Gag Polyprotein," *Proc. Nat'l. Acad. Sci. (USA)*, 80, 5965–5969 (1983).

Farber et al., "Translation of mRNA from human kidneys into biologically active erythropoietin following microinjection into xenopus laevis oocytes," *J. Lab. Clin. Med.*, 102, 681 abstract (Nov. 1983).

Farber et al., "Translation of mRNA from Anemic Baboon Kidney into Biologically Active Erythropoietin," *Exp. Hematol.*, 11, Supp. 14, Abstract 101 (1983).

Farber, "Translation of RNA from Human Kidneys into Biologically Active Erythropoietin Following Microinjection into Xenopus Laevis Oocytes," *Clin. Res.*, 31 (4), 769A (Nov. 1983).

Farber et al., "Translation of mRNA from Human Kidneys into Biologically Active Erythropoietin Following Microinjection into Xenopus Laevis Oocytes," *Blood*, 62(5), Supp. No. 1, Abstract 392, 122a (1983).

Fiddes et al., "The Gene Encoding the Common Alpha Subunit of the Four Human Glycoprotein Hormones," *J. Mol. & App. Genetics*, 1, 3–18 (1981).

Fiers et al., "The Human Firbroblast and Human Immune Interferon Genes and Their Expression in Homologous and Heterologous Cells," *Phil. Trans. R. Soc. Lond.*, B299, 29–38 (1982).

Finch, "Erythropoiesis, Erythropoietin, and Iron," *Blood*, 60(6), 1241–1246 (Dec. 1982).

Fischinger et al., "Detection of a Recombinant Murine Leukemia Virus–Related Glycoprotein on Virus–Negative thymona Cells," *Proc. Nat'l. Acad. Sci. (USA)*, 78(3), 1920–1924 (1981).

Fisher et al., "Cooperative Erythropoietic Assay of Several Steroid Metabolites in Polycythemic Mice," *Steroids*, 30(6), 833–845 (Dec. 1977).

Fisher, "Erythropoietin: Pharmacology, Biogenesis and Control of Production," *Pharmacological Review*, 24(3), 459–508 (1972).

Fisher, "Control of Erythropoietin Production," *Proc. Soc. Exp. Biol. & Med.* 173, 289–305 (1983).

Fisher et al., "Effects of testosterone, cobalt & hypoxia on erythropoietin production in the isolated perfused dog kidney," *Ann. N.Y. Acad. Sci.*, 75–87 (1967).

Garcia et al., "Radioimmunoassay of erythropoietin: circulating levels in normal and polycythemic human beings," *J. Lab. Clin. Med.*, 99, 624–635 (May 1982).

Garcia et al., "Radioimmunoassay of Erythropoietin," *Blood Cells* 5, 405–419 (1979).

Garcia et al., "Immunological Neutralization of Various Erythropoietins," *Proc. Soc. Exptl. Biol. Med.*, 112, 712–714 (1963).

Garoff et al., "Expression of Semliki Forest Virus Proteins from Cloned Complementary DNA. II. The Membrane-spanning Glycoprotein E2 is Ttransported to the Cell Surface Without Its Normal Cytoplasmic Domain," *J. Cell. Biol.*, 97, 652–658 (1983).

Gasser et al., "Expression of abbreviated mouse dihydrofolate reductase genes in cultured hamster cells," *P.N.A.S. (USA)*, 79, 6522–6526 (Nov. 1982).

Gene Screen, New England Nuclear, Catalog No. NEF–972.

Gething et al., "Comparison of Different Eukaryotic Vectors for the Expression of Hemagglutinin Glycoprotein of Influenza Virus," *Modern Approaches To Vaccines*, pp. 263–268, Chanock et al., eds. Cold Spring Harbor Lab (1984).

Gething et al., "Construction of influenza haemagglutin genes that code for intracellular and secrete forms of the protein," *Nature*, 300, 598–603 (Dec. 16, 1982).

Gething et al., "Cell–surface expression of influenza haemagglutinin from a cloned DNA copy of the RNA gene", *Nature*, 293, 620–625 (22 Oct. 1981).

Gibson et al., "An Evaluation of Serum Erythropoietin Estimation By a Hemagglutination Inhibition assay in the Differential Diagnosis of Polycythemia," *Pathology*, 16, 155–156 (Apr. 1984).

Gluzman, "SV40–Transformed Simian Cells Support the Replication of Early SV40 Mutants," *Cell* 23, 175–182 (Jan. 1981).

Goeddel et al., "Synthesis of human fibroblast interferon by *E. coli*," *Nucleic Acids Res.*, 8(18), 4057–4074 (1980).

Goeddel et al., "Human leukocyte Interferon Produced by *E. coli* is biologically active," *Nature*, 287:411–416 (Oct. 2, 1980).

Goldwasser et al., "Erythropoietin: Assay and Study of Its Mode of Action," *Meth. in Enzymol.*, 37, 109–121 (1975).

Goldwasser, "From Protein to Gene to Protein: The Molecular Biology of Erythropoietin," *Am. J. of Kidney Diseases*, 18(4) Supp. 1, 10–13 (Oct. 1991).

Goldwasser, "Biochemical Control of Erythroid Development," *Current Topics in Developmental Biology*, ed. A. Monroy and A.A. Noscona, 173–211, Academic Press, NY (1966).

Goldwasser et al., "The Molecular Weight of Sheep Plasma Erythropoietin," *J. of Biol. Chem.*, 247(16), 5159–60 (Aug. 25, 1972).

Goldwasser et al., "Progress in the purification of erythropoietin," *Ann. N.Y. Acad. Sci.*, 149:49–53 (1968).

Goldwasser et al., "On the mechanism of Erythropoietin–induced Differentiation," *J. of Biol. Chem.*, 249(13), 4202–4206 (Jul. 10, 1974).

Goldwasser et al., "Purification of Erythropoietin," *P.N.A.S. (USA)*, 68(4), 697–698 (Apr. 1971).

Goldwasser et al., "Further purification of sheep plasma erythropoietin", *Bioch. Biophys. Acta*, 64, 487–496 (1962).

Goldwasser, "Some Thoughts on the Nature of Erythropoietin–Responsive Cells," *J. Cell. Physiol.*, 110 (Supp. 1), 133–135 (1982).

Goldwasser et al., "An Assay for Erythropoietin in Vitro at the Milliunit Level," *Endocrinology*, 97(2), 315–323 (Aug. 1975).

Goldwasser et al., "Erythropoietin and the differentiation of red blood cells," *Fed. Proc.* 34, 2285–2292 (Dec. 1975).

Goochee et al., "Environmental Effects on Protein Glycosylation," *Biotechnology*, 8, 421–427 (May 1990).

Goochee et al., "The Oligosaccharides of Glycoproteins: Bioprocess Factors Affecting Oligosaccharide Structure and their Effect on Glycoprotein Properties," *Biotechnology*, 9, 1347–1555 (Dec. 1991).

Goodman et al., "Cloning of Homone Genes from a Mixture of cDNA Molecules," *Meth. in Enzymol.* 68, 75–90 (1979).

Gordon et al., "A plasma extract with erythropoietic activity," *Proc. Soc. Expt. Biol. Med.*, 86:255–258 (1954).

Goto et al., "Production of Recombinant Human Erythropoietin in Mammalian Cells: Host–Cell Dependency of the Biological Activity of the Cloned Glycoprotein," *BioTech.* 6, 67–71 (Jan. 1988).

Gough et al., "Immunoprecipitation of Specific Polysomes Using *Staphylococcus aureus*: Purification of the Immunoglobulin–Chain Messenger RNA from the Mouse Myeloma MPC11," *Biochemistry* 17(25), 5560–5566 (1978).

Gough et al., "Molecular Cloning of cDNA Encoding a Murine Haematopoietic Growth Regulator, Granulocyte–Macrophage Colony Stimulating Factor",*Nature*, 309, 763–767 (1984).

Gouy et al., "Codon Usage in Bacteria: Correlation with Gene Expressivity," *Nucleic Acids Res.* 10, 7055–7074 (1982).

Graham et al., "A New Technique for the Assay of Infectivity of Human Adenovirus 5 DNA," Virology 52, 456–467 (1973).

Grantham et al., "Codon catalog usage is a genome strategy modulated for gene expressivity," *Nucleic Acids Res.* 9, r43–74 (1981).

Gray et al., "*Pseudomonas aeruginosa* Secretes and Correctly Processes Human Growth Hormone," *Biotechnology*, 2, 161–165 (Feb. 1984).

Gray et al., "Expression of human immune interferon cDNA in *E. coli* and monkey cells," *Nature*, 295, 503–508 (Feb. 11, 1982).

Green et al., "Immunogenic Structure of the Influenza Virus Hemagglutinin," *Cell*, 28, 477–487 (Mar. 1982).

Greenwood et al., "The Preparation of $^{131}$I–Labelled Human Growth Hormone of High Specific Radioactivity," *Biochem. J.*, 89, 114–123 (1963).

Grimaldi et al., "Interspersed repeated sequences in the African green monkey genome that are homologous to the human Alu family," *Nucleic Acid Research*, 9(21), 5553–5568 (1981).

Groffen et al. "Isolation of Human Oncogene Sequences (v–fes Homolog) from a Cosmid Library," *Science*, 216, 1136–1138 (Jun. 4, 1982).

Grundmann et al., "Characterization of cDNA coding for human factor XIIIa," *P.N.A.S. (USA)*, 83, 8024–8028 (Nov. 1986).

Grunstein et al., "Colony Hybridization," *Meth. in Enzym.* 68, 379–389 (1979).

Grunstein et al., "Colony hybridization: A method for the isolation of cloned DNAs that contain a specific gene," *P.N.A.S. (USA)*, 72(10), 3961–3965 (Oct. 1975).

Gruss et al., "Expression of simian virus 40–rat preproinsulin recombinants in monkey kidney cells: Use of preproinsulin RNA processing signals," *P.N.A.S. (USA)*, 78(1), 133–137 (Jan. 1981).

Gubler et al., "A simple and very efficient method for generating cDNA libraries," *Gene* 25, 263–269 (1983).

Haddy, "Erythropoietin in sickle cell disease," *Am. Jour. Ped. Hematol./Oncol.*, 4(2), 191–196 (Summer 1982).

Haga et al., "Plasma Erythropoietin Concentrations During the Early Anemia of Prematurity," *Acta. Pediatr. Scand*, 72, 827–831 (1983).

Hagiwara et al., "Erythropoietin Production in a Primary Culture of Human Renal Carcinoma Cells Maintained in Nude Mice," *Blood*, 63(4), 828–835 (Apr. 1984).

Hamer et al., "Expression of the chromosomal mouse $\beta^{maj}$–globin gene cloned in SV40," *Nature*, 281, 35–40 (Sep. 6, 1979).

Hamer et al., "A Mouse Globin Gene Promoter is Functional in SV40," *Cell*, 21, 697–708 (Oct. 1980).

Hammond et al., "Production, Utilization and Excretion of Erythropoietin: I. Chronic Anemias. II. Aplastic Crisis. III. Erythropoietic Effects of Normal Plasma," *Ann. N.Y. Acad. Sci.*, 149, 516–527 (1968).

Hanahan et al., "Plasmid screening at high colony density," *Gene*, 10, 63–67 (1980).

Hartman et al., "Human Influenza Virus Hemagglutinin is Expressed in Monkey Cells Using Simian Virus 40 Vectors," *Proc. Nat'l. Acad. Sci. (USA)*, 79,233–237 (1982).

Hauser et al., "Inducibility of human β–interferon in mouse L–cell clones," *Nature*, 297, 650–654 (Jun. 24, 1982).

Haynes et al., "Constitutive, long–term production of human interferons by hamster cells containing multiple copies of a cloned interferon gene," *Nucleic Acids Research*, 11(3), 587–607 (1983).

Haynes et al., "Production of a Glycosylated Human Protein by Recombinant DNA Technology," Humoral Factors Host Ref. [Proc. Takeda Sci. Found. Symp. Biosci. (1983)], 1st, Meeting Date 1982, 111–29.

Hellmann et al., "Familial erythrocytosis with over–production of erythropoietin," *Clin. Lab. Haemat.*, 5, 335–342 (1983).

Hewick et al., "A Gas–Liquid Solid Phase Peptide and Protein Sequenator," *J. Biol. Chem.*, 256, 7990–7997 (Aug. 1981).

Higashi et al., "Structure and Expression of a Cloned cDNA for Mouse Interferon–β*," *J. Biol. Chem.*, 258(15):9522–9529 (1983).

Higashi et al., "Characterization of N–Glycolyineuraminic Acid–containing Gangliosides as Tumor–associated Hanganutziu–Deicher Antigen in Human Colon Cancer," *Cancer Research*, 45, 3796–3802 (1985).

Hirs et al., "Peptides Obtained by Tryptic Hydrolysis of Performic Acid–Oxidized Ribonuclease," *J. Biol. Chem.* 219, 623–642 (1955).

Hokke et al., "Sialylated carbohydrate chains of recombinant human glycoproteins expressed in Chinese hamster ovary cells contain traces of N–glycolyneuraminic acid," *FEBS Letters*, 275, 9–14 (1990).

Hopp et al., "Prediction of protein antigenic determinants from amino acid sequences," *P.N.A.S. (USA)*, 78(6), 3824–3828 D–7182 (Jun. 1981).

Houghton et al., "The amino–terminal sequence of human fibroblast interferon as deduced from reverse transcripts obtained using synthetic oligonucleotide primers," *Nucleic Acids Res.* 8(9), 1913–1931 (1980).

Huang et al., "Identification of Human Erythropoietin Receptor," *Am. Soci. of Biological Chemists, Am. Assoc. of Immunologists, Fed. Pract. (USA)* 43(7) Abst. 2770, p. 1891 (1984).

Huang et al., "Characterization of Human Erythropoietin cDNA clones," *Am. Soc. of Biological Chemists, Am. Assoc. of Immunologists, Fed. Pract. (USA)* 43(6) Abst. 1795, p. 1724.

Imai et al., "Physicochemical and Biological Comparison of Recombinant Human Erythropoietin with Human Urinary Erythropoietin" *J. Biochem*, 107, 352–359 (1990).

Itakura, et al., "Synthesis and Use of Synthetic Oligonucleotides," *Ann. Rev. Biochem.*, 53, 323–356 (1984).

Ito et al., "Solid phase synthesis of polynucleotides. VI. Further studies on polystyrene copolymers for the solid support," *Nucleic Acids Res.* 10(5), 1755–1769 (1982).

Jacobs et al., "Isolation and characterization of genomic and cDNA clones of human erythropoietin," *Nature*, 313, 806–809 (Feb. 28, 1985).

Jacobsen et al., "Relative effectiveness of phenylhydrazine treatment and hemorrhage in the production of an erythropoietic factor," *Blood*, 11:937–945 (1956).

Jacobson et al., "Role of the kidney in erythropoiesis," *Nature*, 179:633–634 (Mar. 23, 1957).

Jaye et al., "Isolation of human anti–haemophilic factor IX cDNA clone using a unique 52–base synthetic oligonucleotide probe deduced form the amino acid sequnce of bovine factor IX," *Nucleic Acids Res.* 11(8), 2325–2335 (1983).

Jeffreys et al., "Sequence variation and evolution of nuclear DNA in man and the primates," *Phil. Trans. R. Soc. Lond.*, B 292, 133–142 (1981).

Jelkman et al., "Extraction of Erythropoietin from Isolated Renal Glomeruli of Hypoxic Rats," *Exp. Hematol.*, 11(7), 581–588 (Aug. 1983).

Kaiser et al., "Amphiphilic Secondary Struture: Design of Peptide Hormones," *Science*, 223, 249–255 (1984).

Kajimura et al., "Cloning the Heavy Chain of Human HLA–DR Antigen Using Synthetic Oligodeoxyribonucleotides as Hybridization Probes," *DNA*, 2(3), 175–182 (1983).

Kakidani et al., "Cloning and sequence analysis of cDNA for porcine β–neo–endorphin/dynorphin precursor," *Nature*, 298, 245–249 (Jul. 15, 1982).

Kalmanti, "Correlation of clinical and in vitro erythropoietic responses to androgens in renal failure," *Kidney Int'l.*, 22, 383–391 (1982).

Karn et al., "Novel bacteriophage λ cloning vector," *P.N.A.S. (USA)*, 77, 5172–5176 (Sep. 1980).

Katsuoka et al., "Erythropoietin Production in Human renal Carcinoma Cells Passaged in Nude Mice and in Tissue Culture," *Gann*, 74, 534–541 (Aug. 1983).

Kaufman et al., "Amplification and Expression of Sequences Cotransfected with a Modular Dihydrofolate Reductase Complementary DNA Gene," *J. Mol. Biol.* 159, 601–621 (1982).

Kaufman et al., "Expression and Amplification of DNA Introduced into Mammalian Cells," *Gene Amplification*, RT Schimke ed., Cold Spring Harbor, New York, 245–250 (1982).

Kennell, "Principles and Practices of Nucleic Acid Hybridization," *Prog. Nucl. Acid Res. Mol. Biol.* 11, 259–301 (1971).

Kenter et al., "Mouse Myeloma Cells That Make Short Immunoglobulin Heavy Chains: Pleitropic Effects on Glycosylation and Chain Assembly," *J. Cell. Biol.*, 98, 215–2221 (1984).

Kieny et al., "Expression of rabies virus glycoprotein from a recombinant vaccinia virus," *Nature*, 312, 163–166 (1984).

Kimura et al., "A frameshift addition causes silencing of the δ–globin gene in old world monkeys, an anubis," *Nucleic Acids Res.*, 11(9):2541–2550 (1983).

Knopf et al., "Cloning and Expression of Multiple Protein Kinase C cDNAs," *Cell* 46, 491–502 (Aug. 15, 1986).

Kohne, "Evolution of Higher–organism DNA," *Quarterly Reviews of Biophysics*, 3:327 . 375 (1970).

Kondor–Koch et al., "Expression of Semliki Forest Virus Proteins from Cloned Complementary DNA. I. The Fusion Activity of the Spike Glycoprotein," *J. Cell. Biol.*, 97, 644–651 (1983).

Konrad, "Applications of Genetic Engineering to the Pharmaceutical Industry," *Ann. N.Y. Acad. Sci.*, 413, 12–22 (1983).

Konwalinka et al., "A Miniaturized Agar Culture System for Cloning Human Erythropoietic Progenitor Cells," *Exp. Hematol.*, 12, 75–79 (1984).

Korman, "cDNA clones for the heavy chain of HLA-DR antigens obtained after immunopurification of polysomes by monoclonal antibody," *P.N.A.S. (USA)*, 79, 1844–1848 (Mar. 1982).

Kornblihtt et al., "Isolation and characterization of cDNA clones for human and bovine fibronectins," *P.N.A.S. (USA)*, 80, 3218–3222 (Jun. 1983).

Kramer et al., "Comparisons of the Complete Sequences of Two Collagen Genes from Caenorhabditis elegans," *Cell 30*, 599–606 (Sep. 1982).

Krane, "The Role of Erythropoietin in the Anemia of Chronic Renal Failure," *Henry Ford Hosp. Med. J.*, 31(3), 177–181 (1983).

Krystal, "A Simple Microassay for Erythropoietin Based on ³H-Thymidine Incorporation into Spleen cells from Phenylhydrazine Treated Mice," *Exp. Hematol.*, 11(7), 649–660 (Aug. 1983).

Kuhn et al., "Gene Transfer, Expression, and Molecular Cloning of the Human Transferrin Receptor Gene," *Cell*, 37, 95–103 (1984).

Kurachi et al., "Isolation and characterization of a cDNA coding for human factor IX," *P.N.A.S. (USA)*, 79, 6461–6464 (Nov. 1982).

Kuratowska et al. "Studies on the production of erythropoietin by isolated perfused organs," *Blood*, 18:527–534 (1961).

Kurtz, "A New candidate for the regulation of erythropoiesis: Insulin-like growth factor I," *FEBS Letters*, 149(1), 105–108 (Nov. 1982).

Kyte et al., "A Simple Method for Displaying the Hydropathic Character of a Protein," *J. Mol. Biol.*, 157, 105–132 (1982).

Lai et al., "Ovalbumin is synthesized in mouse cells transformed with the natural chicken ovalbumin gene," *P.N.A.S. (USA)*, 77(1), 244–248 (Jan. 1980).

Lai et al., "Structural Characterization of Human Erythropoietin," *J. of Biol. Chem.*, 261, 3116–3121 (Mar. 5, 1986).

Lai, "Technical improvements in Protein Microsequencing," *Analytica Chimica Acta*, 163, 243–248 (1984).

Lange et al. "Application of erythropoietin antisera to studies of erythropoiesis," *Ann. N.Y. Acad. Sci.*, 149:281–291 (1968).

Lappin et al., "The Effect of Erythropoietin and Other Factors on DNA synthesis by Mouse Spleen Cells," *Exp. Hematol.*, 11(7), 661–666 (Aug. 1983).

Lasky et al., "Production of an HSV Subunit Vaccine by Genetically Engineered Mammalian Cell Lines," *Modern Approaches to Vaccines*, pp. 189–194, Chanock et al., eds. Cold Spring Harbor Lab. (1984).

Lathe, "Synthetic Oligonucleotide Probes Deduced from Amino Acid Sequence Data," *J. Mol. Biol.* 183, 1–12 (1985).

Laub and Ritter, "Expression of the Human Insulin Gene and cDNA in a Heterologous Mammalian System," *J. Biol. Chem.*, 258(10), 6043–6050 (May 25, 1983).

Laub et al., "Synthesis of Hepatitis B Surface Antigen in Mammalian Cells: Expression of the Entire Gene and the Coding Region," *J. Viol.*, 48(1):271–280 (1983).

Lauffer et al., "Topology of signal recognition particle receptor in endoplasmic reticulum membrane," *Nature*, 318, 334–338 (Nov. 28, 1985).

Lawn et al., "The Isolation and Characterization of Linked δ- and β-Globin Genes from a Cloned Library of Human DNA," *Cell*, 15, 1157–1174 (Dec. 1978).

Ledeen et al., "Gangliosides: Structure, Isolation, and Analysis," *Methods in Enzymology*, 83 (Part D), 139–191 (1982).

Lee-Huang, "The Erythropoietin Gene," *Oncogenes, Genes and Growth Factors*, Chap. 7, pp. 199–222, ed. Gordon Garaff, John Wiley & Sons, Inc. (1987).

Lee-Huang, "Cloning of Human Erythropoietin," *Biophysical J.*, 45(Part 2 of 2), ABT. M-PM-A12, p. 30a (1984).

Lee-Huang, "Monoclonal Antibodies to Human Erythropoietin," *Abstract No. 1463, Fed. Proc.*, 41,520 (1982).

Lee-Huang, "A New Preparative Method for Isolation of Human Erythropoietin With Hydrophobic Interaction Chromatography," *Blood*, 56(4), 620–624 (Oct. 1980).

Lee-Huang, "Cloning and Expression of Human EPO cDNA in *E. Coli*," *P.N.A.S. (USA)*, 81, 2708–2712 (May 1984).

Lerner et al., "Chemically synthesized peptides predicted from the nucleotide sequence of the hepatitis B virus genome elicit antibodies reactive with the native envelope protein of Dane particles," *P.N.A.S. (USA)*, 78(6), 3403–3407 (Jun. 1981).

Lerner, "Synthetic Vaccines," *Scientific American*, 248(2), 66–74 (1983).

Lerner et al., "Antibodies to Chemically Synthesized Peptides Predicted from DNA Sequences as Probes of Gene Expression," *Cell*, 23, 309–310 (Feb. 1981).

Lewin *Genes*, 1983, John Wiley & Sons, p. 307.

Lin et al., "Cloning and expression of the human erythropoietin gene," *P.N.A.S. (USA)*, 82, 7580–7584 (Nov. 1985).

Lin et al., "Monkey erythropoietin gene: cloning, expression and comparison with the human erythropoietin gene," *Gene*, 44, 201–209 (1986).

Lin et al., "Cloning of the Monkey EPO Gene," Abstract, *J. Cell. Bioch.*, Suppl. 8B, p. 45 (Mar. 31–Apr. 24, 1984).

Lin et al., "Cloning and Expression of Monkey and Human Erythropoietin," *Exp. Hematol.* 12, 357 (1984).

Lipschitz et al., "Effect of Age on Hematopoiesis in Man," *Blood*, 63(3), 502–509 (Mar. 1983).

LKB Technical Bulletin #2217.

Maniatis et al. "The Isolation of Structural Genes from Libraries of Eucaryotic DNA," *Cell* 15, 687–701 (Oct. 1978).

Maniatis et al., "Molecular Cloning, a Laboratory Manual", pp. 5, 197–199, 392–393, 479–487, 493–503 Cold Springs Harbor, N.Y. (1982).

Markoff et al., "Glycosylation and Surface Expression of the Influenza Virus Neuraminidase Requires the N-Terminal Hydrophobic Region," *Molecular and Cellular Biology*, 4(1), 8–16 (1984).

Marshall, "Glycoproteins," *Annual Review of Biochemistry*, Snell et al. eds., vol. 41, pp. 673–702, Annual Reviews Inc., Palo Alto, California (1972).

Martial et al., "Human Growth Hormones: Complementary DNA Cloning and Expression in Bacteria," *Science*, 205, 602–606 (Aug. 10, 1979).

Mason et al., "Complementary DNA sequences of ovarian follicular fluid inhibin show precursor structure and homology with transforming growth factor-β," *Nature* 318, 659–663 (Dec. 1985).

Maurer, "Immunochemical Isolation of Prolactin Messenger RNA," *J. Biol. Chem* 255(1), 854–859 (Feb. 10, 1980).

Maxam et al., "Sequencing End-Labeled DNA with Base-Specific Chemical Cleavages," *Methods in Enzymol.* 65, 499–560 (1980).

McCormick et al., "Regulated Expression of Human Interferon Genes In Chinese Hamster Ovary Cells," *DNA*, 2(1): 86 Abst 86 (1983).

McCormick et al., "Inducible Expression of Amplified Human Beta Interferon Genes in CHO Cells," *Mol. Cell. Biol.*, 4(1):166–172 (Jan. 1984).

McGonigle et al., "Erythropoietin deficiency and inhibition of erythropoiesis in renal insufficiency," *Kidney Int'l.*, 25(2), 437–444 (1984).

Meier et al., "Alpha$_1$- and Beta$_2$-Adrenergic Receptors Co-Expressed on Cloned MDCK Cells are Distinct Glycoproteins," *Biochem. & Biophys. Res. Comm.*, 118(1), 73–81 (1984).

Mellon et al., "Identification of DNA Sequences Required for transcription of the human α1-Globin Gene in a New SV40 Host-Vector System," *Cell*, 27, 279–288 (Dec. 1981).

Mellor et al., "Expression of Murine H-2K$^b$ histocompatibility antigen in cells transferred with cloned H-2 genes," *Nature*, 298:529–534 (Aug. 1982).

Messing, "New M13 Vectors for Cloning," *Methods in Enzymology*, 101, 20–78 (1983).

Metcalf et al., "Effects of Purified Bacterially Synthesized Murine Multi-CSF (IL-3) on Hematopoiesis in Normal Adult Mice," *Blood*, 68(1), 46–57 (Jul. 1986).

Metcalf et al., "Quantitative Responsiveness of Murine Hemopoietic Populations in vitro and in vivo to Recombinant Multi-CSF (IL-3)," *Exp. Hematol.*, 15, 288–295 (1987).

Methods in Yeast Genetics, Cold Spring Harbor Lab, Cold Spring Harbor, NY, p. 62 (1983).

Miller et al., "Plasma levels of immunoreactive erythropoietin after acute blood loss in man," *Brit. J. Haematol.*, 52, 545–549 (1982).

Mirand, "Extra-renal and renal control of erythropoietin production," *Ann. N.Y. Acad. Sci.*, 149:94–106 (1968).

Mirand et al., "Current studies on the role of erythropoietin on erythropoiesis", *Ann. N.Y. Acad. Sci.*, 77:677–702 (1959).

Miyake et al., "Purification of Human Erythropoietin," *J. Biol. Chem.*, vol. 252(15), 5558–5564 (Aug. 1977).

Mladenovic et al., "Anemia of Chronic Renal Failure (CRF) in the Sheep: Response to Erythropoietin (EP) In Vivo and In Vitro," *Blood*, 58(5), Suppl. 1, 99a (1981).

Montgomery et al., "Identification and Isolation of the Yeast Cytochrome c Gene," *Cell*, 14, 673–680 (Jul. 1978).

Moriarty et al., "Expression of the Hepatitis B Virus Surface Antigen Gene in Cell Culture by using a Simian Virus 40 Vector," *P.N.A.S. (USA)*, 78(4):2606–10 (Apr. 1981).

Moriuchi et al., "Thy-1 cDNA sequence suggests a novel regulatory mechanism," *Nature*, 301, 80–82 (Jan. 1983).

Morrison, "Bioprocessing in Space—an Overview", *The World Biotech Report*, vol. 2:USA, 557–571 (1984).

Munjaal et al., "A cloned calmodulin structural gene probe is complementary to DNA sequence from diverse species," *P.N.A.S. (USA)*, 78(4):2330–2334 (Apr. 1981).

Murphy et al., "The Role of Glycoprotein Hormones in the Regulation of Hematopoiesis," *Acta. Haematologica Japonica*, 46(7), 1380–1396 (Dec. 1983).

Myers et al., "Construction and Analysis of Simian Virus 40 Origins Defective in Tumor Antigen Binding and DNA Replication," *P.N.A.S. (USA)*, 77, 6491–6495 (Nov. 1980).

Myklebost et al., "The Isolation and Characterization of cDNA clones for Human Apolioprotein CII," *J. of Biol. Chem.*, 259(7), 4401–4404 (Apr. 10, 1984).

Naets, "The role of the kidney in erythropoiesis," *J. Clin. Invest.*, 39:102–110 (1960).

Nagata et al., "Synthesis in *E. Coli* of a polypeptide with human leukocyte interferon activity," *Nature*, 284, 316–320 (Mar. 27, 1980).

Nakao et al., "Erythropoiesis in anephric or kidney transplanted patients," *Israel J. Med. Sci.*, 7:986–989 (Jul.-Aug. 1971).

Nathan et al., "Erythropoietin and the Regulation of Erythropoiesis," *New Eng. J. Med.*, 308(9), 520–522 (Mar. 3, 1983).

Naughton et al., "Evidence for an Erythropoietin-Stimulating Factor in Patients with Renal and Hepatic Disease," *Acta. Haemat.*, 69, 171–179 (1983).

Naughton et al., "Evidence for a Hepatic-Renal Antagonism in the Production of Hepatic Erythropoietin," *Ann. Clin. Lab. Sci.*, 13(5), 432–438 (1983).

Nayak et al., "Characterization of Influenza Virus Glycoproteins Expressed from Cloned cDNAs in Prokaryotic and Eukaryotic Cells," *Modern Approaches To Vaccines*, pp. 165–172, Chanock et al., eds., Cold Spring Harbor Lab. (1984).

Neeser et al., "A Quantitative Determination by Capillary Gas-Liquid Chromatography of Neutral and Amino Sugars (as 0-Methyloxime Acetates), and a Study on Hydrolyric Conditions for Glycoproteins and Polysaccharides In Order to Increase Sugar Recoveries," *Anal. Biochem.*, 142, 58–67 (1984).

Newman et al., "Selection and Properties of a Mouse L-Cell Transformant Expressing Human Transferrin Receptor," *Nature*, 304, 643–645 (1983).

Nigg et al., "Immunofluorescent localization of the transforming protein of Rous sarcoma virus with antibodies against a synthetic src peptide," *P.N.A.S. (USA)*, 79, 5322–5326 (Sep. 1982).

Nimtz et al., "Structures of sialylated oligosaccharides of human erythropoietin expressed in recombinant BHK-21 cells," *Eur. J. Biochem*, 213, 39–56 (1993).

Noda et al., "Primary structure of c?-subunit precursor of *Torpedo californica* acetylcholine receptor deduced from cDNA sequence," *Nature*, 299, 793–797 (Oct. 28, 1982).

Noda et al., "Cloning and sequence analysis of cDNA for bovine adrenal preproenkephalin," *Nature*, 295, 202–206 (Jan. 21, 1982).

Noyes et al., "Detection and partial sequence analysis of gastrin mRNA by using an oligodeoxynucleotide probe," *P.N.A.S. (USA)*, 76(4), 1770–1774 (Apr. 1979).

Nussinov, "Eukaryotic Dinucleotide Preference Rules and their Implications for Degenerate Codon Usage," *J. Mol. Biol.*, 149, 125–131 (1981).

Ogle et al., "Production of erythropoietin in vitro: a review," In Vitro, 14(11), 945–949 (1978).

Ohkubo et al., "Cloning and sequence analysis of cDNA for rat angiotensinogen," *P.N.A.S. (USA)*, 80, 2196–2200 (Apr. 1983).

Ohno et al., "Inducer-responsive expression of the cloned human interferons β1 gene introduced into cultured mouse cells," *Nucleic Acids Res.*, 10(3), 967–976 (1982).

Okayama et al., "High-Efficiency Cloning of Full-Length cDNA," *Mol. & Cell. Biol.*, 2(2), 161–170 (Feb. 1982).

Ovchinnikov et al., "The Primary Structure of *Escherichia coli* RNA Polymerase," *J. Biochem.*, 116, 621–629 (1981).

Paabo et al., "Association Between Transplantation Antigens and a Viral Membrane Protein Synthesized from a Mammalian Expression Vector," *Cell*, 35, 445–453 (1983).

Palmiter et al., "Metallothionein–Human GH Fusion Genes Stimulate Growth of Mice," *Science*, 222, 809–814 (Nov. 18, 1983).

Pankratz et al., "A Simple 3-Step Procedure for Purifying Baboon Urinary Erythropoietin to Apparent Homogeneity," *Exp. Hematol.*, 11, Supp. 14, Abst. 102 (1983).

Papayannopoulou et al., "On the In Vivo Action of Erythropoietin: A Quantitative Analysis," *J. of Clin. Investigation*, 51, 1179–1185 (1972).

Parekh et al., "N–Glycosylation and in vitro Enzymatic Activity of Human Recombinant Tissue Plasminogen Activator Expressed in Chines Hamster Ovary Cells and a murine Cell Line," *Biochemistry*, 28, 7670–7679 (1989).

Pavlovic–Kentera et al., "Effects of Prostaglandin Synthetase Inhibitors, Salt Overload and Renomedullary Dissection on the Hypoxia Stimulated Erythropoietin Production in Rats," *Exp. Hematol.*, 8(Supp. 8), 283–291 (1980).

Pellicer et al. "Altering Genotype and Phenotype by DNA–Mediated Gene Transfer," *Science*, 209, 1414–1422 (Sep. 19, 1980).

Pennathur–Das et al., "Evidence for the Presence of CFU–E with Increased In Vitro Sensitivity to Erythropoietin in Sickle Cell Anemia," *Blood*, 63(5), 1168–71 (May 1984).

Pennica et al., "Cloning and expression of human tissue–type plasminogen activator cDNA in E–coli," *Nature*, 301,214–221 (Jan. 20, 1983).

Pennica et al., "Human tumour necrosis factor: precursor structure, expression and homology to lymphotoxin," *Nature*, 312, 724–728 (Dec. 27, 1984).

Pitha et al., "Induction of human B–interferon synthesis with poly (rI•rC) in mouse cells transfected with cloned cDNA plasmids," *P.N.A.S. (USA)*, 79, 4337–4341 (Jul. 1982).

"Points to Consider in the Characterization of Cell Lines Used to Produce Biologics," Jun. 1, 1984, Office of Biologics Research Review, Center for Drugs & Biologics, U.S. Food & Drug Administration (Section A, Part 2).

Powell et al., "Human erythropoietin gene: High level expression in stably transfected mammalian cells and chromosome localization," *P.N.A.S. (USA)*, 83, 6465–6469 (Sep. 1986).

Prooijen–Knegt, "In Situ Hybridization of DNA Sequences in Human Metaphase Chromosomes Visualized by an Indirect Fluorescent Immunocytochemical Procedure," *Exp. Cell Res.*, 141, 397–407 (1982).

Ramabhadran et al., "Synthesis and Glycosylation of the Common α Subunit of Human Glycoprotein Hormones in Mouse Cells," *Proc. Nat'l. Acad. Sci. (USA)*, 81, 6701–6705 (1984).

Rambach et al., "Acid Hydrolysis of Erythropoietin," *Proc. Soc. Exp. Biol.*, 99, 482–483 (1958).

Ravetech et al., "Evolutionary approach to the question of immunoglobulin heavy chain switching: Evidence from cloned human and mouse genes," *P.N.A.S. (USA)*, 77(11), 6734–6738 (Nov. 1980).

Recny et al., "Structural Characterization of Natural Human Urinary and Recombinant DNA–derived Erythropoietin," *J. Biol. Chem.*, 262(35), 17156–17163 (Dec. 15, 1987).

Reilly et al., "Use of synthetic oligonucleotides to clone genomic DNA: isolation of a tRNA$^{Phe}$ gene from mouse," *DNA*, 1:192 (1982).

Resegotti et al., "Treatment of aplastic anaemia with methenolone, stanozolol and nandrolone," *Panminerva medica*, 23, 243–248 (1981).

Reyes et al., "Identification of an H–2K$^b$–Related Molecule by Molecular Cloning," *Immunogenetics*, 14, 383–392 (1981).

Reyes et al., "Isolation of a cDNA clone for the murine transplantation antigen H–2K$^b$," *P.N.A.S. (USA)*, 79, 3270–3274 (May 1982).

Rigby, "Expression of cloned genes in eukaryotic cells using vector systems derived from viral replicons," *Genetic Engineering*, R. Williamson, ed., 3:83–140, Academic Press, London 1982.

Riggs et al., "Synthetic DNA and Medicine," *Am. J. Hum. Genet.*, 31, 531–538 (1979).

Ringold et al., "Co–Expression and Amplification of Dihydrofolate Reductase cDNA and the *Escherichia coli* XGPRT Gene in Chinese Hamster Ovary Cells," *J. Mol. & Appl. Genetics*, 1(3), 165–175 (1981).

Robson et al., "Polysome immunoprecipitation of phenylalanine hydroxylase mRNA from rat liver and cloning of its cDNA," *P.N.A.S. (USA)*, 79, 4701–4705 (Aug. 1982).

Roh et al., "Plasma Disappearance of I$^{125}$labeled Human Uninary Erythropoietin in Rabbits," *Fed. Proc.*, 29(2), 782 Abst. 3030 (1970).

Rose et al., "Expression from Cloned cDNA of Cell–Surface Secreted Forms of the Glycoprotein of Vesicular Stomatitis Virus in Eucaryotic Cells," *Cell*, 30, 753–762 (1982).

Ross et al., "Phosphotyrosine–containing proteins isolated by affinity chromatography with antibodies to a synthetic hapten," *Nature*, 294, 654–656 (Dec. 17, 1981).

Roth et al., "Influenza Virus Hemagglutinin Expression Is Polarized in Cells Infected with Recombinant SV40 Viruses Carrying Cloned Hemagglutinin DNA", *Cell*, 33, 435–443 (1983).

Rothmann et al., "Erythropoietin–Dependent Erythrocytosis Associated with Hepatic Angiosarcoma," *J. Surg. Oncol.*, 20, 105–108 (1982).

Saito et al., "Translation of Human Erythropoietin–mRNAs," *Exp. Hematol.*, 11(14), 228 (1983).

Saito et al., "In Vitro Assay of Erythropoietin: Simple Determination in a Small Amount of Human Serum Samples," *Jap. J. Med.*, 23(1), 16–21 (Feb. 1984).

Sambrook et al., "Expression of Proteins on the Cell Surface Using Mammalian Vectors," *Experimental Manipulation of Gene Expression*, pp. 225–246, Acad. Press. (1983).

Sanger et al., "DNA Sequencing with chain–terminating inhibitors," *P.N.A.S. (USA)*, 74, 5463–5467 (Dec. 1977).

Sasaki, "Carbohydrate Structure of Erythropoietin Expressed in Chinese Hamster Ovary Cells by a Human Erythropoietin cDNA," *J. Biol. Chem.*, 262(25), 12059–12070 (Sep. 5, 1987).

Sasaki, "Isolation of erythropoietin by monoclonal antibody," *Biomed. Biochim. Acta.*, 42(11/12), S202–206 (1983).

Seahill et al., "Expression and characterization of the product of a human immune interferon cDNA gene in Chinese hamster ovary cells," *Proc. Nat'l. Acad. Sci. (USA)*, 80, 4654–4658 (1983).

Schulze et al., "Identification of the cloned gene for the murine transplantation antigen H–2K$^b$ by hybridization with synthetic oligonucleotides," *Mol. & Cell Biol.*, 3(4), 750–755 (Apr. 1983).

Schwartz et al., "Severe Anemia as a Manifestation of Metastatic Jugular Paraganglioma," *Arch Otolaryngol*, 109, 269–272 (Apr. 1983).

Seeburg et al., "Synthesis of growth hormone by bacteria," *Nature*, 276, 795–798 (Dec. 1978).

Seki et al., "Isolation of a genomic clone containing structural information for the DRα subunit", *Fed. Proc.*, 41:365 (1982)/Chemistry and Molecular Biology of Ia/Dr Antigens Abstract 563 (1982).

Shahidi, "Androgens and Erythropoiesis," *New Eng. J. Med.*, 289, 72–80 (Jul. 12, 1973).

Sherwood et al., "Erythropoietin Titers in Sickle Cell Disease & Chronic Renal Failure," *Blood Suppl.* 1, 58, Abstract 105 (1981).

Sherwood et al., "Extraction of erythropoietin from normal kidneys," *Endocrinology*, 103(3), 866–870 (1978).

Sherwood et al., "A Radioimmunoassay for Erythropoietin," *Blood*, 54(4), 885–893 (Oct. 1979).

Shiramizu et al. "Human Renal Carcinoma Cells Secreting Erythropoietin in vivo and in vitro," *Blood*, 78(10), Supp. 1 (Nov. 15, 1991).

Singer–Sam et al., "Isolation of a cDNA clone for human X–linked 3–phosphoglycerate kinase by use of a mixture of synthetic oligodeoxyribonucleotides as a detection probe," *P.N.A.S. (USA)*, 80, 802–806 (Feb. 1983).

Smith et al., "Construction and characterization of an infectious vaccinia virus recombinant that expresses the influenza hemagglutinin gene and induces resistance to influenza virus infection in hamsters," *Proc. Nat'l. Acad. Sci. (USA)*, 80, 7155–7159 (1983).

Southern et al., "Transformation of Mammalian Cells to Antibiotic Resistance with a Bacterial Gene Under Control of the SV40 Early Region Promoter," *J. Mol. Appl. Genet.*, 1(4), 327–341 (1982).

Southern, "Detection of Specific Sequences Among DNA Fragments Separated by Gel Electrophoresis," *J. Mol. Biol.*, 98, 503–517 (1975).

Spellman et al., "Carbohydrate Structure of Recombinant Soluble Human CD4 Expressed in Chinese Hamster Ovary Cells," *Biochemistry*, 30(9), 2395–2406 (1991).

Spellman et al., "Carbohydrate Structure of Human Tissue Plasminogen Activator Expressed in Chinese Hamster Ovary Cells," *J. of Biol. Chem.*, 264(24), 14100–14111 (Aug. 26, 1989).

Srinivas et al., "Membrane Association and Defective Transport of Spleen Focus–forming Virus Glycoproteins," *J. Biol. Chem.*, 258, 14718–14724 (1983).

Stanley, "Surface Carbohydrate Alterations of Mutant Mammalian Cells Selected for Resistance to Plant Lectins," *The Biochemistry of Glycoproteins and Proteoglycans*, Chapter 4: 161–189, Lennarz ed., Plenum Press (1980).

Steck et al., "Cell Surface Properties of Spontaneously Metastasizing Rat Mammary Adenocarcinoma Cell Clones," *Transplantation Proceedings*, 16, 355–360 (1984).

Storring et al., "The International Standard for Recombinant DNA derived Erythropoietin: Collaborative Study of four recombinant DNA derived erythropoietins and two highly purified human urinary erythropoietins," *J. of Endo., 134, 459–84 (1992)/*

Strickland, "Occurrence of Sulfate on the N-Linked Oligosaccharides of Human Erythropoietin," *J. of Cellular Biochemistry*, Suppl. 16D, Abstract No. P324 (1992).

Sue et al., "Site–specific antibodies to human erythropoietin directed toward the NH$_2$–terminal region," *Proc. Nat. Acad. Sci. (USA)*, 80, 3651–3655 (1983).

Suggs et al., "Use of Synthetic Oligodeoxyribonucleotide for the Isolation of Specific Cloned DNA Sequences," *Developmental Biology Using Purified Genes*, 683–693 (D. Brown, Ed., 1981).

Suggs et al., "Use of synthetic oligonucleotides as hybridization probes:Isolation of cloned cDNA sequences for human B$_2$–microglobulin," *P.N.A.S. (USA)*, 78, 6613–6617 (1981).

Sveda et al., "Functional expression in primate cells of cloned DNA coding for the hemagglutinin surface glycoprotein of influenza virus," *Pros. Nat'l. Acad. Sci. (USA)*, 78(10):5488–5492 (Sep. 1981).

Sytowski et al., "The Biochemistry of Erythropoietin: An Approach to its mode of Action," *Exp. Hematol.*, 8(Supp. 8), 52–63 (1980).

Sytowski et al., "A Novel Radioimmunoassay for Human Erythropoietin Using a Synthetic NH$_2$–Terminal Polypeptide and Anti-Peptide Antibodies," *J. Immunol. Methods*, 69, 181–186 (1984).

Szostak et al., "Hybridization with Synthetic Oligonucleotides," *Meth. in Enzymol.*, 68, 419–428 (1979).

Takeuchi et al., "Relationship between sugar chain structure and biological activity of recombinant human erythropoietin produced in Chinese hamster ovary cells," *P.N.A.S. (USA)*, 86, 7819–7822 (Oct. 1989).

Takeuchi, "Comparative Study of the Asparagine–linked Sugar Chains of Human Erythropoietin Purified from Urine and the Culture Medium of Recombinant Chinese Hamster ovary Cells," *J. Biol. Chem.*, 263(8), 3657–3663 (Mar. 15, 1988).

Talmadge et al., "Eukaryotic Signal Sequence Transports Insulin Antigen in *Escherichia coli*," *P.N.A.S. USA* 77(6), 3369–3373 (Jun. 1980).

Tambourin et al., "Production of erythropoietin–like activity by a murine erythroleukemia cell line," *P.N.A.S. (USA)*, 80, 6269–6273 (1983).

Taniguchi et al., "Structure and expressin of a cloned cDNA coding for the hemagglutinin surface glycoprotein of influenza virus," *Nature*, 302:305–310 (24 Mar. 1983).

Taub et al., "An improved method for preparing large arrays of bacterial colonies containing plasmids for hybridization: in situ purification and stable binding of DNA on paper filters," *Chemical Abstracts*, 97(23), 164, Abstract No. 194002y (Dec. 12, 1982).

Taub et al., "An Improved Method for Preparing Large Arrays of Bacterial Colonies Containing Plasmids for Hybridization: In Situ Purification and Stable Binding of DNA on Paper Filters," *Anal. Biochem.*, 126, 222–230 (1982).

Testa et al., "Role of Purified Erythropoietin in the Amplification of the Erythroid Compartment," *Exp. Hematol.*, 8(Supp. 8), 144–152 (1980).

Tong et al., "The Formation of Erythrocyte Membrane Proteins during Erythropoietin–induced Differentiation," *J. Biol. Chem.*, 256(24), 12666–12672 (Dec. 25, 1981).

Toole et al., "Molecular cloning of a cDNA encoding human antihaemophilic factor," *Nature*, 312, 342–347 (Nov. 8, 1984).

Tramontario et al., "Statistical evaluation of the coding capacity of complementary DNA strands," *Nucleic Acids Research*, 12(12), 5049–5059 (1984).

Tsuda et al., "Comparative Structural Study of N-Linked Oligosaccharides of Urinary and Recombinant Erythropoietins" *J. Amer. Chem. Soc.*, 27(15), 5646–5654 (1988).

Udupa et al., "Erythropoiesis in the aged mouse," *J. Lab. Clin. Med.*, 103(4), 574–580 & 581–588 (1984).

Ullrich et al., "Rat Insulin Genes: Construction of Plasmids Containing the Coding Sequences," *Science*, 196, 1313–1319 (Jun. 17, 1977).

Ullrich et al., "Isolation of the Human Insulin–like Growth Factor I Gene Using a Single Synthetic DNA Probe," *EMBO J.*, 3(2):361–364 (1984).

Ullrich et al., "Human epidermal growth factor receptor cDNA sequence and aberrant expression of the amplified gene in A431 epidermoid carcinoma cells," *Nature*, 309, 418–425 (May 31, 1984).

Ullrich et al., "Insulin–like growth factor I receptor primary structure: comparison with insulin receptor suggests structural determinants that define functional specificity," *EMBO J.*, 5(10), 2503–2512 (1986).

Ullrich et al., "Human insulin receptor and its relationship to the tyrosine kinase family of oncogenes," *Nature*, 313, 756–761 (Feb. 28, 1985).

Urabe et al., "The Influence of Steroid Hormone Metabolites on the In Vitro Development of Erythroid Colonies Derived from Human Bone Marrow," *J. Exp. Med.*, 149, 1314–1325 (Jun. 1979).

Urlaub et al., "Isolation of Chinese Hamster cell mutants deficient in dihydrofolate reductase activity," *Proc. Nat. Acad. Sci. (USA)*, vol. 77(7), 4216–4220 (Jul. 1980).

Van der Ploeg et al., "DNA Methylation in the Human $v\delta\beta$–Globin Locus in Erythroid and Noncrythroid Tissues," *Cell*, 19, 947–958 (Apr. 1980).

Van Stone et al., "Effect of erythropoietin on anemia of peritoneally dialyzed anephric rats," *Kidney Int'l.*, 15, 370–375 (1979).

Varki, "Diversity in the sialic acids," Oxford University Press, 25–40, (1992).

Vedovato et al., "Erythropoietin Levels in Heterozygous Beta–Thalassemia," *Acta. Haematol.*, 71, 211–213 (1984).

Vichinsky et al., "Inadequate erythroid response to hypoxia in cystic fibrosis," *J. Pediatr.*, 105(1), 15–21 (Jul. 1984).

Vieira et al., "The pUC plasmids, an M13mp7–derived system for insertion mutagenesis and sequencing with synthetic universal primers," *Gene*, 19, 259–268 (1982).

Villasante et al., "Binding of microtubule protein to DNA and chromatin: possibility of simultaneous linkage of microtubule to nucleic acid and assembly of the microtubule structure," *Nucleic Acids Res*, 9(4), 895 (1981).

Walker et al., *Techniques in Molecular Biology*, Macmillan Pub. Co., N.Y., p. 280 (1983).

Wallace et al., "Hybridization of synthetic oligodeoxyribonucleotides to Phi–chi 174 DNA: the effect of single base pair mismatch," *Nuc. Acids Res.*, 6(11), 3543–3557 (1979).

Wallace et al., "Directed Deletion of a Yeast Transfer RNA Intervening Sequence," *Science*, 209:1396–1400 (Sep. 19, 1980).

Wallace et al., "Oligonucleotide Directed Mutagenesis of the Human $\beta$–globin gene: A General Method for Producing Specific Point Mutations in cloned DNA," *Nucleic Acids Research*, 9(15):3647–3657 (1981).

Wallace et al., "The use of synthetic oligonucleotides as hybridization probes. II. Hybridization of oligonucleotides of mixed sequence to rabbit $\beta$–globin DNA," *Nuc. Acids Res.*, 9(4), 879–894 (1981).

Wallace et al., "A set of synthetic oligodeoxyribonucleotide primers for DNA sequencing in the plasmid vector pBR322," *Gene*, 16, 21–26 (1981).

Wallis et al., "The isolation of cDNA clones for human apolipoprotein E and the detection of apoE RNA in hepatic and extra–hepatic tissues," *EMBO J.*, 2, 2369–2373 (1983).

Walter et al., "Antibodies specific for the carboxy– and amino–terminal regions of simian virus 40 large tumor antigen," *P.N.A.S. (USA)*, 77(9), 5197–5200 (Sep. 1980).

Walter et al., "Antibodies specific for the polyoma virus middle–size tumor antigen," *P.N.A.S. (USA)*, 78, 4882–4886 (Aug. 1981).

Wang et al., "Some Chemical Properties of Human Erythropoietin", *Endocrinology*, 116(6), 2286–2292 (1985).

Wang et al., "Renal and extrarenal erythropoietin production in male and female rats of various ages," *J. Lab. Clin. Med.*, 79(2), 181–186 (Feb. 1972).

Weiland et al., "In vivo Activity of Asialo–Erythropoietin in Combination with Asialo–Glycoproteins," *Blut*, 44(3), 173–175 (1982).

Weiss et al., "Characterization of a monoclonal antibody to human erythropoietin," *P.N.A.S. (USA)*, 79, 5465–5469 (1982).

Weiss et al., "Studies of the pathogenesis of anemia of inflammation: Mechanism of impaired erythropoiesis," *Am. J. Vet. Res.*, 44(10), 1832–1835 (Oct. 1983).

Weissman et al., "Structure and expression of human IFN–$\alpha$ Genes," *Phil. Trans. R. Soc. Lond.*, B299, 7–28 (1982).

White et al., "Studies on Erythropoietin," *Recent Progr. Hormone Res.*, 16:219–262 (1960).

White et al., "Haemagglutinin of influenza virus expressed from a cloned gene promotes membrane fusion," *Nature*, 300, 658–659 (1982).

Whitehead et al., "Use of a cDNA Clone for the Fourth Component of Human Complement (C4) for Analysis of a Genetic Deficiency of C4 in Guinea Pig", *PNAS (USA)*, 80:5387–5391 (Sep. 1983).

Wiaderkiewicz et al., "Mismatch and blunt to protruding–end joining by DNA ligases," *Nucleic Acids Res*, 15(19), 7831–7848 (1987).

Wickens et al., "Expression of a chicken chromosomal ovalbumin gene injected into frog oocyte nuclei," *Nature* 285:628–634 (26 Jun. 1980).

Wide et al., "Molecular charge heterogeneity of human serum erythropoietin," *British J. Haemat.*, 76, 121–127 (1990).

Wiktor et al., "Protection from rabies by a vaccinia virus recombinant containing the rabies virus glycoprotein gene," *Proc. Nat'l. Acad. Sci. (USA)*, 81, 7194–7198 (1984).

Wong et al., "Synthetic peptide fragment of src gene product inhibits the src protein kinase and crossreacts immunologically with avian one kinases and cellular phosphoproteins," *P.N.A.S. (USA)*, 78(12), 7412–7416 (Dec. 1981).

Wong et al., "Interferon–$\gamma$ Induces Enhanced Expression of Ia And H–2 Antigens on B Lymphoid, Macrophage, and Myeloid Cell Lines," *J. Immun.*, 131 (2):788–793 (Aug. 1983).

Woo, "A Sensitive and Rapid Method for Recombinant Phage Screening," *Methods in Enzymology*, 68, 389–395 (1979).

Wood et al., "Expression of active human factor VIII from recombinant DNA clones," *Nature*, 312, 330–336 (Nov. 22, 1984).

Woods et al., "Isolation of a cDNA Clone Corresponding to the MHC Linked Complement Protein Factor B," *Mol. Immunology*, 19, 1411 (1982).

Woods et al., "Isolation of cDNA clones for the human complement protein factor B, a class III major histocompatability complex gene product," *P.N.A.S. USA* 79, 5661–5665 (Sep. 1982).

Woods et al., "Isolation of Class III cDNA Clones," *Second Meeting on Cloning of the HLA and H 2 Regions, Abstract* (Apr. 17–19, 1983).

Yanagawa et al., "Hybridomas for Production of Monoclonal antibodies to Human Erythropoetin," *Blood*, 64(2), 357–364 (Aug. 1984).

Yanagawa et al., "Isolation of Human Erythropoietin with Monoclonal Antibodies," *J. Biol. Chem.*, 259(5), 2707–2710 (Mar. 10, 1984).

Yanagi, "Recombinant Human Erythropoietin Produced by Namalwa Cells," *DNA*, 8(6), 419–427 (1989).

Young et al., "Efficient isolation of genes by using antibody probes," *P.N.A.S.* 80, 1194–1198 (Mar. 1983).

Yuen et al., "The Spectrum of N–linked oligosaccharide structures detected by enzymic microsequencing on a recombinant soluble CD4 glycoprotein from Chinese hamster ovary cells," *Eur. J. Biochem.*, 192, 523–528 (1990).

Zinn et al., "Regulated expression of an extrachromosomal human β–interferon gene in mouse cells," *P.N.A.S. (USA)*, 79, 4897–4901 (Aug. 1982).

FIG. 5A

```
Sau3A
GATCCCGCGCCCCCTGGACAGCCGCGCCCTCTCCTCCAGGCCCGTGGGCGTGGCCCTGCCC
CGCTGAACTTCCCGGGATGAGGACTCCCGGTGTGGTCACCGCGCCTAGGTCGCTGAG

-27                                     -20
                                            Met Gly Val His Glu Cys Pro Ala Trp
GGACCCCGGCCAGGGCGCGGAGATG                   ATG GGG GTG CAC GAA TGT CCT GCC TGG

-10
Leu Trp Leu Leu Ser Leu Val Ser Leu Pro Leu Gly Leu Pro
CTG TGG CTT CTC CTG TCT CTC GTG TCG CTC CCT CTG GGC CTC CCA

-1  +1                                              10
Val Pro Gly Ala Pro Pro Arg Leu Ile Cys Asp Ser Arg Val Leu
GTC CCG GGC GCC CCA CCA CGC CTC ATC TGT GAC AGC CGA GTC CTG

20                       *
Glu Arg Tyr Leu Leu Glu Ala Lys Glu Ala Glu Asn Val Thr Met
GAG AGG TAC CTC TTG GAG GCC AAG GAG GCC GAG AAT GTC ACG ATG

30                             *           40
Gly Cys Ser Glu Ser Cys Ser Leu Asn Glu Asn Ile Thr Val Pro
GGC TGT TCC GAA AGC TGC AGC TTG AAT GAG AAT ATC ACC GTC CCA
```

FIG.5B

```
Asp Thr Lys Val Asn Phe Tyr Ala Trp Lys Arg Met Glu Val Gly
GAC ACC AAA GTT AAC TTC TAT GCC TGG AAG AGG ATG GAG GTC GGG
                            50                      70
Gln Gln Ala Val Glu Val Trp Gln Gly Leu Ala Leu Leu Ser Glu
CAG CAG GCT GTA GAA GTC TGG CAG GGC CTG GCC CTG CTC TCA GAA
         60                                  *
Ala Val Leu Arg Gly Gln Ala Val Leu Ala Asn Ser Ser Gln Pro
GCT GTC CTG CGG GGC CAG GCC GTG TTG GCC AAC TCT TCC CAG CCT
                            80                      100
Phe Glu Pro Leu Gln Leu His Met Asp Lys Ala Ile Ser Gly Leu
TTC GAG CCC CTG CAG CTG CAC ATG GAT AAA GCC ATC AGT GGC CTT
         90                                 
Arg Ser Ile Thr Thr Leu Leu Arg Ala Leu Gly Ala Gln Glu Ala
CGC AGC ATC ACC ACT CTG CTT CGG GCG CTG GGA GCC CAG GAA GCC
                           110                      130
Ile Ser Leu Pro Asp Ala Ala Ser Ala Ala Pro Leu Arg Thr Ile
ATC TCC CTC CCA GAT GCC GCG TCG GCT GCT CCA CTC CGA ACC ATC
        120
Thr Ala Asp Thr Phe Cys Lys Leu Phe Arg Val Tyr Ser Asn Phe
ACT GCT GAC ACT TTC TGC AAA CTC TTC CGA GTC TAC TCC AAT TTC
                           140
```

FIG. 5C

```
         150                                            160
Leu Arg Gly Lys Leu Tyr Thr Gly Glu Ala Cys Arg Arg
CTC CGG GGA AAG CTG AAG CTG TAC ACG GGG GAG GCC TGC AGG AGA

165
Gly Asp Arg OP
GGG GAC AGA TGA  CCAGGTGCGTCCAGCTGGGCACATCCACCACCTCCCTCACCAACA

CTGCCCTGTGCCACACCCCTCCCTCACCACTCCAGTGCCAGCAATGACATCTCAGGGCCAGAGGAAC

CGCCAGCCTGTCCCATGGACACTCTGAGATCTAAGGATGTCGCAGGCCAACTTGAGGGCCCAGAGC

TGTCCAGAGCACAACTCTGAGATCTAAGGATGTCGCAGGCCAACTTGAGGGCCCAGAGC

AGGAAGCATTCAGAGAGCAGCTTTAAACTCAGGAGCAGAGACAATGCAGGGAAAACACCT

GAGCTCACTCGGCCACCTGCAAAATTTGATGCAGGACACGCTTTGGAGGCAATTTACCTG

TTTTTGCACCTACCATCAGGAGGACAGGATGACTGGAGAACTTAGGTGGCAAGCTGTGACTT

CTCAAGGCCCTCACGGGCCACTCCCTTGGTGGCAAGAGCCCCCTTGACACTGAGAGAATATT

TTGCAATCTGCAGCAGGAAAATTACGGACAGGTTTTGGAGGTTGGAGGTACTTGACAG

GTGfGTGGGAAGCAGGGCGJAGGGGTGGAGCTGGGAGfGAGAACCGTGAAGAC

AGGATGGGGGCTGGCCCTCTGGTTCTCGTGGGGTCCAAGCTT
                                    HindIII
```

FIG.6A

```
AAGCTTCTGGGCTTCCAGACCCAGCTACTTTGCGGAACTCAGCAACCCAGGCATCTCTGAGTCTTCCGCCCA

AGACCGGGATGCCCCCAGGGGAGGTGTCCGGGAGCCCAGCCTTTCCCAGATAGCACGCTCCGCCAGTCCC

AAGGGGTGCGCAACCGGCTGCACTCCCCGCGACCCAGGGCCCGGAGCAGCCCCCATGACCCACACGC

ACGTCTGCAGCAGCCCCCGCTCACGCACCCAGGCGTCCTGCCCCTGCTCTGACCCCGG

GTGGCCCCTACCCCCTGGCGACCCCCTCACGCACACAGCCCTCTCCCCACCCCGCACGCACACATG

CAGATAACAGCCCCGACCCCCGGCCAGAGCCGXAGAGTCCCTGGGCCACCCCGGCCCTGCGCTG

CGCCGCACCGCGCTGTCCTCCCGGAGCCGACCGGGCCCCXGCTCTGCTCCGACACCGCGCCC

CTTGGACAGCCCGCCCCTCTCCTCCTCTAGGCCCGTGGGGCTGGCCCGAGCTTCCCGGGATGAGGXX

-27      -24
                                                 Met Gly Val His
CCCGGTGACCGGCGCGCCCAAGTCGCTGAGGGACCCCGGCCAAGCGCGGAG ATG GGG GTG CAC G

GTGAGTACTCGCGCTCCCGGCGCTCCCGGCGGGTTCCTGTTTGAGCGGGATTTAGCGCCCCGGCT
```

FIG. 6B

```
ATTGGCCAAGAGAGTTGGCTGGGTTCAAGGACCGGCGACTTGTCAAGGACCCCGGAAGGGGAGGGGGTGGG

GCAGCCTCCACGTGCCGCGGGACTTGGGGAGTTCTTGGGGATGCAAAAACCTGGCCTGTTGAGGGGCA

CAGTTTGGGGTTGGGGAGGAGTTTGGGGTTCTGCTGTGTGCAGTTGTGTCGTTGTCAGTGTCTCG[I.S.]

TTGCACACGCACAGATCAATAAGCCAGAGGCAGCACCTGAGTGCTTGCATGGTTGGGACAGGAAGGACGAG

CTGGGGGCAGAGACGTGGGGGATGAAGGAAGCTGTCCTTCCCACAGCCACCCTTCTCCCCCCGCCTGACTCT
                          -23  -20
                          Glu Cys Pro Ala Trp Leu Trp Leu Leu Ser Leu
CAGCCTGGCTATCTGTTCTAG     AA  TGT CCT GCC TGG CTG TGG CTT CTC CTG TCC CTG
                                                      -1  +1
       -10                                    Leu Gly Ala Pro Pro Arg Leu Ile Cys
Leu Ser Leu Pro Leu Gly Leu Pro Val Leu Pro Val Leu Pro
CTG TCG CTT CCT CTG GGC CTC CCA GTC CTG GGC GCC CCA CCA CGC CTC ATC TGT
            10                                         20                *
Asp Ser Arg Val Leu Glu Arg Tyr Leu Leu Glu Ala Lys Glu Ala Glu Asn Ile
GAC AGC CGA GTC CTG GAG AGG TAC CTC TTG GAG GCC AAG GAG GCC GAG AAT ATC

26
Thr
ACG GTGAGACCCCTTCCCCAGCACATTCCACAGAACTCACGCTCAGGGCTTCAGGGAACTCCTCCCAGAT

CCAGGAACCTGGCACTTGGTTTGGGGTGGAGTTGGGAAGCTAGACACTGCCCCCCCTACATAAGAATAAGTC
```

FIG. 6C

TGGTGGCCCCCAAAACCATACCTGAAACTAGGCAAGGAGCAAAGCCAGCAGATCCTACGCCTGTGGCCAGGG

```
                                          27                    30
                                          Thr Gly Cys Ala Glu
                                          ACG GGC TGT GCT GAA
```

CCAGAGCCTTCAGGGACCCCTTGACTCCCCCGGGCTGTGTGCATTTCAG

```
                           *       40
His Cys Ser Leu Asn Glu Asn Ile Thr Val Pro Asp Thr Lys Val Asn Phe Tyr
CAC TGC AGC TTG AAT GAG AAT ATC ACT GTC CCA GAC ACC AAA GTT AAT TTC TAT 50                       55
Ala Trp Lys Arg Met Glu
GCC TGG AAG AGG ATG GAG  GTGAGTTCCTTTTTTTTTTCCTTTCTTTTGGAGAATCTCATT
```

TGCGAGCCTGATTTGGATGAAAGGGAGAATGATCGGGGAAAAGGTAAAATGGAGCAGCAGAGATGAGGCT

GCCTGGGGCGCAGAGGCTCACGTCTCTATAATCCCAGGCTGAGATGGGCCGAGATGGGAGAATTGCTTGAGCCCT

GGAGTTTCAGACCAACCTAGGCAGCATAGTGAGATCCCCATCTCTACAAACATTTAAAAAAATTAGTCAG

GTGAAGTGGTGCATGGTGGTAGTCCCAGATATTTGGAAGGCTGAGGCGGGAGGATCGCTTGAGCCCAGGAA

TTTGAGGCTGCAGTGAGCTGTGATCACACCACTGCACTCCAGCCTCAGTGACAGAGTGAGGCCCTGTCTCA

FIG. 6D

```
AAAAAGAAAAAGAAAAAGAAAAATAATGAGGGCTGTATGGAATACATTCATTATTCATTCACTCACTCACT
CACTCATTCATTCATTCATTCAACAAGTCTTATTGCATACCTTCTGTTTGCTCAGCTTGGTGTGCTTGG
GGCTGCTGAGGGGCAGGAGGGGAGAGGGTGACATGGGTCAGCTCGACTCCCCAGAGTCCACTCCCTGTAG
```

```
       56                                                      70
       Val Gly Gln Gln Ala Val Glu Val Trp Gln Gly Leu Ala Leu Leu Ser Glu Ala
       GTC GGG CAG CAG GCC GTA GAA GTC TGG CAG GGC CTG GCC CTG CTG TCG GAA GCT

80              *                          90
       Val Leu Arg Gly Gln Ala Leu Leu Val Asn Ser Ser Gln Pro Trp Glu Pro Leu
       GTC CTG CGG GGC CAG GCC CTG TTG GTC AAC TCT TCC CAG CCG TGG GAG CCC CTG

100
       Gln Leu His Val Asp Lys Ala Val Ser Gly Leu Arg Ser Leu Thr Thr Leu Leu
       CAG CTG CAT GTG GAT AAA GCC GTC AGT GGC CTT CGC AGC CTC ACC ACT CTG CTT 110                        115
       Arg Ala Leu Gly Ala Gln
       CGG GCT CTG GGA GCC CAG GTGAGTAGGAGCGGGACACTTCTGCCCTTTCTGTAAGAAGGGGA
GAAGGGGTCTTGCTAAGGAGTACAGGAACTGTCCGTATTCCTTCCCCTTTCTGTGGCACTGCAGGACCTCCT
```

```
       116                                 120
       Lys Glu Ala Ile Ser Pro Pro Asp Ala Ala Ser Ala Ala
       AAG GAA GCC ATC TCC CCT CCA GAT GCG GCC TCA GCT GCT
GTTTTCTCCTTGGCAG
```

FIG. 6E

```
                130                              140
Pro Arg Thr Ile Thr Ala Asp Thr Phe Arg Lys Leu Phe Arg Val Tyr Ser
CCA CTC CGA ACA ATC ACT GCT GAC ACT TTC CGC AAA CTC TTC CGA GTC TAC TCC

160
Asn Phe Leu Arg Gly Lys Leu Lys Leu Tyr Thr Gly Glu Ala Cys Arg Thr Gly
AAT TTC CTC CGG GGA AAG CTG AAG CTG TAC ACA GGG GAG GCC TGC AGG ACA GGG

166
Asp Arg OP
GAC AGA TGA CCAGGTGTGTCCACCTGGGCATATCCACCACCTCCCTCACCAACATTGCTTGTGCCACA

CCCTCCCCCGCCACTCCTGAACCCCGTCGAGGGGCTCTCAGCTCCCAGCGCCAGCCTGTCCCATGGACACTCC

AGTGCCAGCAATGACATCTCAGGGGCCAGAGGAACTGTCCAGAGAGCAACTCTGAGATCTAAGGATGTCAC

AGGGCCAACTTGAAGGGCCCAGAGCAGGAAGCATTCAGAGAGCAGCTTTAAACTCAGGGACAGAGCCATGC

TGGGAAGACGCCTGAGCTCACTCGGCACCCTGCAAAATTTGATGCCAGGACACGCTTTGGAGGCGATTTAC

CTGTTTTCGCACCTACCATCAGGGACAGGATGACCTGGAGAACTTAGGTGGCAAGCTGTGACTTCTCCAGG

TCTCACGGGCATGGGCACTCCCCTTGGCTCTCATGGGGTCCAAGTTTTGTGTATTCTCAACCTATTGACAGACTGAA

AXGATXGGGGCTGGCCTCTGGCCTCTCAACCTATTGACAGACTGAA

ACACAATATGAC
```

FIG. 7

```
                                            -1   1
     XbaI                                      MetAla
     CTAG AAACCATGAG GGTAATAAAA TAATGGCTCC GCCGCGTCTG
          TTTGGTACTC CCATTATTTT ATTACCGAGG CGGCGCAGAC

ATCTGCGACT CGAGAGTTCT GGAACGTTAC CTGCTGGAAG CTAAAGAAGC
TAGACGCTGA GCTCTCAAGA CCTTGCAATG GACGACCTTC GATTTCTTCG

TGAAAACATC ACCACTGGTT GTGCTGAACA CTGTTCTTTG AACGAAAACA
ACTTTTGTAG TGGTGACCAA CACGACTTGT GACAAGAAAC TTGCTTTTGT

TTACGGTACC AGACACCAAG GTTAACTTCT ACGCTTGGAA ACGTATGGAA
AATGCCATGG TCTGTGGTTC CAATTGAAGA TGCGAACCTT TGCATACCTT

GTTGGTCAAC AAGCAGTTGA AGTTTGGCAG GGTCTGGCAC TGCTGAGCGA
CAACCAGTTG TTCGTCAACT TCAAACCGTC CCAGACCGTG ACGACTCGCT

GGCTGTACTG CGTGGCCAGG CACTGCTGGT AAACTCCTCT CAGCCGTGGG
CCGACATGAC GCACCGGTCC GTGACGACCA TTTGAGGAGA GTCGGCACCC

AACCGCTGCA GCTGCATGTT GACAAAGCAG TATCTGGCCT GAGATCTCTG
TTGGCGACGT CGACGTACAA CTGTTTCGTC ATAGACCGGA CTCTAGAGAC

ACTACTCTGC TGCGTGCTCT GGGTGCACAG AAAGAGGCTA TCTCTCCGCC
TGATGAGACG ACGCACGAGA CCCACGTGTC TTTCTCCGAT AGAGAGGCGG

GGATGCTGCA TCTGCTGCAC CGCTGCGTAC CATCACTGCT GATACCTTCC
CCTACGACGT AGACGACGTG GCGACGCATG GTAGTGACGA CTATGGAAGG

GCAAACTGTT TCGTGTATAC TCTAACTTCC TGCGTGGTAA ACTGAAACTG
CGTTTGACAA AGCACATATG AGATTGAAGG ACGCACCATT TGACTTTGAC

SalI
TATACTGGCG AAGCATGCCG TACTGGTGAC CGCTAATAG
ATATGACCGC TTCGTACGGC ATGACCACTG GCGATTATCA GCT
```

FIG. 8

```
           -1 +1
HindIII    ArgAla
AGCTTGGATA AAAGAGCTCC ACCAAGATTG ATCTGTGACT CGAGAGTTTT
     ACCTAT TTTCTCGAGG TGGTTCTAAC TAGACACTGA GCTCTCAAAA GGAAAGATAC TTGTTGGAAG CTAAAGAAGC TGAAAACATC ACCACTGGTT
CCTTTCTATG AACAACCTTC GATTTCTTCG ACTTTTGTAG TGGTGACCAA GTGCTGAACA CTGTTCTTTG AACGAAAACA TTACGGTACC AGACACCAAG
CACGACTTGT GACAAGAAAC TTGCTTTTGT AATGCCATGG TCTGTGGTTC GTTAACTTCT ACGCTTGGAA ACGTATGGAA GTTGGTCAAC AAGCTGTTGA
CAATTGAAGA TGCGAACCTT TGCATACCTT CAACCAGTTG TTCGACAACT AGTTTGGCAA GGTTTGGCCT TGTTATCTGA AGCTGTTTTG AGAGGTCAAG
TCAAACCGTT CCAAACCGGA ACAATAGACT TCGACAAAAC TCTCCAGTTC CCTTGTTGGT TAACTCTTCT CAACCATGGG AACCATTGCA ATTGCACGTC
GGAACAACCA ATTGAGAAGA GTTGGTACCC TTGGTAACGT TAACGTGCAG GATAAAGCCG TCTCTGGTTT GAGATCTTTG ACTACTTTGT TGAGAGCTTT
CTATTTCGGC AGAGACCAAA CTCTAGAAAC TGATGAAACA ACTCTCGAAA GGGTGCTCAA AAGGAAGCCA TTTCCCCACC AGACGCTGCT TCTGCCGCTC
CCCACGAGTT TTCCTTCGGT AAAGGGGTGG TCTGCGACGA AGACGGCGAG CATTGAGAAC CATCACTGCT GATACCTTCA GAAAGTTATT CAGAGTTTAC
GTAACTCTTG GTAGTGACGA CTATGGAAGT CTTTCAATAA GTCTCAAATG TCCAACTTCT TGAGAGGTAA ATTGAAGTTG TACACCGGTG AAGCCTGTAG
AGGTTGAAGA ACTCTCCATT TAACTTCAAC ATGTGGCCAC TTCGGACATC AACTGGTGAC AGATAAGCCC GACTGATAAC AACAGTGTAG
TTGACCACTG TCTATTCGGG CTGACTATTG TTGTCACATC SalI
ATGTAACAAA G
TACATTGTTT CAGCT
```

FIG. 9

```
             -20          -10           +1           10           20           30           40
Human    MGVHECPAWLWLLLSLLSLPLGLPVLGAPPRLICDSRVLERYLLEAKEAENITTGCAEHCSLNENITVPDTK
         ***************   *************************      *  *    *************
Monkey   MGVHECPAWLWLLLSLVSLPLGLPVPGAPPRLICDSRVLERYLLEAKEAENVTMGCSESCSLNENITVPDTK 50           60           70           80           90          100          110
Human    VNFYAWKRMEVGQQAVEVWQGLALLSEAVLRGQALLVNSSQPWEPLQLHVDKAVSGLRSLTTLLRALGAQKE
         ****************************** *    *************  ***  ****  ********  *
Monkey   VNFYAWKRMEVGQQAVEVWQGLALLSEAVLRGQAVLANSSQPFEPLQLHMDKAISGLRSITTLLRALGAQ-E 120          130          140          150          160
Human    AISPPDAASAAPLRTITADTFRKLFRVYSNFLRGKLKLYTGEACRTGDR
         *** *************************  ********************
Monkey   AISLPDAASAAPLRTITADTFCKLFRVYSNFLRGKLKLYTGEACRRGDR
```

FIG. 10

1. AATTCTAGAAACCATGAGGGTAATAAAATA
2. CCATTATTTTATTACCCTCATGGTTTCTAG
3. ATGGCTCCGCCGCGTCTGATCTGCGAC
4. CTCGAGTCGCAGATCAGACGCGGCGGAG
5. TCGAGAGTTCTGGAACGTTACCTGCTG
6. CTTCCAGCAGGTAACGTTCCAGAACT
7. GAAGCTAAAGAAGCTGAAAACATC
8. GTGGTGATGTTTTCAGCTTCTTTAG
9. ACCACTGGTTGTGCTGAACACTGTTC
10. CAAAGAACAGTGTTCAGCACAACCA
11. TTTGAACGAAAACATTACGGTACCG
12. GATCCGGTACCGTAATGTTTTCGTT

FIG. 11

```
        XbaI
EcoRI              1                              3
AATTCTAG AAACCATGAG GGTAATAAAA TAATGGCTCC GCCGCGTCTG
    GATC TTTGGTACTC CCATTATTTT ATTACCGAGG CGGCGCAGAC
                        2                              4

5
ATCTGCGACT CGAGAGTTCT GGAACGTTAC CTGCTGGAAG CTAAAGAAGC
TAGACGCTGA GCTCTCAAGA CCTTGCAATG GACGACCTTC GATTTCTTCG
                              6

7                   9                   11
TGAAAACATC ACCACTGGTT GTGCTGAACA CTGTTCTTTG AACGAAAACA
ACTTTTGTAG TGGTGACCAA CACGACTTGT GACAAGAAAC TTGCTTTTGT
       8                      10

0
    KpnI    BamHI
TTACGGTACC G
AATGCCATGG CCTAG
    12
```

FIG. 12

1. AATTCGGTACCAGACACCAAGGT
2. GTTAACCTTGGTGTCTGGTACCG
3. TAACTTCTACGCTTGGAAACGTAT
4. TTCCATACGTTTCCAAGCGTAGAA
5. GGAAGTTGGTCAACAAGCAGTTGAAGT
6. CCAAACTTCAACTGCTTGTTGACCAAC
7. TTGGCAGGGTCTGGCACTGCTGAGCG
8. GCCTCGCTCAGCAGTGCCAGACCCTG
9. AGGCTGTACTGCGTGGCCAGGCA
10. GCAGTGCCTGGCCACGCAGTACA
11. CTGCTGGTAAACTCCTCTCAGCCGT
12. TTCCACGGCTGAGAGGAGTTTACCA
13. GGGAACCGCTGCAGCTGCATGTTGAC
14. GCTTTGTCAACATGCAGCTGCAGCGG
15. AAAGCAGTATCTGGCCTGAGATCTG
16. GATCCAGATCTCAGGCCAGATACT

FIG. 13

```
EcoRI KpnI        1                              3
A ATTCGGTACC AGACACCAAG GTTAACTTCT ACGCTTGGAA ACGTATGGAA
  GCCATGG TCTGTGGTTC CAATTGAAGA TGCGAACCTT TGCATACCTT
        2                                     4

7
GTTGGTCAAC AAGCAGTTGA AGTTTGGCAG GGTCTGGCAC TGCTGAGCGA
CAACCAGTTG TTCGTCAACT TCAAACCGTC CCAGACCGTG ACGACTCGCT
     5                                          8
        6

11
GGCTGTACTG CGTGGCCAGG CACTGCTGGT AAACTCCTCT CAGCCGTGGG
CCGACATGAC GCACCGGTCC GTGACGACCA TTTGAGGAGA GTCGGCACCC
     9                                           12
       10

15    BglIII  BamHI
AACCGCTGCA GCTGCATGTT GACAAAGCAG TATCTGGCCT GAGATCTG
TTGGCGACGT CGACGTACAA CTGTTTCGTC ATAGACCGGA CTCTAGACCTAC
   13                                          16
       14
```

FIG. 14

1. GATCCAGATCTCTGACTACTCTGC
2. ACGCAGCAGAGTAGTCAGAGATCTG
3. TGCGTGCTCTGGGTGCACAGAAGAGG
4. GATAGCCTCTTTCTGTGCACCCAGAGC
5. CTATCTCCGCCGGATGCTGCATCT
6. CAGCAGATGCAGCATCCGGCGGAGA
7. GCTGCACCGCTGCGTACCATCACTG
8. ATCAGCAGTGATGGTACGCAGCGGTG
9. CTGATACCTTCCGCAAACTGTTTCG
10. ATACACGAAACAGTTTGCGGAAGGT
11. TGTATACTCAACTTCCTGCGTGGTA
12. CAGTTTACCACGCAGGAAGTTAGAGT
13. AACTGAAACTGTATACTGGCGAAGC
14. GGCATGCTTCGCCAGTATACAGTTT
15. ATGCCGTACTGGTGACCGCTAATAG
16. TCGACTATTAGCGGTCACCAGTAC

FIG. 15

```
BamHI BglII
GA TCCAGATCTCTG
   GTCTAGAGAC 1                    3                        5
ACTACTCTGC TGCGTGCTCT GGGTGCACAG AAAGAGGCTA TCTCTCCGCC
TGATGAGACG ACGCACGAGA CCCACGTGTC TTTCTCCGAT AGAGAGGCGG
       2                    4

7                   9
GGATGCTGCA TCTGCTGCAC CGCTGCGTAC CATCACTGCT GATACCTTCC
CCTACGACGT AGACGACGTG GCGACGCATG GTAGTGACGA CTATGGAAGG
       6                    8

11                  13
GCAAACTGTT TCGTGTATAC TCTAACTTCC TGCGTGGTAA ACTGAAACTG
CGTTTGACAA AGCACATATG AGATTGAAGG ACGCACCATT TGACTTTGAC
      10                   12

15              SalI
TATACTGGCG AAGCATGCCG TACTGGTGAC CGCTAATAG
ATATGACCGC TTCGTACGGC ATGACCACTG GCGATTATC AGCT
      14                   16
```

FIG. 16

1. AATTCAAGCTTGGATAAAAGAGCT
2. GTGGAGCTCTTTTATCCAAGCTTG
3. CCACCAAGATTGATCTGTGACTC
4. TCTCGAGTCACAGATCAATCTTG
5. GAGAGTTTTGGAAGATACTTGTTG
6. CTTCCAACAAGTATCTTTCCAAAAC
7. GAAGCTAAAGAAGCTGAAACATC
8. GTGGTGATGTTTTCAGCTTCTTTAG
9. ACCACTGGTTGTGCTGAACACTGTTC
10. CAAAGAACAGTGTTCAGCACAACCA
11. TTTGAACGAAAACATTACGGTACCG
12. GATCCGGTACCGTAATGTTTTCGTT

FIG. 17

```
EcoRI  HindIII 1
AATTCA AGCTTGGATA
    GT TCGAACCTAT
            2
```

```
                    3
AAAGAGCTCC ACCAAGATTG ATCTGTGACT CGAGAGTTTT
TTTCTCGAGG TGGTTCTAAC TAGACACTGA GCTCTCAAAA
                                 4
```

```
    5                        7
GGAAAGATAC TTGTTGGAAG CTAAAGAAGC TGAAAACATC ACCACTGGTT
CCTTTCTATG AACAACCTTC GATTCTTCG  ACTTTTGTAG TGGTGACCAA
    6                        8
```

```
        9              11       KpnI     BamHI
GTGCTGAACA CTGTTCTTTG AACGAAAACA TTACGGTACC G
CACGACTTGT GACAAGAAAC TTGCTTTTGT AATGCCATGG CCTAG
                                12
```

FIG. 18

1. AATTCGGTACCAGACACCAAGGT
2. GTTAACCTTGGTGTCTGGTACCG
3. TAACTTCTACGCTTGGAAACGTAT
4. TTCCATACGTTTCCAAGCGTAGAA
5. GGAAGTTGGTCAACAAGCAGTTGAAGT
6. CCAAACTTCAACTGCTTGTTGACCAAC
7. TTGGCAAGGTTTGGCCTTGTTATCTG
8. GCTTCAGATAACAAGGCCAAACCTTG
9. AAGCTGTTTTGAGAGGTGAAGCCT
10. AACAAGGCTTGACCTCTCAAAACA
11. TGTTGGTTAACTCTTCTCAACCATGGG
12. TGGTTCCATGGTTGAGAAGAGTTAACC
13. AACCATTGCAATTGCACGTCGAT
14. CTTTATCGACGTGCAATTGCAA
15. AAAGCCGTCTCTGGTTTGAGATCTG
16. GATCCAGATCTCAAACCAGAGACGG

FIG. 19

```
         KpnI

EcoRI     1
A ATTCGGTACC AGACACCAAG
      GCCATGG TCTGTGGTTC
              2

3                           5
GTTAACTTCT ACGCTTGGAA ACGTATGGAA GTTGGTCAAC AAGCTGTTGA
CAATTGAAGA TGCGAACCTT TGCATACCTT CAACCAGTTG TTCGACAACT
               4                               6

7                           9
AGTTTGGCAA GGTTTGGCCT TGTTATCTGA AGCTGTTTTG AGAGGTCAAG
TCAAACCGTT CCAAACCGGA ACAATAGACT TCGACAAAAC TCTCCAGTTC
               8                              10

11                          13
CCTTGTTGGT TAACTCTTCT CAACCATGGG AACCATTGCA ATTGCACGTC
GGAACAACCA ATTGAGAAGA GTTGGTACCC TTGGTAACGT TAACGTGCAG
              12                              14

15       BglII    BamHI
GATAAAGCCG TCTCTGGTTT GAGATCTG
CTATTTCGGC AGAGACCAAA CTCTAGACCTA G
              16
```

FIG. 20

1. GATCCAGATCTTTGACTACTTTGTT
2. TCTCAACAAAGTAGTCAAAGATCTG
3. GAGAGCTTTGGGTGCTCAAAAGGAAG
4. ATGGCTTCCTTTTGAGCACCCAAAGC
5. CCATTTCCCCACCAGACGCTGCTT
6. GCAGAAGCAGCGTCTGGTGGGAA
7. CTGCCGCTCCATTGAGAACCATC
8. CAGTGATGGTTCTCAATGGAGCG
9. ACTGCTGATACCTTCAGAAAGTT
10. GAATAACTTTCTGAAGGTATCAG
11. ATTCAGAGTTTACTCCAACTTCT
12. CTCAAGAAGTTGGAGTAAACTCT
13. TGAGAGGTAAATTGAAGTTGTACAC
14. ACCGGTGTACAACTTCAATTTACCT
15. CGGTGAAGCCTGTAGAACTGGT
16. CTGTCACCAGTTCTACAGGCTTC
17. GACAGATAAGCCCGACTGATAA
18. GTTGTTATCAGTCGGGCTTAT
19. CAACAGTGTAGATGTAACAAAG
20. TCGACTTTGTTACATCTACACT

FIG. 21

```
BamHI  BglII   1
GATC CAGATCTTTG ACTACTTTGT TGAGAGCTTT
     GTCTAGAAAC TGATGAAACA ACTCTCGAAA
                 2

3                        5
GGGTGCTCAA AAGGAAGCCA TTTCCCCACC AGACGCTGCT TCTGCCGCTC
CCCACGAGTT TTCCTTCGGT AAAGGGGTGG TCTGCGACGA AGACGGCGAG
     4                            6

7              9                        11
CATTGAGAAC CATCACTGCT GATACCTTCA GAAAGTTATT CAGAGTTTAC
GTAACTCTTG GTAGTGACGA CTATGGAAGT CTTTCAATAA GTCTCAAATG
          8              10                     12

13                       15
TCCAACTTCT TGAGAGGTAA ATTGAAGTTG TACACCGGTG AAGCCTGTAG
AGGTTGAAGA ACTCTCCATT TAACTTCAAC ATGTGGCCAC TTCGGACATC
                          14                     16

17                  19
AACTGGTGAC AGATAAGCCC GACTGATAAC AACAGTGTAG
TTGACCACTG TCTATTCGGG CTGACTATTG TTGTCACATC

SalI
ATGTAACAAA G
TACATTGTTT CAGCT
    20
```

5,618,698

PRODUCTION OF ERYTHROPOIETIN

This is a continuation of my U.S. patent application Ser. No. 07/113,179 filed Oct. 23, 1987, and issued as U.S. Pat. No. 5,441,868 on Aug. 15, 1995, which was a continuation of U.S. patent application Ser. No. 06/675,298 filed Nov. 30, 1984 and issued as U.S. Pat. No. 4,703,008 on Oct. 27, 1987, which was a continuation-in-part of U.S. patent application Ser. No. 06/655,841, filed Sep. 28, 1984, now abandoned, which was a continuation-in-part of U.S. patent application Ser. No. 06/582,185, filed Feb. 21, 1984, now abandoned, and which was a continuation-in-part of U.S. patent application Ser. No. 06/561,024, filed Dec. 13, 1983, now abandoned.

BACKGROUND

The present invention relates generally to the manipulation of genetic materials and, more particularly, to recombinant procedures making possible the production of polypeptides possessing part or all of the primary structural conformation and/or one or more of the biological properties of naturally-occurring erythropoietin.

A. Manipulation Of Genetic Materials

Genetic materials may be broadly defined as those chemical substances which program for and guide the manufacture of constituents of cells and viruses and direct the responses of cells and viruses. A long chain polymeric substance known as deoxyribonucleic acid (DNA) comprises the genetic material of all living cells and viruses except for certain viruses which are programmed by ribonucleic acids (RNA). The repeating units in DNA polymers are four different nucleotides, each of which consists of either a purine (adenine or guanine) or a pyrimidine (thymine or cytosine) bound to a deoxyribose sugar to which a phosphate group is attached. Attachment of nucleotides in linear polymeric form is by means of fusion of the 5' phosphate of one nucleotide to the 3' hydroxyl group of another. Functional DNA occurs in the form of stable double stranded associations of single strands of nucleotides (known as deoxyoligonucleotides), which associations occur by means of hydrogen bonding between purine and pyrimidine bases [i.e., "complementary" associations existing either between adenine (A) and thymine (T) or guanine (G) and cytosine (C)]. By convention, nucleotides are referred to by the names of their constituent purine or pyrimidine bases, and the complementary associations of nucleotides in double stranded DNA (i.e., A-T and G-C) are referred to as "base pairs". Ribonucleic acid is a polynucleotide comprising adenine, guanine, cytosine and uracil (U), rather than thymine, bound to ribose and a phosphate group.

Most briefly put, the programming function of DNA is generally effected through a process wherein specific DNA nucleotide sequences (genes) are "transcribed" into relatively unstable messenger RNA (mRNA) polymers. The mRNA, in turn, serves as a template for the formation of structural, regulatory and catalytic proteins from amino acids. This mRNA "translation" process involves the operations of small RNA strands (tRNA) which transport and align individual amino acids along the mRNA strand to allow for formation of polypeptides in proper amino acid sequences The mRNA "message" derived from DNA and providing the basis for the tRNA supply and orientation of any given one of the twenty amino acids for polypeptide "expression" is in the form of triplet "codons"—sequential groupings of three nucleotide bases. In one sense, the formation of a protein is the ultimate form of "expression" of the programmed genetic message provided by the nucleotide sequence of a gene.

"Promoter" DNA sequences usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

A focus of microbiological processing for the last decade has been the attempt to manufacture industrially and pharmaceutically significant substances using organisms which either do not initially have genetically coded information concerning the desired product included in their DNA, or (in the case of mammalian cells in culture) do not ordinarily express a chromosomal gene at appreciable levels. Simply put, a gene that specifies the structure of a desired polypeptide product is either isolated from a "donor" organism or chemically synthesized and then stably introduced into another organism which is preferably a self-replicating unicellular organism such as bacteria, yeast or mammalian cells in culture. Once this is done, the existing machinery for gene expression in the "transformed" or "transfected" microbial host cells operates to construct the desired product, using the exogenous DNA as a template for transcription of mRNA which is then translated into a continuous sequence of amino acid residues.

The art is rich in patent and literature publications relating to "recombinant DNA" methodologies for the isolation, synthesis, purification and amplification of genetic materials for use in the transformation of selected host organisms. U.S. Pat. No. 4,237,224 to Cohen, et al., for example, relates to transformation of unicellular host organisms with "hybrid" viral or circular plasmid DNA which includes selected exogenous DNA sequences. The procedures of the Cohen, et al. patent first involve manufacture of a transformation vector by enzymatically cleaving viral circular plasmid DNA to form linear DNA strands. Selected foreign ("exogenous" or "heterologous") DNA strands usually including sequences coding for desired product are prepared in linear form through use of similar enzymes. The linear viral or plasmid DNA is incubated with the foreign DNA in the presence of ligating enzymes capable of effecting a restoration process and "hybrid" vectors are formed which include the selected exogenous DNA segment "spliced" into the viral or circular DNA plasmid.

Transformation of compatible unicellular host organisms with the hybrid vector results in the formation of multiple copies of the exogenous DNA in the host cell population. In some instances, the desired result is simply the amplification of the foreign DNA and the "product" harvested is DNA. Note frequently, the goal of transformation is the expression by the host cells of the exogenous DNA in the form of large scale synthesis of isolatable quantities of commercially significant protein or polypeptide fragments coded for by the foreign DNA. See also, e.g., U.S. Pat. Nos. 4,264,731 (to Shine), 4,273,875 (to Manis), 4,293,652 (to Cohen), and European Patent Application 093,619, published Nov. 9, 1983.

The development of specific DNA sequences for splicing into DNA vectors is accomplished by a variety of techniques, depending to a great deal on the degree of "foreignness" of the "donor" to the projected host and the size of the polypeptide to be expressed in the host. At the risk of over-simplification, it can be stated that three alternative principal methods can be employed: (1) the "isolation" of double-stranded DNA sequence from the genomic DNA of the donor; (2) the chemical manufacture of a DNA sequence providing a code for a polypeptide of interest; and (3) the in vitro synthesis of a double-stranded DNA sequence by enzymatic "reverse transcription" of mRNA isolated from donor cells. The last-mentioned methods which involve formation of a DNA "complement" of mRNA are generally referred to as "cDNA" methods.

Manufacture of DNA sequences is frequently the method of choice when the entire sequence of amino acid residues of the desired polypeptide product is known. DNA manufacturing procedures of co-owned, co-pending U.S. patent application Ser. No. 483,451, by Alton, et al., (filed Apr. 15, 1983 and corresponding to PCT US83/00605, published Nov. 24, 1983 as WO83/04053), for example, provide a superior means for accomplishing such highly desirable results as: providing for the presence of alternate codons commonly found in genes which are highly expressed in the host organism selected for expression (e.g., providing yeast or E. coli "preference" codons); avoiding the presence of untranslated "intron" sequences (commonly present in mammalian genomic DNA sequences and mRNA transcripts thereof) which are not readily processed by procaryotic host cells; avoiding expression of undesired "leader" polypeptide sequences commonly coded for by genomic DNA and cDNA sequences but frequently not readily cleaved from the polypeptide of interest by bacterial or yeast host cells; providing for ready insertion of the DNA in convenient expression vectors in association with desired promoter/regulator and terminator sequences; and providing for ready construction of genes coding for polypeptide fragments and analogs of the desired polypeptides.

When the entire sequence of amino acid residues of the desired polypeptide is not known, direct manufacture of DNA sequences is not possible and isolation of DNA sequences coding for the polypeptide by a cDNA method becomes the method of choice despite the potential drawbacks in ease of assembly of expression vectors capable of providing high levels of microbial expression referred to above. Among the standard procedures for isolating cDNA sequences of interest is the preparation of plasmid-borne cDNA "libraries" derived from reverse transcription of mRNA abundant in donor cells selected as responsible for high level expression of genes (e.g., libraries of cDNA derived from pituitary cells which express relatively large quantities of growth hormone products). Where substantial portions of the polypeptide's amino acid sequence are known, labelled, single-stranded DNA probe sequences duplicating a sequence putatively present in the "target" cDNA may be employed in DNA/DNA hybridization procedures carried out on cloned copies of the cDNA which have been denatured to single stranded form. [See, generally, the disclosure and discussions of the art provided in U.S. Pat. No. 4,394,443 to Weissman, et al. and the recent demonstrations of the use of long oligonucleotide hybridization probes reported in Wallace, et al., *Nuc. Acids Res.*, 6, pp. 3543–3557 (1979), and Reyes, et al., *P.N.A.S. (U.S.A.)*, 79, pp. 3270–3274 (1982), and Jaye, et al., *Nuc. Acids Res.*, 11, pp. 2325–2335 (1983). See also, U.S. Pat. No. 4,358,535 to Falkow, et al., relating to DNA/DNA hybridization procedures in effecting diagnosis; published European Patent Application Nos. 0070685 and 0070687 relating to light-emitting labels on single stranded polynucleotide probes; Davis, et al., "A Manual for Genetic Engineering, Advanced Bacterial Genetics", Cold Spring Harbor Laboratory, Cold Spring Harbor, N.Y. (1980) at pp. 55–58 and 174–176, relating to colony and plaque hybridization techniques; and, New England Nuclear (Boston, Mass.) brochures for "Gene Screen" Hybridization Transfer Membrane materials providing instruction manuals for the transfer and hybridization of DNA and RNA, Catalog No. NEF-972.]

Among the more signficant recent advances in hybridization procedures for the screening of recombinant clones is the use of labelled mixed synthetic oligonucleotide probes, each of which is potentially the complete complement of a specific DNA sequence in the hybridization sample including a heterogeneous mixture of single stranded DNAs or RNAs. These procedures are acknowledged to be especially useful in the detection of cDNA clones derived from sources which provide extremely low amounts of mRNA sequences for the polypeptide of interest. Briefly put, use of stringent hybridization conditions directed toward avoidance of non-specific binding can allow, e.g., for the autoradiographic visualization of a specific cDNA clone upon the event of hybridization of the target DNA to that single probe within the mixture which is its complete complement. See generally, Wallace, et al., *Nuc. Acids Res.*, 9, pp. 879–897 (1981); Suggs, et al. *P.N.A.S. (U.S.A.)*, 78, pp. 6613–6617 (1981); Choo, et al., *Nature*, 299, pp. 178–180 (1982); Kurachi, et al., *P.N.A.S. (U.S.A.)*, pp. 6461–6464 (1982); Ohkubo, et al., *P.N.A.S. (U.S.A.)*, 80, pp. 2196–2200 (1983); and Kornblihtt, et al. *P.N.A.S. (U.S.A.)*, 80, pp. 3218–3222 (1983). In general, the mixed probe procedures of Wallace, et al. (1981), supra, have been expanded upon by various workers to the point where reliable results have reportedly been obtained in a cDNA clone isolation using a 32-member mixed "pool" of 16-base-long (16-mer) oligonucleotide probes of uniformly, varying DNA sequences together with a single 11-mer to effect a two-site "positive" confirmation of the presence of cDNA of interest. See, Singer-Sam, et al., *P.N.A.S. (U.S.A.)*, 80, pp. 802–806 (1983).

The use or genomic DNA isolates is the least common of the three above-noted methods for developing specific DNA sequences for use in recombinant procedures. This is especially true in the area of recombinant procedures directed to securing microbial expression of mammalian polypeptides and is due, principally to the complexity of mammalian genomic DNA. Thus, while reliable procedures exist for developing phage-borne libraries of genomic DNA of human and other mammalian species origins [See, e.g., Lawn, et al. *Cell*, 15, pp. 1157–1174 (1978) relating to procedures for generating a human genomic library commonly referred to as the "Maniatis Library"; Karn, et al., *P.N.A.S. (U.S.A.)*, 77, pp. 5172–5176 (1980) relating to a human genomic library based on alternative restriction endonuclease fragmentation procedure; and Blattner, et al., *Science*, 196, pp. 161–169 (1977) describing construction of a bovine genomic library] there have been relatively few successful attempts at use of hybridization procedures in isolating genomic DNA in the absence of extensive foreknowledge of amino acid or DNA sequences. As one example, Fiddes, et al., *J. Mol. and App. Genetics*, 1, pp. 3–18 (1981) report the successful isolation of a gene coding for the alpha subunit of the human pituitary glycoprotein hormones from the Maniatis Library through use of a "full length" probe including a complete 621 base pair fragment of a previously-isolated cDNA sequence for the alpha subunit. As another example, Das, et al., *P.N.A.S. (U.S.A.)*, 80, pp. 1531–1535 (1983) report isolation of human genomic clones for human HLA-DR using a 175 base pair synthetic oligonucleotide. Finally, Anderson, et al., *P.N.A.S. (U.S.A.)*, 60, pp. 6838–6842 (1983) report the isolation of genomic clone for bovine pancreatic trypsin inhibitor (BPTI) using a single probe 86 base pairs in length and constructed according to the known amino acid sequence of BPTI. The authors note a determination of poor prospects for isolating mRNA suitable for synthesis of a cDNA library due to apparent low levels of mRNA in initially targeted parotid gland and lung tissue sources and then address the prospects of success in probing a genomic library using a mixture of labelled probes, stating: "More generally, mixed-sequence oligodeoxynucleotide probes have been used to isolate protein genes of unknown sequence from cDNA libraries. Such probes are typically mixtures of 8–32 oligonucleotides, 14–17 nucleotides in length, representing every possible codon combination for a small stretch (5–6 residues) of amino acid sequence. Under stringent hybridization conditions that discriminate against incorrectly base-paired probes, these mixtures are capable of locating specific gene sequences in clone libraries of low-to-moderate complexity. Nevertheless, because of their short length and heterogeneity, mixed probes often lack the specificity required for probing sequences as complex as a mammalian genome. This makes such a method impractical for the isolation of mammalian protein genes when the corresponding mRNAs are unavailable." (Citations omitted).

There thus continues to exist a need in the art for improved methods for effecting the rapid and efficient isolation of cDNA clones in instances where little is known of the amino acid sequence of the polypeptide coded for and where "enriched" tissue sources of mRNA are not readily available for use in constructing cDNA libraries. Such improved methods would be especially useful if they were applicable to isolating mammalian genomic clones where sparse information is available concerning amino acid sequences of the polypeptide coded for by the gene sought.

B. Erythropoietin As A Polypeptide Of Interest

Erythropoiesis, the production of red blood cells, occurs continuously throughout the human life span to offset cell destruction. Erythropoiesis is a very precisely controlled physiological mechanism enabling sufficient numbers of red blood cells to be available in the blood for proper tissue oxygenation, but not so many that the cells would impede circulation. The formation of red blood cells occurs in the bone marrow and is under the control of the hormone, erythropoietin.

Erythropoietin, an acidic glycoprotein of approximately 34,000 dalton molecular weight, may occur in three forms: α, β and asialo. The α and β forms differ slightly in carbohydrate components, but have the same potency, biological activity and molecular weight. The asialo form is an α or β form with the terminal carbohydrate (sialic acid) removed. Erythropoietin is present in very low concentrations in plasma when the body is in a healthy state wherein tissues receive sufficient oxygenation from the existing number of erythrocytes. This normal low concentration is enough to stimulate replacement of red blood cells which are lost normally through aging.

The amount of erythropoietin in the circulation is increased under conditions of hypoxia when oxygen transport by blood cells in the circulation is reduced. Hypoxia may be caused by loss of large amounts of blood through hemorrhage, destruction of red blood cells by over-exposure to radiation, reduction in oxygen intake due to high altitudes or prolonged unconsciousness, or various forms of anemia. In response to tissues undergoing hypoxic stress, erythropoietin will increase red blood cell production by stimulating the conversion of primitive precursor cells in the bone marrow into proerythroblasts which subsequently mature, synthesize hemoglobin and are released into the circulation as red blood cells. When the number of red blood cells in circulation is greater than needed for normal tissue oxygen requirements, erythropoietin in circulation is decreased.

See generally, Testa, et al., *Exp. Hematol.*, 8 (*Supp.* 8), 144–152 (1980); Tong, et al., *J. Biol. Chem.*, 256(24), 12666–12672 (1981); Goldwasser, *J. Cell. Physiol.*, 110(*Supp.* 1), 133–135 (1982); Finch, *Blood*, 60(6), 1241–1246 (1982); Sytowski, et al., *Exp. Hematol.*, 8(*Supp* 8), 52–64 (1980) Naughton, *Ann. Clin. Lab. Sci.*, 13(5), 432–438 (1983); Weiss, et al., *Am. J. Vet. Res.*, 44(10), 1832–1835 (1983); Lappin, et al., *Exp. Hematol.*, 11(7), 661–666 (1983); Baciu, et al., *Ann. N.Y. Acad. Sci.*, 414, 66–72 (1983); Murphy, et al., *Acta. Haematologica Japonica*, 46(7), 1380–1396 (1983); Dessypris, et al., *Brit. J. Haematol.*, 56, 295–306 (1984); and, Emmanouel, et al., *Am. J. Physiol.*, 247 (1 Pt 2), F168–76 (1984).

Because erythropoietin is essential in the process of red blood cell formation, the hormone has potential useful application in both the diagnosis and the treatment of blood disorders characterized by low or defective red blood cell production. See, generally, Pennathur-Das, et al., *Blood*, 63(5), 1168–71 (1984) and Haddy, *Am. Jour. Ped. Hematol./Oncol.*, 4, 191–196, (1982) relating to erythropoietin in possible therapies for sickle cell disease, and Eschbach, et al. *J. Clin. Invest.*, 74(2), pp. 434–441, (1984), describing a therapeutic regimen for uremic sheep based on in vivo response to erythropoietin-rich plasma infusions and proposing a dosage of 10 U EPO/kg per day for 15–40 days as corrective of anemia of the type associated with chronic renal failure. See also, Krane, *Henry Ford Hosp. Med. J.*, 31(3), 177–181 (1983).

It has recently been estimated that the availability of erythropoietin in quantity would allow for treatment each year of anemias of 1,600,000 persons in the United States alone. See, e.g., Morrison, "Bioprocessing in Space—an Overview", pp. 557–571 in The World Biotech Report 1984, Volume 2:USA, (Online Publications, New York, N.Y. 1984). Recent studies have provided a basis for projection of efficacy of erythropoietin therapy in a variety of disease states, disorders and states of hematologic irregularity: Vedovato, et al., *Acta. Haematol*, 71, 211–213 (1984) (beta-thalassemia); Vichinsky, et al., *J. Pediatr.*, 105(1), 15–21 (1984) (cystic fibrosis); Cotes, et al., *Brit. J. Obstet. Gyneacol.*, 90(4), 304–311 (1983) (pregnancy, menstrual disorders); Haga, et al., *Acta. Pediatr. Scand.*, 72, 827–831 (1983) (early anemia of prematurity); Claus-Walker, et al., *Arch. Phys. Med. Rehabil.*, 65, 370–374 (1984) (spinal cord injury); Dunn, et al., *Eur. J. Appl. Physiol.*, 52, 178–182 (1984) (space flight); Miller, et al., *Brit. J. Haematol.*, 52, 545–590 (1982) (acute blood loss); Udupa, et al., *J. Lab. Clin. Med.*, 103(4), 574–580 and 581–588 (1984); and Lipschitz, et al., *Blood*, 63(3), 502–509 (1983) (aging); and Dainiak, et al., *Cancer*, 51(6), 1101–1106 (1983) and Schwartz, et al., *Otolaryngol.*, 109, 269–272 (1983) (various neoplastic disease states accompanied by abnormal erythropoiesis).

Prior attempts to obtain erythropoietin in good yield from plasma or urine have proven relatively unsuccessful. Complicated and sophisticated laboratory techniques are necessary and generally result in the collection of very small amounts of impure and unstable extracts containing erythropoietin.

U.S. Pat. No. 3,033,753 describes a method for partially purifying erythropoietin from sheep blood plasma which provides low yields of a crude solid extract containing erythropoietin.

Initial attempts to isolate erythropoietin from urine yielded unstable, biologically inactive preparations of the hormone. U.S. Pat. No. 3,865,801 describes a method of stabilizing the biological activity of a crude substance containing erythropoietin recovered from urine. The resulting crude preparation containing erythropoietin purportedly retains 90% of erythropoietin activity, and is stable.

Another method of purifying human erythropoietin from urine of patients with aplastic anemia is described in Miyake, et al., *J. Biol. Chem.*, Vol. 252, No. 15 (Aug. 10, 1977), pp. 5558–5564. This seven-step procedure includes ion exchange chromatography, ethanol precipitation, gel filtration, and adsorption chromatography, and yields a pure erythropoietin preparation with a potency of 70,400 units/mg of protein in 21% yield.

U.S. Pat. No. 4,397,840 to Takezawa, et al. describes methods for preparing "an erythropoietin product" from healthy human urine specimens with weakly basic ion exchangers and proposes that the low molecular weight products obtained "have no inhibitory effects" against erythropoietin.

U.K. Patent Application No. 2,085,887 by Sugimoto, et al., published May 6, 1982, describes a process for the production of hybrid human lymphoblastoid cells, reporting production levels ranging from 3 to 420 Units of erythropoietin per ml of suspension of cells (distributed into the cultures after mammalian host propagation) containing up to $10^7$ cells per ml. At the highest production levels asserted to have been obtained, the rate of erythropoietin production could be calculated to be from 40 to about 4,000 Units/$10^6$ cells/48 hours in in vitro culture following transfer of cells from in vivo propagation systems. (See also the equivalent U.S. Pat. No. 4,377,513.) Numerous proposals have been made for isolation of erythropoietin from tissue sources, including neoplastic cells, but the yields have been quite low. See, e.g., Jelkman, et al., *Expt. Hematol.*, 11(7), 581–588 (1983); Tambourin, et al., *P.N.A.S. (U.S.A.)*, 80, 6269–6273 (1983); Katsuoka, et al., *Gann*, 74, 534–541 (1983); Hagiwara, et al., *Blood*, 63(4), 828–835 (1984); and Choppin, et al., *Blood*, 64(2), 341–347 (1984).

Other isolation techniques utilized to obtain purified erythropoietin involve immunological procedures. A polyclonal, serum-derived antibody directed against erythropoietin is developed by injecting an animal, preferably a rat or rabbit, with human erythropoietin. The injected human erythropoietin is recognized as a foreign antigenic substance by the immune system of the animal and elicits production of antibodies against the antigen. Differing cells responding to stimulation by the antigenic substance produce and release into circulation antibodies slightly different from those produced by other responding cells. The antibody activity remains in the serum of the animal when its blood is extracted. While unpurified serum or antibody preparations purified as a serum immunoglobulin G fraction may then be used in assays to detect and complex with human erythropoietin, the materials suffer from a major disadvantage. This serum antibody, composed of all the different antibodies produced by individual cells, is polyclonal in nature and will complex with components in crude extracts other than erythropoietin alone.

Of interest to the background of the present invention are recent advances in the art of developing continuous cultures of cells capable of producing a single species of antibody which is specifically immunologically reactive with a single antigenic determinant of a selected antigen. See, generally, Chisholm, *High Technology*, Vol. 3, No. 1, 57–63 (1983). Attempts have been made to employ cell fusion and hybridization techniques to develop "monoclonal" antibodies to erythropoietin and to employ these antibodies in the isolation and quantitative detection of human erythropoietin. As one example, a report of the successful development of mouse-mouse hybridoma cell lines secreting monoclonal antibodies to human erythropoietin appeared in abstract form in Lee-Huang, Abstract No. 1463 of *Fed. Proc.*, 41, 520 (1982). As another example, a detailed description of the preparation and use of a monoclonal, anti-erythropoietin antibody appears in Weiss, et al., *P.N.A.S. (U.S.A.)*, 79, 5465–5469 (1982). See also, Sasaki, *Biomed. Biochim. Acta.*, 42(11/12), S202–S206 (1983); Yanagawa, et al., *Blood*, 4(2), 357–364 (1984); Yanagawa, et al., *J. Biol. Chem.*, 259(5), 2707–2710 (1984); and U.S. Pat. No. 4,465,624.

Also of interest to the background of the invention are reports of the immunological activity of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones, and the like. Included among the immune reactions of such polypeptides is the provocation of the formation of specific antibodies in immunologically active animals. See, e.g., Lerner, et al., *Cell*, 23, 309–310 (1981); Ross, et al., *Nature*, 294, 654–656 (1981); Walter, et al., *P.N.A.S. (U.S.A.)*, 77, 5197–5200 (1980); Lerner, et al., *P.N.A.S. (U.S.A.)*, 78, 3403–3407 (1981); Walter, et al., *P.N.A.S. (U.S.A.)*, 78, 4882–4886 (1981); Wong, et al., *P.N.A.S. (U.S.A.)*, 78, 7412–7416 (1981); Green, et al. *Cell*, 28, 477–487 (1982); Nigg, et al., *P.N.A.S. (U.S.A.)*, 79, 5322–5326 (1982); Baron, et al., *Cell*, 28, 395–404 (1982); Dreesman, et al., *Nature*, 295, 158–160 (1982); and Lerner, et al., *Scientific American*, 248, No. 2, 66–74 (1983). See, also, Kaiser, et al., *Science*, 223, pp. 249–255 (1984) relating to biological and immunological activities of synthetic peptides which approximately share secondary structures of peptide hormones but may not share their primary structural conformation. The above studies relate, of course, to amino acid sequences of proteins other than erythropoietin, a substance for which no substantial amino acid sequence information has been published. In co-owned, co-pending U.S. patent application Ser. No. 463,724, filed Feb. 4, 1983, by J. Egrie, published Aug. 22, 1984 as European Patent Application No. 0 116 446, there is described a mouse-mouse hybridoma cell line (A.T.C.C. No. HB8209) which produces a highly specific monoclonal, anti-erythropoietin antibody which is also specifically immunoreactive with a polypeptide comprising the following sequence of amino acids: NH$_2$-Ala-Pro-Pro-Arg-Leu-Ile-Cys-Asp-Ser-Arg-Val-Leu-Glu-Arg-Tyr-Leu-Leu-Glu-Ala-Lys-COOH. The polypeptide sequence is one assigned to the first twenty amino acid residues of mature human erythropoietin isolated according to the method of Miyake, et al., *J. Biol. Chem.*, 252, 5558–5564 (1977) and upon which amino acid analysis was performed by the gas phase sequencer (Applied Biosystems, Inc.) according to the procedure of Hewick, M., et al., *J. Biol. Chem.*, 256, 7990–7997

(1981). See, also, Sue, et al., *Proc. Nat. Acad. Sci. (USA)*, 80, pp. 3651–3655 (1983) relating to development of polyclonal antibodies against a synthetic 26-mer based on a differing amino acid sequence, and Sytowski, et al., *J. Immunol. Methods*, 69, pp. 181–186 (1984).

While polyclonal and monoclonal antibodies as described above provide highly useful materials for use in immunoassays for detection and quantification of erythropoietin and can be useful in the affinity purification of erythropoietin, it appears unlikely that these materials can readily provide for the large scale isolation of quantities of erythropoietin from mammalian sources sufficient for further analysis, clinical testing and potential wide-ranging therapeutic use of the substance in treatment of, e.g., chronic kidney disease wherein diseased tissues fail to sustain production of erythropoietin. It is consequently projected in the art that the best prospects for fully characterizing mammalian erythropoietin and providing large quantities of it for potential diagnostic and clinical use involve successful application of recombinant procedures to effect large scale microbial synthesis of the compound.

While substantial efforts appear to have been made in attempted isolation of DNA sequences coding for human and other mammalian species erythropoietin, none appear to have been successful. This is due principally to the scarcity of tissue sources, especially human tissue sources, enriched in mRNA such as would allow for construction of a cDNA library from which a DNA sequence coding for erythropoietin might be isolated by conventional techniques. Further, so little is known of the continuous sequence of amino acid residues of erythropoietin that it is not possible to construct, e.g., long polynucleotide probes readily capable of reliable use in DNA/DNA hybridization screening of cDNA and especially genomic DNA libraries. Illustratively, the twenty amino acid sequence employed to generate the above-named monoclonal antibody produced by A.T.C.C. No. HB8209 does not admit to the construction of an unambiguous, 60 base oligonucleotide probe in the manner described by Anderson, et al., supra. It is estimated that the human gene for erythropoietin may appear as a "single copy gene" within the human genome and, in any event, the genetic material coding for human erythropoietin is likely to constitute less than 0.00005% of total human genomic DNA which would be present in a genomic library.

To date, the most successful of known reported attempts at recombinant-related methods to provide DNA sequences suitable for use in microbial expression of isolatable quantities of mammalian erythropoietin have fallen far short of the goal. As an example, Farber, et al. *Exp. Hematol.*, 11, Supp. 14, Abstract 101 (1983) report the extraction of mRNA from kidney tissues of phenylhydrazine-treated baboons and the injection of the mRNA into *Xenopus laevis* oocytes with the rather transitory result of in vitro production of a mixture of "translation products" which included among them displaying biological properties of erythropoietin. More recently, Farber, et al., *Blood*, 62, No. 5, Supp. No. 1, Abstract 392, at page 122a (1983) reported the in vitro translation of human kidney mRNA by frog oocytes. The resultant translation product mixture was estimated to include on the order of 220 mU of a translation product having the activity of erythropoietin per microgram of injected mRNA. While such levels of in vitro translation of exogenous mRNA coding for erythropoietin were acknowledged to be quite low (compared even to the prior reported levels of baboon mRNA translation into the sought-for product) it was held that the results confirm the human kidney as a site of erythropoietin expression, allowing for the construction of an enriched human kidney cDNA library from which the desired gene might be isolated. [See also, Farber, *Clin. Res.*, 31(4), 769A (1983).]

Since the filing of U.S. patent application Ser. Nos. 561,024 and 582,185, there has appeared a single report of the cloning and expression of what is asserted to have been human erythropoietin cDNA in *E. coli*. Briefly put, a number of cDNA clones were inserted into *E. coli* plasmids and β-lactamase fusion products were noted to be immunoreactive with a monoclonal antibody to an unspecified "epitope" of human erythropoietin. See, Lee-Huang, *Proc. Nat. Acad. Sci. (USA)*, 81, pp. 2708–2712 (1984).

BRIEF SUMMARY

The present invention provides, for the first time, novel purified and isolated polypeptide products having part or all of the primary structural conformation (i.e., continuous sequence of amino acid residues) and one or more of the biological properties (e.g., immunological properties and in vivo and in vitro biological activity) of naturally-occurring erythropoietin, including allelic variants thereof. These polypeptides are also uniquely characterized by being the product of procaryotic or eucaryotic host expression (e.g., by bacterial, yeast and mammalian cells in culture) of exogenous DNA sequences obtained by genomic or cDNA cloning or by gene synthesis. Products of microbial expression in vertebrate (e.g., mammalian and avian) cells may be further characterized by freedom from association with human proteins or other contaminants which may be associated with erythropoietin in its natural mammalian cellular environment or in extracellular fluids such as plasma or urine. The products of typical yeast (e.g., *Saccharomyces cerevisiae*) or procaryote (e.g., *E. coli*) host cells are free of association with any mammalian proteins. Depending upon the host employed, polypeptides of the invention may be glycosylated with mammalian or other eucaryotic carbohydrates or may be non-glycosylated. Polypeptides of the invention may also include an initial methionine amino acid residue position -1).

Novel glycoprotein products of the invention include those having a primary structural conformation sufficiently duplicative of that of a naturally-occurring (e.g., human) erythropoietin to allow possession of one or more of the biological properties thereof and having an average carbohydrate composition which differs from that of naturally-occurring (e.g., human) erythropoietin.

Vertebrate (e.g., COS-1 and CHO) cells provided by the present invention comprise the first cells ever available which can be propagated in vitro continuously and which upon growth in culture are capable of producing in the medium of their growth in excess of 100U (preferably in excess of 500U and most preferably in excess of 1,000 to 5,000U) of erythropoietin per $10^6$ cells in 48 hours as determined by radioimmunoassay.

Also provided by the present invention are synthetic polypeptides wholly or partially duplicative of continuous sequences of erythropoietin amino acid residues which are herein for the first time elucidated. These sequences, by virtue of sharing primary, secondary or tertiary structural and conformational characteristics with naturally-occurring erythropoietin may possess biological activity and/or immunological properties in common with the naturally-occurring product such that they may be employed as biologically active or immunological substitutes for erythropoietin in therapeutic and immunological processes. Correspondingly provided are monoclonal and polyclonal antibodies generated by standard means which are immunoreactive with such polypeptides and, preferably, also immunoreactive with naturally-occurring erythropoietin.

Illustrating the present invention are cloned DNA sequences of monkey and human species origins and polypeptide sequences suitably deduced therefrom which represent, respectively, the primary structural conformation of erythropoietins of monkey and human species origins.

Also provided by the present invention are novel biologically functional viral and circular plasmid DNA vectors incorporating DNA sequences of the invention and microbial (e.g., bacterial, yeast and mammalian cell) host organisms stably transformed or transfected with such vectors. Correspondingly provided by the invention are novel methods for the production of useful polypeptides comprising cultured growth of such transformed or transfected microbial hosts under conditions facilitative of large scale expression of the exogenous, vector-borne DNA-sequences and isolation of the desired polypeptides from the growth medium, cellular lysates or cellular membrane fractions.

Isolation and purification of microbially expressed polypeptides provided by the invention may be by conventional means including, e.g., preparative chromatographic separations and immunological separations involving monoclonal and/or polyclonal antibody preparations.

Having herein elucidated the sequence of amino acid residues of erythropoietin, the present invention provides for the total and/or partial manfucture of DNA sequences coding for erythropoietin and including such advantageous characteristics as incorporation of codons "preferred" for expression by selected non-mammalian hosts, provision of sites for cleavage by restriction endonuclease enzymes and provision of additional initial, terminal or intermediate DNA sequences which facilitate construction of readily expressed vectors. Correspondingly, the present invention provides for manufacture (and development by site specific mutagenesis of cDNA and genomic DNA) of DNA sequences coding for microbial expression of polypeptide analogs or derivatives of erythropoietin which differ from naturally-occurring forms in terms of the identity or location of one or more amino acid residues (i.e., deletion analogs containing less than all of the residues specified for EPO and/or substitution analogs wherein one or more residues specified are replaced by other residues and/or addition analogs wherein one or more amino acid residues is added to a terminal or medial portion of the polypeptide); and which share some or all the properties of naturally-occurring forms.

Novel DNA sequences of the invention include all sequences useful in securing expression in procaryotic or eucaryotic host cells of polypeptide products having at least a part of the primary structural conformation and one or more of the biological properties of erythropoietin which are comprehended by: (a) the DNA sequences set out in FIGS. 5 and 6 herein or their complementary strands; (b) DNA sequences which hybridize (under hybridization conditions such as illustrated herein or more stringent conditions) to DNA sequences defined in (a) or fragments thereof; and (c) DNA sequences which, but for the degeneracy of the genetic code, would hybridize to DNA sequences defined in (a) and (b) above. Specifically comprehended in part (b) are genomic DNA sequences encoding allelic variant forms of monkey and human erythropoietin and/or encoding other mammalian species of erythropoietin. Specifically comprehended by part (c) are manufactured DNA sequences encoding EPO, EPO fragments and EPO analogs which DNA sequences may incorporate codons facilitating translation of messenger RNA in non-vertebrate hosts.

Comprehended by the present invention is that class of polypeptides coded for by portions of the DNA complement to the top strand human genomic DNA sequence of FIG. 6 herein, i.e., "complementary inverted proteins" as described by Tramontano, et al., *Nucleic Acids Research*, 12, pp. 5049–5059 (1984).

Also comprehended by the invention are pharmaceutical compositions comprising effective amounts of polypeptide products of the invention together with suitable diluents, adjuvants and/or carriers which allow for provision of erythropoietin therapy, especially in the treatment of anemic disease states and most especially such anemic states as attend chronic renal failure.

Polypeptide products of the invention may be "labelled" by covalent association with a detectable marker substance (e.g., radiolabelled with $^{125}$I) to provide reagents useful in detection and quantification of erythropoietin in solid tissue and fluid samples such as blood or urine. DNA products of the invention may also be labelled with detectable markers (such as radiolabels and non-isotopic labels such as biotin) and employed in DNA hybridization processes to locate the erythropoietin gene position and/or the position of any related gene family in the human, monkey and other mammalian species chromosomal map. They can also be used for identifying the erythropoietin gene disorders at the DNA level and used as gene markers for identifying neighboring genes and their disorders.

As hereinafter described in detail, the present invention further provides significant improvements in methods for detection of a specific single stranded polynucleotide of unknown sequence in a heterogeneous cellular or viral sample including multiple single-stranded polynucleotides where (a) a mixture of labelled single-stranded polynucleotide probes is prepared having uniformly varying sequences of bases, each of said probes being potentially specifically complementary to a sequence of bases which is putatively unique to the polynucleotide to be detected, (b) the sample is fixed to a solid substrate, (c) the substrate having the sample fixed thereto is treated to diminish further binding of polynucleotides thereto except by way of hybridization to polynucleotides in said sample, (d) the treated substrate having the sample fixed thereto is transitorily contacted with said mixture of labelled probes under conditions facilitative of hybridization only between totally complementary polynucleotides, and, (e) the specific polynucleotide is detected by monitoring for the presence of a hybridization reaction between it and a totally complementary probe within said mixture of labelled probes, as evidenced by the presence of a higher density of labelled material on the substrate at the locus of the specific polynucleotide in comparison to a background density of labelled material resulting from non-specific binding of labelled probes to the substrate.

The procedures are especially effective in situations dictating use of 64, 128, 256, 512, 1024 or more mixed polynucleotide probes having a length of 17 to 20 bases in DNA/DNA or RNA/RNA or DNA/RNA hybridizations.

As described infra, the above-noted improved procedures have illustratively allowed for the identification of cDNA clones coding for erythropoietin of monkey species origins within a library prepared from anemic monkey kidney cell mRNA. More specifically, a mixture of 128 uniformly varying 20-mer probes based on amino acid sequence information derived from sequencing fractions of human erythropoietin was employed in colony hybridization procedures to identify seven "positive" erythropoietin cDNA clones within a total of 200,000 colonies. Even more remarkably, practice of the improved procedures of the invention have allowed for the rapid isolation of three positive clones from within a screening of 1,500,000 phage plaques constituting a human genomic library. This was accomplished through use of the above-noted mixture of 128 20-mer probes together with a second set of 128 17-mer probes based on amino acid analysis of a different continuous sequence of human erythropoietin.

The above-noted illustrative procedures constitute the first known instance of the use of multiple mixed oligonucleotide probes in DNA/DNA hybridization processes directed toward isolation of mammalian genomic clones and the first known instance of the use of a mixture of more than 32 oligonucleotide probes in the isolation of cDNA clones.

Numerous aspects and advantages of the invention will be apparent to those skilled in the art upon consideration of the following detailed description which provides illustrations of the practice of the invention in its presently preferred embodiments.

Reference is made to FIGS. 1 through 21, wherein.

Figure 1:
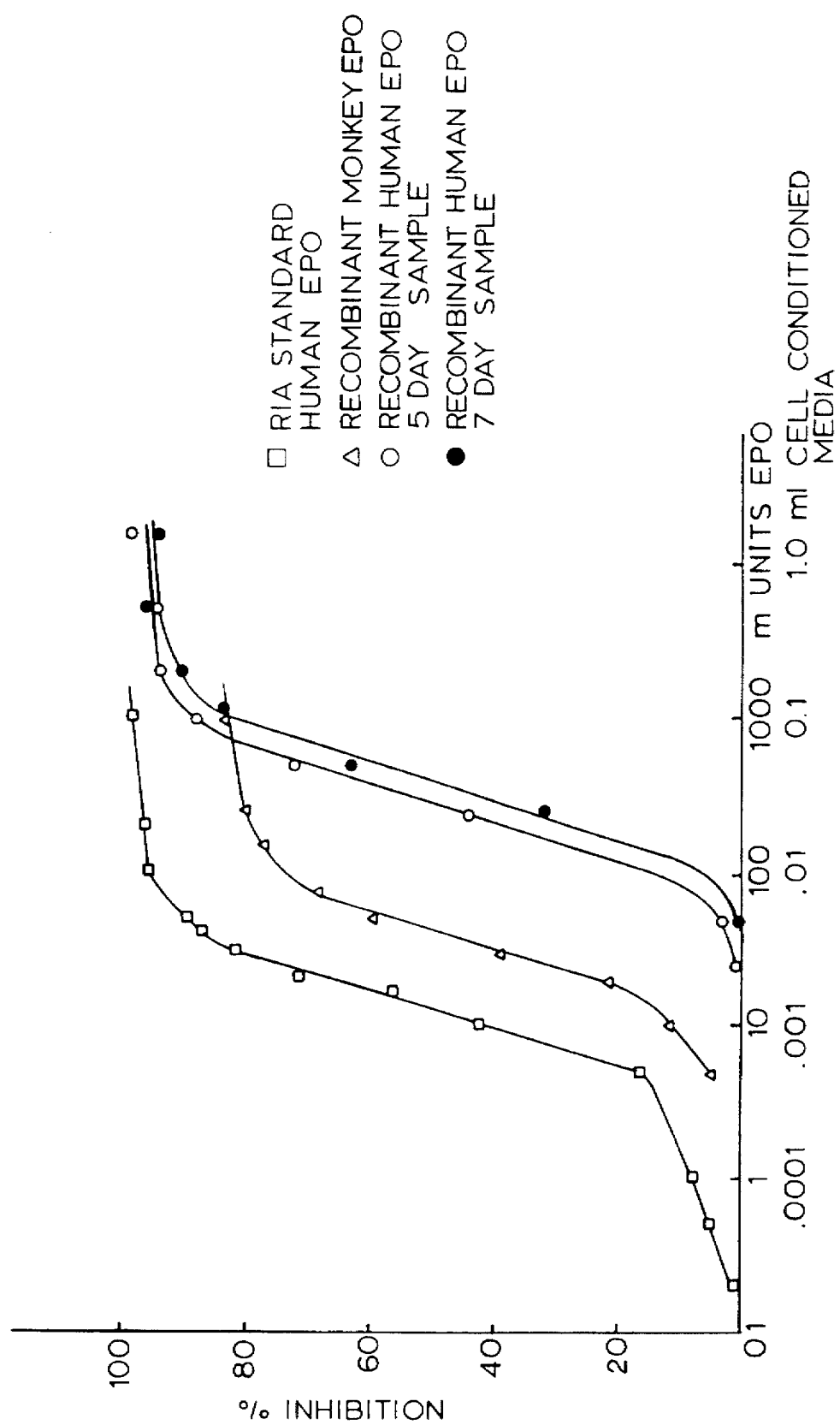
FIG. 1 is a graphic representation of a radioimmunoassay analysis of products of the invention.

FIGS. 5A, 5B and 5C (collectively referred to as FIG. 5) show the sequence of monkey EPO cDNA and the encoded EPO.

FIGS. 6A, 6B, 6C, 6D and 6E (collectively referred to as FIG. 6) show the sequence of human genomic EPO DNA and the encoded EPO.

FIG. 7 shows the sequence of the ECEPO gene.

FIG. 8 shows the sequence of the SCEPO gene.

FIG. 9 shows a comparison of the human and monkey EPO polypeptides.

FIG. 10 shows the ECEPO section 1 oligonucleotides.

FIG. 11 shows section 1 of the ECEPO gene.

FIG. 12 shows the ECEPO section 2 oligonucleotides.

FIG. 13 shows section 2 of the ECEPO gene.

FIG. 14 shows the ECEPO section 3 oligonucleotides.

FIG. 15 shows section 3 of the ECEPO gene.

FIG. 16 shows the SCEPO section 1 oligonucleotides.

FIG. 17 shows section 1 of the SCEPO gene.

FIG. 18 shows the SCEPO section 2 oligonucleotides.

FIG. 19 shows section 2 of the SCEPO gene.

FIG. 20 shows the SCEPO section 3 oligonucleotides.

FIG. 21 shows the section 3 of the SCEPO gene.

DETAILED DESCRIPTION

According to the present invention, DNA sequences encoding part or all of the polypeptide sequence of human and monkey species erythropoietin (hereafter, at times, "EPO") have been isolated and characterized. Further, the monkey and human origin DNA has been made the subject of eucaryotic and procaryotic expression providing isolatable quantities of polypeptides displaying biological (e.g., immunological) properties of naturally-occurring EPO as well as both in vivo and in vitro biological activities of EPO.

The DNA of monkey species origins was isolated from a cDNA library constructed with mRNA derived from kidney tissue of a monkey in a chemically induced anemic state and whose serum was immunologically determined to include high levels of EPO compared to normal monkey serum. The isolation of the desired cDNA clones containing EPO encoding DNA was accomplished through use of DNA/DNA colony hybridization employing a pool of 128 mixed, radiolabelled, 20-mer oligonucleotide probes and involved the rapid screening of 200,000 colonies. Design of the oligonucleotide probes was based on amino acid sequence information provided by enzymatic fragmentation and sequencing of a small sample of human EPO.

The DNA of human species origins was isolated from a human genomic DNA library. The isolation of clones containing EPO-encoding DNA was accomplished through DNA/DNA plaque hybridization employing the above-noted pool of 128 mixed 20-mer oligonucleotide probes and a second pool of 128 radiolabelled 17-mer probes whose sequences were based on amino acids sequence information obtained from a different enzymatic human EPO fragment.

Positive colonies and plaques were verified by means of dideoxy sequencing of clonal DNA using a subset of 16 sequences within the pool of 20-mer probes and selected clones were subjected to nucleotide sequence analysis resulting in deduction of primary structural conformation of the EPO polypeptides encoded thereby. The deduced polypeptide sequences displayed a high degree of homology to each other and to a partial sequence generated by amino acid analysis of human EPO fragments.

A selected positive monkey cDNA clone and a selected positive human genomic clone were each inserted in a "shuttle" DNA vector which was amplified in *E. coli* and employed to transfect mammalian cells in culture. Cultured growth of transfected host cells resulted in culture medium supernatant preparations estimated to contain as much as 3000 mU of EPO per ml of culture fluid.

The following examples are presented by way of illustration of the invention and are specifically directed to procedures carried out prior to identification of EPO encoding monkey cDNA clones and human genomic clones, to procedures resulting in such identification, and to the sequencing, development of expression systems and immunological verification of EPO expression in such systems.

More particularly, Example 1 is directed to amino acid sequencing of human EPO fragments and construction of mixtures of radiolabelled probes based on the results of this sequencing. Example 2 is generally directed to procedures involved in the identification of positive monkey cDNA clones and thus provides information concerning animal treatment and preliminary radioimmunoassay (RIA) analysis of animal sera. Example 3 is directed to the preparation of the cDNA library, colony hybridization screening and verification of positive clones, DNA sequencing of a positive cDNA clone and the generation of monkey EPO polypeptide primary structural conformation (amino acid sequence) information. Example 4 is directed to procedures involved in the identification of positive human genomic clones and thus provides information concerning the source of the genomic library, plaque hybridization procedures and verification of positive clones. Example 5 is directed to DNA sequencing of a positive genomic clone and the generation of human EPO polypeptide amino acid sequence information including a comparison thereof to the monkey EPO sequence information. Example 6 is directed to procedures for construction of a vector incorporating EPO-encoding DNA derived from a positive monkey cDNA clone, the use of the vector for transfection of COS-1 cells and cultured growth of the transfected cells. Example 7 is directed to procedures for construction of a vector incorporating EPO-encoding DNA derived from a positive human genomic clone, the use of the vector for transfection of COS-1 cells and the cultured growth of the transfected cells. Example 8 is directed to immunoassay procedures performed on media supernatants obtained from the cultured growth of transfected cells according to Example 6 and 7. Example 9 is directed to in vitro and in vivo biological activity of microbially expressed EPO of Examples 6 and 7.

Example 10 is directed to a development of mammalian host expression systems for monkey species EPO cDNA and human species genomic DNA involving Chinese hamster ovary ("CHO") cells and to the immunological and biological activities of products of these expression systems as well as characterization of such products. Example 11 is directed to the preparation of manufactured genes encoding human species EPO and EPO analogs, which genes include a number of preference codons for expression in *E. coli* and yeast host cells, and to expression systems based thereon. Example 12 relates to the immunological and biological activity profiles of expression products of the systems of Example 11.

EXAMPLE 1

A. Human EPO Fragment Amino Acid Sequencing

Human EPO was isolated from urine and subjected to tryptic digestion resulting in the development and isolation of 17 discrete fragments in quantities approximating 100–150 picomoles.

Fragments were arbitrarily assigned numbers and were analyzed for amino acid sequence by microsequence analysis using a gas phase sequencer (Applied Biosystems) to provide the sequence information set out in Table I, below, wherein single letter codes are employed and "X" designates a residue which was not unambiguously determined.

TABLE I

| Fragment No. | Sequence Analysis Result |
|---|---|
| T4a | A—P—P—R |
| T4b | G—K—L—K |
| T9 | A—I—G—A—Q—K |
| T13 | V—L—E—R |
| T16 | A—V—S—G—L—R |
| T18 | L—F—R |
| T21 | K—L—F—R |
| T25 | Y—L—L—E—A—K |
| T26a | L—I—C—D—S—R |
| T26b | L—Y—T—G—E—A—C—R |
| T27 | T—I—T—A—D—T—F—R |
| T28 | E—A—I—S—P—P—D—A—A—M—A—A—P—L—R |
| T30 | E—A—E—X—I—T—T—G—X—A—E—H—X—S—L—N—E—X—I—T—V—P |
| T31 | V—Y—S—N—F—L—R |
| T33 | S—L—T—T—L—L—R |
| T35 | V—N—F—Y—A—W—K |
| T38 | G—Q—A—L—L—V—X—S—S—Q—P—W—E—P—L—Q—L—H—V—D—K |

B. Design and Construction of Oligonucleotide Probe Mixtures

The amino acid sequences set out in Table I were reviewed in the context of the degeneracy of the genetic code for the purpose of ascertaining whether mixed probe procedures could be applied to DNA/DNA hybridization procedures on cDNA and/or genomic DNA libraries. This analysis revealed that within Fragment No. T35 there existed a series of 7 amino acid residues (Val-Asn-Phe-Tyr-Ala-Trp-Lys) which could be uniquely characterized as encoded for by one of 128 possible DNA sequences spanning 20 base pairs. A first set of 128 20-mer oligonucleotides was therefore synthesized by standard phosphoamidite methods (See, e.g., Beaucage, et al., *Tetrahedron Letters*, 22, pp. 1859–1862 (1981) on a solid support according to the sequence set out in Table II, below.

TABLE II

| Residue | - | Val | - | Asn | Phe | Tyr | Ala | Trp | Lys | |
|---|---|---|---|---|---|---|---|---|---|---|
| 3' | | CAA | | TTG | AAG | ATG | CGA | ACC | TT | - 5' |
| | | T | | A | A | A | T | | | |
| | | G | | | | | G | | | |
| | | C | | | | | C | | | |

Further analysis revealed that within fragment No. T38 there existed a series of 6 amino acid residues (Gln-Pro-Trp-Glu-Pro-Leu) on the basis of which there could be prepared a pool of 128 mixed olignucleotide 17-mer probes as set out in Table III, below.

TABLE III

| Residue | - | Gln | Pro | Trp | Glu | Pro | Leu | |
|---|---|---|---|---|---|---|---|---|
| 3' | | GTT | GGA | ACC | CTT | GGA | GA | - 5' |
| | | C | T | | C | T | A | |
| | | | G | | | G | | |
| | | | C | | | C | | |

Oligonucleotide probes were labelled at the 5' end with gamma—$^{32}$P-ATP, 7500–8000 Ci/mmole (ICN) using T$_4$ polynucleotide kinase (NEN).

EXAMPLE 2

A. Monkey Treatment Procedures

Female Cynomolgus monkeys *Macaca fascicularias* (2.5–3 kg, 1.5–2 years old) were treated subcutaneously with a pH 7.0 solution of phenylhydrazine hydrochloride at a dosage level of 12.5 mg/kg on days 1, 3 and 5. The hematocrit was monitored prior to each injection. On day 7, or whenever the hematocrit level fell below 25% of the initial level, serum and kidneys were harvested after administration of 25 mg/kg doses of ketamine hydrochloride. Harvested materials were immediately frozen in liquid nitrogen and stored at −70° C.

B. RIA for EPO

Radioimmunoassay procedures applied for quantitative detection of EPO in samples were conducted according to the following procedures:

An erythropoietin standard or unknown sample was incubated together with antiserum for two hours at 37° C. After the two hour incubation, the sample tubes were cooled on ice, and $^{125}$I labelled erythropoietin was added, the tubes were incubated at 0° C. for at least 15 more hours. Each assay tube contained 500 μl of incubation mixture consisting of 50 μl of diluted immune sera, 10,000 cpm of $^{125}$I-erythropoietin, 5 μl trasylol and 0–250 μl of either EPO standard or unknown sample, with PBS containing 0.1% BSA making up the remaining volume. The antiserum used was the second test bleed of a rabbit immunized with a 1% pure preparation of human urinary erythropoietin. The final antiserum dilution on the assay was adjusted so that the antibody-bound $^{125}$I-EPO did not exceed 10–20% of the input total counts. In general, this corresponded to a final antiserum dilution of from 1:50,000 to 1:100,000.

The antibody-bound $^{125}$I-erythropoietin was precipitated by the addition of 150 μl Staph A. After a 40 min. incubation, the samples were centrifuged and the pellets were washed two times with 0.75 ml 10 mM Tris-HCl pH 8.2 containing 0.15M NaCl, 2 mM EDTA, and 0.05% Triton X-100. The washed pellets were counted in a gamma counter to determine the percent of $^{125}$I-erythropoietin bound. Counts bound by pre-immune sera were subtracted from all final values to correct for nonspecific precipitation. The erythropoietin content of the unknown samples was determined by comparison to the standard curve.

The above procedure was applied to monkey serum obtained in Part A, above, as well as to the untreated monkey serum. Normal serum levels were assayed to contain approximately 36 mU/ml while treated monkey serum contained from 1000 to 1700 mU/ml.

EXAMPLE 3

A. Monkey cDNA Library Construction

Messenger RNA was isolated from normal and anemic monkey kidneys by the guanidinium thiocyanate procedure of Chirgwin, et al., *Biochemistry*, 18, p. 5294 (1979) and poly (A)$^+$ mRNA was purified by two runs of oligo(dT)-cellulose column chromatography as described at pp. 197–198 in Maniatis, et al., "Molecular Cloning, A Laboratory Manual" (Cold Springs Harbor Laboratory, Cold Springs Harbor, N.Y., 1982). The cDNA library was constructed according to a modification of the general procedures of Okayama, et al., *Mol. and Cell. Biol.*, 2, pp. 161–170 (1982). The key features of the presently preferred procedures were as follows: (1) pUC8 was used as the sole vector, cut with PstI and then tailed with oligo dT of 60–80 bases in length; (2) HincII digestion was used to remove the oligo dT tail from one end of the vector; (3) first strand synthesis and oligo dG tailing was carried out according to the published procedure; (4) BamHI digestion was employed to remove the oligo dG tail from one end of the vector; and (5) replacement of the RNA strand by DNA was in the presence of two linkers (GATCTAAAGACCGTC-CCCCCCCC and ACGGTCTTTA) in a three-fold molar excess over the oligo dG tailed vector.

B. Colony Hybridization Procedures For Screening Monkey cDNA Library

Transformed *E. coli* were spread out at a density of 9000 colonies per 10×10 cm plate on nutrient plates containing 50 micrograms/ml Ampicillin. GeneScreen filters (New England Nuclear Catalog No. NEF-972) were pre-wet on a BHI-CAM plate (Bacto brain heart infusion 37 g/L, Casamino acids 2 g/L and agar 15 g/L, containing 500 micrograms/ml Chloramphenicol) and were used to lift the colonies off the plate. The colonies were grown in the same medium for 12 hours or longer to amplify the plasmid copy numbers. The amplified colonies (colony side up) were treated by serially placing the filters over 2 pieces of Whatman 3 MM paper saturated with each of the following solutions:

(1) 50 mM glucose—25 mM Tris-HCl (pH 8.0)—10 mM EDTA (pH 8.0) for five minutes;

(2) 0.5M NaOH for ten minutes; and (3) 1.0M Tris-HCl (pH 7.5) for three minutes.

The filters were then air dried in a vacuum oven at 80° C. for two hours.

The filters were then subjected to Proteinase K digestion through treatment with a solution containing 50 micrograms/ml of the protease enzyme in Buffer K [0.1M Tris-HCl (pH 8.0)—0.15M NaCl—10 mM EDTA (pH 8.2)—0.2% SDS]. Specifically, 5 ml of the solution was added to each filter and the digestion was allowed to proceed at 55° C. for 30 minutes, after which the solution was removed.

The filters were then treated with 4 ml of a prehybridization buffer (5×SSPE—0.5% SDS—100 micrograms/ml SS *E. coli* DNA—5×BFP). The prehybridization treatment was carried out at 55° C., generally for 4 hours or longer, after which the prehybridization buffer was removed.

The hybridization process was carried out in the following manner. To each filter was added 3 ml of hybridization buffer (5×SSPE—0.5% SDS—100 micrograms/ml yeast tRNA) containing 0.025 picomoles of each of the 128 probe sequences of Table II (the total mixture being designated the EPV mixture) and the filters were maintained at 48° C. for 20 hours. This temperature was 2° C. less than the lowest of the calculated dissociation temperatures (Td) determined for any of the probes.

Following hybridization, the filters were washed three times for ten minutes on a shaker with 6×SSC—0.1% SDS at room temperature and washed two to three times with 6×SSC—1% SDS at the hybridization temperature (48° C.).

Autoradiography of the filters revealed seven positive clones among the 200,000 colonies screened.

Initial sequence analysis of one of the putative monkey cDNA clones (designated clone 83 deposited with the American Type Culture Collection, 12301 Parklawn Drive, Rockville, Md., under accession No. A.T.C.C. 67545 on Oct. 20, 1987) was performed for verification purposes by a modification of the procedure of Wallace, et al., *Gene*, 16, pp. 21–26 (1981). Briefly, plasmid DNA from monkey cDNA clone 83 was linearized by digestion with EcoRI and denatured by heating in a boiling water bath. The nucleotide sequence was determined by the dideoxy method of Sanger, et al., *P.N.A.S. (U.S.A.)*, 74, pp. 5463–5467 (1977). A subset of the EPV mixture of probes consisting of 16 sequences was used as a primer for the sequencing reactions.

C. Monkey EPO cDNA Sequencing

Nucleotide sequence analysis of clone 83 was carried out by the procedures of Messing, Methods in *Enzymology*, 101, pp. 20–78 (1983). Set out in Table IV is a preliminary restriction map analysis of the approximately 1600 base pair EcoRI/HindIII cloned fragment of clone 83. Approximate locations of restriction endonuclease enzyme recognition sites are provided in terms of number of bases 3' to the EcoRI site at the 5' end of the fragment. Nucleotide sequencing was carried out by sequencing individual restriction fragments with the intent of matching overlapping fragments. For example, an overlap of sequence information provided by analysis of nucleotides in a restriction fragment designated C113 (Sau3A at −111/SmaI at −324) and the reverse order sequencing of a fragment designated C73 (AluI at −424/BstEII at −203).

TABLE IV

| Restriction Enzyme Recognition Site | Approximate Location(s) |
|---|---|
| EcoRI | 1 |
| Sau3A | 111 |
| SmaI | 180 |
| BstEII | 203 |
| SmaI | 324 |
| KpnI | 371 |
| RsaI | 372 |
| AluI | 424 |
| PstI | 426 |
| AluI | 430 |
| HpaI | 466 |
| AluI | 546 |
| PstI | 601 |
| PvuII | 604 |
| AluI | 605 |
| AluI | 782 |
| AluI | 788 |
| RsaI | 792 |
| PstI | 807 |
| AluI | 841 |
| AluI | 927 |
| NcoI | 946 |
| Sau3A | 1014 |
| AluI | 1072 |
| AluI | 1115 |
| AluI | 1223 |
| PstI | 1301 |
| RsaI | 1343 |
| AluI | 1384 |
| HindIII | 1449 |
| AluI | 1450 |
| HindIII | 1585 |

Sequencing of approximately 1342 base pairs (within the region spanning the Sau3A site 3' to the EcoRI site and the HindIII site) and analysis of all possible reading frames has allowed for the development of DNA and amino acid sequence information set out in FIG. 5, comprising portions 5A, 5B, and 5C. In the Figure, the putative initial amino acid residue of the amino terminal of mature EPO (as verified by correlation to the previously mentioned sequence analysis of twenty amino terminal residues) is designated by the numeral +1. The presence of a methionine-specifying ATG codon (designated −27) "upstream" of the initial amino terminal alanine residue as the first residue designated for the amino acid sequence of the mature protein is indicative of the likelihood that EPO is initially expressed in the cytoplasm in a precursor form including a 27 amino acid "leader" region which is excised prior to entry of mature EPO into circulation. Potential glycosylation sites within the polypeptide are designated by asterisks. The estimated molecular weight of the translated region was determine to be 21,117 daltons and the M.W. of the 165 residues of the polypeptide constituting mature monkey EPO was determined to be 18,236 daltons.

The polypeptide sequence of FIG. 5 may readily be subjected to analysis for the presence of highly hydrophilic regions and/or secondary conformational characteristics indicative of potentially highly immunogenic regions by, e.g., the methods of Hopp, et al., P.N.A.S. (U.S.A.), 78, pp. 3824–3828 (1981) and Kyte et al., J. Mol. Biol., 157, pp. 105–132 (1982) and/or Chou, et al., Biochem., 13, pp. 222–245 (1974) and Advances in Enzymology, 47, pp. 45–47 (1978). Computer-assisted analysis according to the Hopp, et al. method is available by means of a program designated PEP Reference Section 6.7 made available by Intelligenetics, Inc., 124 University Avenue, Palo Alto, Calif.

EXAMPLE 4

A. Human Genomic Library

A Ch4A phage-borne human fetal liver genomic library prepared according to the procedures of Lawn, et al., Cell, supra was obtained and maintained for use in a plaque hybridization assay.

B. Plaque Hybridization Procedures For Screening Human Genomic Library

Phage particles were lysed and the DNAs were fixed on filters (50,000 plaques per filter) according to the procedures of Woo, Methods In Enzymology, 68, pp. 389–395 (1979) except for the use of GeneScreen Plus filters (New England Nuclear Catalog No. NEF-972) and NZYAM plates (NaCl, 5 g; $MgCl_2$—$6H_2O$, 2 g; NZ-Amine A, 10 g; yeast extract, 5 g; casamino acids, 2 g; maltose; 2 g; and agar, 15 g per liter).

The air-dried filters were baked at 80° C. for 1 hour and then digested with Proteinase K as described in Example 3, Part B. Prehybridization was carried out with a 1M NaCl—1% SDS buffer for 55° C. for 4 hours or more, after which the buffer was removed. Hybridization and post-hybridization washings were carried out as described in Example 3, Part B. Both the mixture of 128 20-mer probes designated EPV and the mixture of 128 17-mer probes of Table III (designated the EPQ mixture) were employed. Hybridization was carried out at 48° C. using the EPV probe mixture. EPQ probe mixture hybridization was carried out at 46° C.—4 degrees below the lowest calculated Td for members of the mixture. Removal of the hybridized probe for rehybridization was accomplished by boiling with 1xSSC—0.1% SDS for two minutes. Autoradiography of the filters revealed three positive clones (reactive with both probe mixtures) among the 1,500,000 phage plaques screened. Verification of the positive clones as being EPO-encoding was obtained through DNA sequencing and electron micrographic visualization of heteroduplex formation with the monkey cDNA of Example 3. This procedure also gave evidence of multiple introns in the genomic DNA sequence.

EXAMPLE 5

Nucleotide sequence analysis of one of the positive clones (designated λhE1, deposited with the American Type Culture Collection, 12301 Parklawn drive, Rockville, Md., under deposit accession No. A.T.C.C. 40381 on Oct. 20, 1987) was carried out and results obtained to date are set out in FIG. 6, comprising portions 6A, 6B, 6C, 6D, and 6E.

In FIG. 6, the initial continuous DNA sequence designates a top strand of 620 bases in what is apparently an untranslated sequence immediately preceding a translated portion of the human EPO gene. More specifically, the sequence appears to comprise the 5' end of the gene which leads up to a translated DNA region coding for the first four amino acids (−27 through −24) of a leader sequence ("presequence"). Four base pairs in the sequence prior to that encoding the beginning of the leader have not yet been unambiguously determined and are therefore designated by an "X". There then follows an intron of about 639 base pairs (439 base pairs of which have been sequenced and the remaining 200 base pairs of which are designated "I.S.") and immediately preceding a codon for glutamic acid which has been designated as residue −23 of the translated polypeptide. The exon sequence immediately following is seen to code for amino acid residues through an alanine residue (designated as the +1 residue of the amino acid sequence of mature human EPO) to the codon specifying threonine at position +26, whereupon there follows a second intron consisting of 256 bases as specifically designated. Following this intron is an exon sequence for amino acid residues 27 through 55 and thereafter a third intron comprising 612 base pairs commences. The subsequent exon codes for residues 56 through 115 of human EPO and there then commences a fourth intron of 134 bases as specified. Following the fourth intron is an exon coding for residue Nos. 116 through 166 and a "stop" codon (TGA). Finally, FIG. 6 identifies a sequence of 568 base pairs in what appears to be an untranslated 3' region of the human EPO gene, two base pairs of which ("X") have not yet been unambiguously sequenced.

FIG. 6 thus serves to identify the primary structural conformation (amino acid sequence) of mature human EPO as including 166 specified amino acid residues (estimated M.W.=18,399). Also revealed in the Figure is the DNA sequence coding for a 27 residue leader sequence along with 5' and 3' DNA sequences which may be significant to promoter/operator functions of the human gene operon. Sites for potential glycosylation of the mature human EPO polypeptide are designated in the Figure by asterisks. It is worthy of note that the specific amino acid sequence of FIG. 6 likely constitutes that of a naturally occurring allelic form of human erythropoietin. Support for this position is found in the results of continued efforts at sequencing of urinary isolates of human erythropoietin which provided the finding that a significant number of erythropoietin molecules therein have a methionine at residue 126 as opposed to a serine as shown in the Figure.

FIG. 9, below, illustrates the extent of polypeptide sequence homology between human and monkey EPO. In the upper continuous line of the Figure, single letter designations are employed to represent the deduced translated polypeptide sequences of human EPO commencing with residue −27 and the lower continuous line shows the deduced polypeptide sequence of monkey EPO commencing at assigned residue number −27. Asterisks are employed to highlight the sequence homologies. It should be noted that the deduced human and monkey EPO sequences reveal an "additional" lysine (K) residue at (human) position 116. Cross-reference to FIG. 6 indicates that this residue is at the margin of a putative mRNA splice junction in the genomic sequence. Presence of the lysine residue in the human polypeptide sequence was further verified by sequencing of a cDNA human sequence clone prepared from mRNA isolated from COS-1 cells transformed with the human genomic DNA in Example 7, infra.

EXAMPLE 6

The expression system selected for initial attempts at microbial synthesis of isolatable quantities of EPO polypeptide material coded for by the monkey cDNA provided by the procedures of Example 3 was one involving mammalian host cells (i.e., COS-1 cells, A.T.C.C. No. CRL-1650). The cells were transfected with a "shuttle" vector capable of autonomous replication in *E. coli* host (by virtue of the presence of pBR322-derived DNA) and the mammalian hosts (by virtue of the presence of SV40 virus-derived DNA).

More specifically, an expression vector was constructed according to the following procedures. The plasmid clone 83 provided in Example 3 was amplified in *E. coli* and the approximately 1.4 kb monkey EPO-encoding DNA was isolated by EcoRI and HindIII digestion. Separately isolated was an approximately 4.0 kb, HindIII/SalI fragment from pBR322. An approximately 30 bp, EcoRI/SalI "linker" fragment was obtained from M13mp10 RF DNA (P and L Laboratories). This linker included, in series, an EcoRI sticky end, followed by SstI, SmaI, BamHI and XbaI recognition sites and a SalI sticky end. The above three fragments were ligated to provide an approximately 5.4 kb intermediate plasmid ("pERS") wherein the EPO DNA was flanked on one side by a "bank" of useful restriction endonuclease recognition sites. pERS was then digested with HindIII and SalI to yield the EPO DNA and the EcoRI to SalI (M13mp10) linker. The 1.4 kb fragment was ligated with an approximately 4.0 kb BamHI/SalI of pBR322 and another M13mp10 HindIII/BamHI RF fragment linker also having approximately 30 bp. The M13 linker fragment was characterized by a HindIII sticky end, followed by PstI, SalI, XbaI recognition sites and a BamHI sticky end. The ligation product was, again, a useful intermediate plasmid ("pBR-EPO") including the EPO DNA flanked on both sides by banks of restriction site.

The vector chosen for expression of the EPO DNA in COS-1 cells ("pDSVL1") had previously been constructed to allow for selection and autonomous replication in *E. coli*. These characteristics are provided by the origin of replication and Ampicillin resistance gene DNA sequences present in the region spanning nucleotides 2448 through 4362 of pBR322. This sequence was structurally modified by the addition of a linker providing a HindIII recognition immediately adjacent nucleotide 2448 prior to incorporation into the vector. Among the selected vector's other useful properties was the capacity to autonomously replicate in COS-1 cells and the presence of a viral promoter sequence functional in mammalian cells. These characteristics are provided by the origin of replication DNA sequence and "late gene" viral promoter DNA sequence present in the 342 bp sequence spanning nucleotide numbers 5171 through 270 of the SV40 genome. A unique restriction site (BamHI) was provided in the vector and immediately adjacent the viral promoter sequence through use of a commercially available linker sequence (Collaborative Research). Also incorporated in the vector was a 237 base pair sequence (derived as nucleotide numbers 2553 through 2770 of SV40) containing the "late gene" viral mRNA polyadenylation signal (commonly referred to as a transcription terminator). This fragment was positioned in the vector in the proper orientation vis-a-vis the "late gene" viral promoter via the unique BamHI site. Also present in the vector was another mammalian gene at a location not material to potential transcription of a gene inserted at the unique BamHI site, between the viral promoter and terminator sequences. [The mammalian gene comprised an approximately 2,500 bp mouse dihydrofolate reductase (DHFR) minigene isolated from plasmid pMG-1 as in Gasser, et al., *P.N.A.S.* (*U.S.A.*), 79, pp. 6522–6526, (1982).] Again, the major operative components of plasmid pDSVL1 comprise nucleotides 2448 through 4362 of pBR322 along with nucleotides 5171 through 270 (342 bp) and 2553 through 2770 (237 bp) of SV40 DNA.

Figure 2:
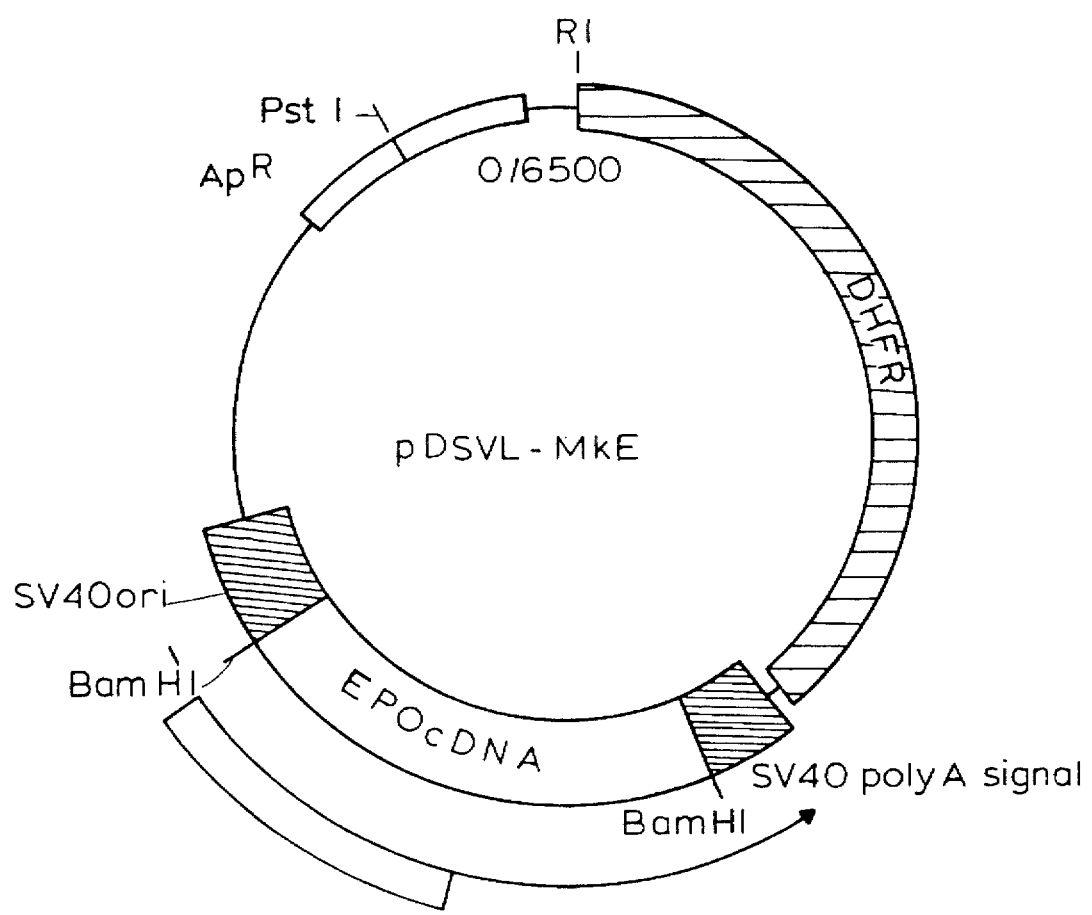
FIG. 2 shows vector pDSVL-MkE.

Following procedures described, e.g., in Maniatis, et al., supra, the EPO-encoding DNA was isolated from plasmid pBR-EPO as a BamHI fragment and ligated into plasmid pDSVL1 cut with BamHI. Restriction enzyme analysis was employed to confirm insertion of the EPO gene in the correct orientation in two of the resulting cloned vectors (duplicate vectors H and L). See FIG. 2, illustrating plasmid pDSVL-MkE. Vectors with EPO genes in the wrong orientation (vectors F, X and G) were saved for use as negative controls in transfection experiments designed to determine EPO expression levels in hosts transformed with vectors having EPO DNA in the correct orientation.

Vectors H, L, F, X and G were combined with carrier DNA (mouse liver and spleen DNA) were employed to transfect duplicate 60 mm plates by calcium phosphate microprecipitate methods. Duplicate 60 mm plates were also transfected with carrier DNA as a "mock" transformation negative control. After five days all culture media were tested for the presence of polypeptides possessing the immunological properties of naturally-occurring EPO.

EXAMPLE 7

A. Initial EPO Expression System Involving COS-1 Cells

The system selected for initial attempts at microbial synthesis of isolatable quantities of human EPO polypeptide material coded for by the human genomic DNA EPO clone, also involved expression in mammalian host cells (i.e., COS-1 cells, A.T.C.C. No. CRL-1650). The human EPO gene was first sub-cloned into a "shuttle" vector which is capable of autonomous replication in both $E.\ coli$ hosts (by virtue of the presence of pBR322 derived DNA) and in the mammalian cell line COS-1 (by virtue of the presence of SV40 virus derived DNA). The shuttle vector, containing the EPO gene, was then transfected into COS-1 cells. EPO polypeptide material was produced in the transfected cells and secreted into the cell culture media.

More specifically, an expression vector was constructed according to the following procedures. DNA isolated from lambda clone λhE1, containing the human genomic EPO gene, was digested with BamHI and HindIII restriction endonucleases, and a 5.6 Kb DNA fragment known to contain the entire EPO gene was isolated. This fragment was mixed and ligated with the bacterial plasmid pUC8 (Bethesda Research Laboratories, Inc.) which had been similarly digested, creating the intermediate plasmid "pUC8-HuE", providing a convenient source of this restriction fragment.

The vector chosen for expression of the EPO DNA in COS-1 cells (pSV4SEt) had previously been constructed. Plasmid pSV4SEt contained DNA sequences allowing selection and autonomous replication in $E.\ coli$. These characteristics are provided by the origin of replication and Ampicillin resistance gene DNA sequences present in the region spanning nucleotides 2448 through 4362 of the bacterial plasmid pBR322. This sequence was structurally modified by the addition of a linker providing a HindIII recognition site immediately adjacent to nucleotide 2448. Plasmid pSV4SEt was also capable of autonomous replication in COS-1 cells. This characteristic was provided by a 342 bp fragment containing the SV40 virus origin of replication (nucleotide numbers 5171 through 270). This fragment had been modified by the addition of a linker providing an EcoRI recognition site adjacent to nucleotide 270 and a linker providing a SalI recognition site adjacent nucleotide 5171. A 1061 bp fragment of SV40 was also present in this vector (nucleotide numbers 1711 through 2772 plus a linker providing a SalI recognition site next to nucleotide number 2772). Within this fragment was an unique BamHI recognition sequence. In summary, plasmid pSV4SEt contained unique BamHI and HindIII recognition sites, allowing insertion of the human EPO gene, sequences allowing replication and selection in $E.\ coli$, and sequences allowing replication in COS-1 cells.

Figure 3:
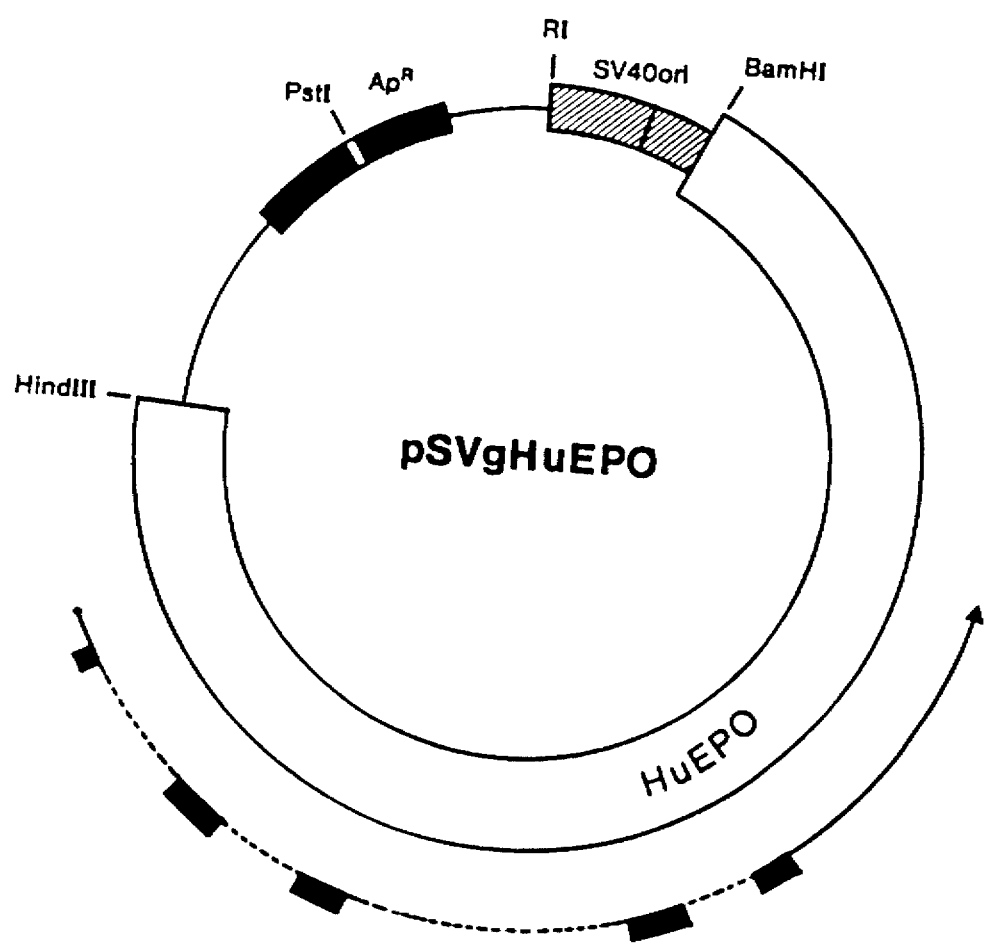
FIG. 3 shows vector pSVgHuEPO.

In order to insert the EPO gene into pSV4SEt, plasmid pUC8-HuE was digested with BamHI and HindIII restriction endonucleases and the 5.6 kb EPO encoding DNA fragment isolated. pSV4SEt was also digested with BamHI and HindIII and the major 2513 bp fragment isolated (preserving all necessary functions). These fragments were mixed and ligated, creating the final vector "pSVgHuEPO". (See, FIG. 3.) This vector was propagated in $E.\ coli$ and vector DNA isolated. Restriction enzyme analysis was employed to confirm insertion of the EPO gene.

Plasmid pSVgHuEPO DNA was used to express human EPO polypeptide material in COS-1 cells. More specifically, pSVgHuEPO DNA was combined with carrier DNA and transfected into triplicate 60 mm plates of COS-1 cells. As a control, carrier DNA alone was also transfected into COS-1 cells. Cell culture media were sampled five and seven days later and tested for the presence of polypeptides possessing the immunological properties of naturally occurring human EPO.

B. Second EPO Expression System Involving COS-1 Cells

Still another system was designed to provide improved production of human EPO polypeptide material coded by the human genomic DNA EPO clone in COS-1 cells (A.T.C.C. No. CRL-1650).

In the immediately preceding system, EPO was expressed in COS-1 cells using its own promoter which is within the 5.6 Kb BamHI to HindIII restriction fragment. In the following construction, the EPO gene is altered so that it is expressed using the SV40 late promoter.

More specifically, the cloned 5.6 Kb BamHI to HindIII genomic human EPO restriction fragment was modified by the following procedures. Plasmid pUC8-HuE, as described above, was cleaved with BamHI and with BstEII restriction endonucleases. BstEII cleaves within the 5.6 Kb EPO gene at a position which is 44 base pairs 5' to the initiating ATG coding for the pre-peptide and approximately 680 base pairs 3' to the HindIII restriction site. The approximately 4900 base pair fragment was isolated. A synthetic linker DNA fragment, containing SalI and BstEII sticky ends and an internal BamHI recognition site was synthesized and purified. The two fragments were mixed and ligated with plasmid pBR322 which had been cut with SalI and BamHI to produce the intermediate plasmid pBRgHE. The genomic human EPO gene can be isolated therefrom as a 4900 base pair BamHI digestion fragment carrying the complete structural gene with a single ATG 44 base pairs 3' to BamHI site adjacent the amino terminal coding region.

Figure 4:
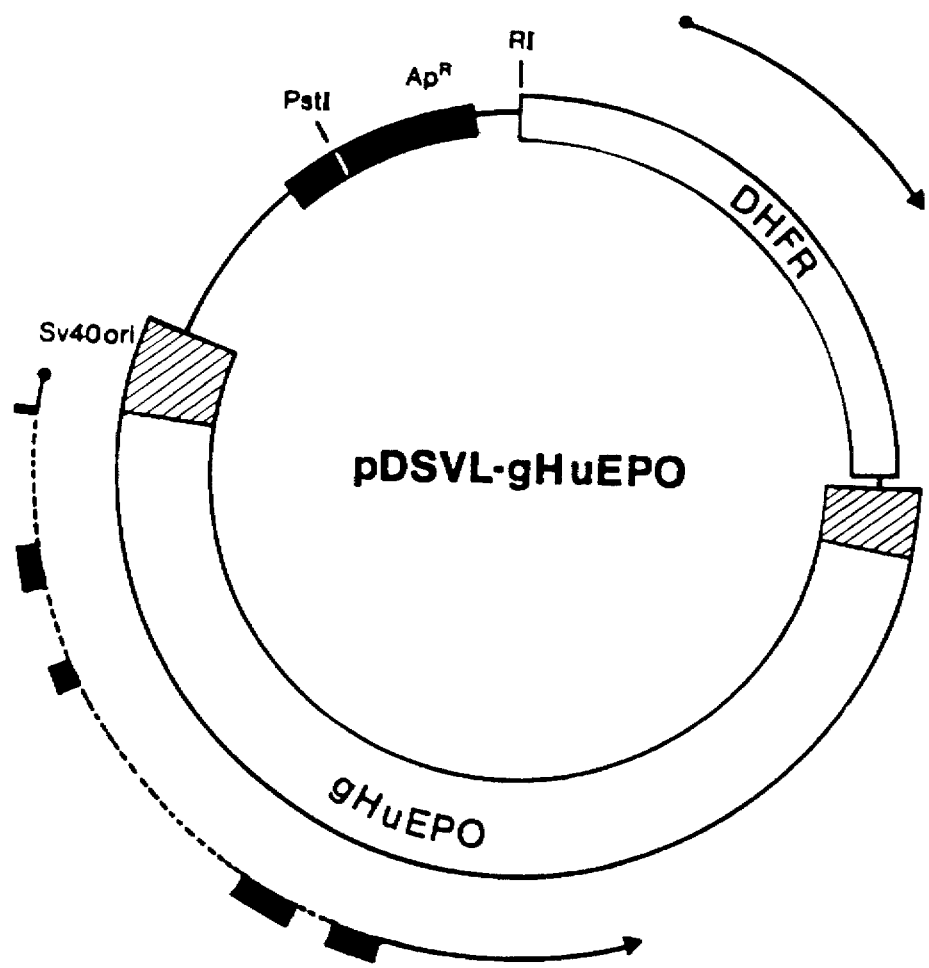
FIG. 4 shows vector pDSVL-gHuEPO.

This fragment was isolated and inserted as a BamHI fragment into BamHI cleaved expression vector plasmid pDSVL1 (described in Example 6). The resulting plasmid, pSVLgHuEPO, as illustrated in FIG. 4, was used to express EPO polypeptide material from COS-1 cells, as described in Examples 6 and 7A.

EXAMPLE 8

Culture media from growth of the six transfected COS-1 cultures of Example 6 were analyzed by radioimmunoassay according to the procedures set forth in Example 2, Part B. Each sample was assayed at 250, 125, 50, and 25 microliter aliquot levels. Supernatants from growth of cells mock transfected or transfected with vectors having incorrect EPO gene orientation were unambiguously negative for EPO immunoreactivity. For each sample of the two supernatants derived from growth of COS-1 cells transfected with vectors (H and L) having the EPO DNA in the correct orientation, the % inhibition of $^{125}$I-EPO binding to antibody ranged from 72 to 88%, which places all values at the top of the standard curve. The exact concentration of EPO in the culture supernatant could not then reliably be estimated. A quite conservative estimate of 300 mU/ml was made, however, from the value calculation of the largest aliquot size (250 microliter).

A representative culture fluid according to Example E and five and seven day culture fluids obtained according to Example 7A were tested in the RIA in order to compare activity of recombinant monkey and human EPO materials to a naturally-occurring human EPO standard and the results are set out in graphic form in FIG. 1. Briefly, the results expectedly revealed that the recombinant monkey EPO significantly competed for anti-human EPO antibody although it was not able to completely inhibit binding under the test conditions. The maximum percent inhibition values for recombinant human EPO, however, closely approximated those of the human EPO standard. The parallel nature of the dose response curves suggests immunological identity of the sequences (epitopes) in common. Prior estimates of monkey EPO in culture fluids were re-evaluated at these higher dilution levels and were found to range from 2.91 to 3.12 U/ml. Estimated human EPO production levels were correspondingly set at 392 mU/ml for the five-day growth sample and 567 mU/ml for the seven day growth sample. Estimated monkey EPO production levels in the Example 7B expression system were on the same order or better.

EXAMPLE 9

Culture fluids prepared according to Examples 6 and 7 were subjected to an in vitro assay for EPO activity according to the procedure of Goldwasser, et al., *Endocrinology*, 97, 2, pp. 315–323 (1975). Estimated monkey EPO values for culture fluids tested ranged from 3.2 to 4.3 U/ml. Human EPO culture fluids were also active in this in vitro assay and, further, this activity could be neutralized by anti-EPO antibody. The recombinant monkey EPO culture fluids according to Example 6 were also subjected to an assay for in vivo biological activity according to the general procedures of Cotes, et al., *Nature*, 191, pp. 1065–1067 (1961) and Hammond, et al., *Ann. N.Y. Acad. Sci.*, 149, pp. 516–527 (1968) and activity levels ranged from 0.94 to 1.24 U/ml.

EXAMPLE 10

In the previous examples, recombinant monkey or human EPO material was produced from vectors used to transfect COS-1 cells. These vectors replicate in COS-1 cells due to the presence of SV40 T antigen within the cell and an SV40 origin of replication on the vectors. Though these vectors produce useful quantities of EPO in COS-1 cells, expression is only transient (7 to 14 days) due to the eventual loss of the vector. Additionally, only a small percentage of COS-1 became productively transfected with the vectors. The present example describes expression systems employing Chinese hamster ovary (CHO) DHFR⁻ cells and the selectable marker, DHFR. [For discussion of related expression systems, see U.S. Pat. No. 4,399,216 and European Patent Applications 117058, 117059 and 117060, all published Aug. 29, 1984.]

CHO DHFR⁻ cells (DuX-B11) CHO K1 cells, Urlaub, et al., *Proc. Nat. Acad. Sci. (U.S.A.)*, Vol. 77, 4461 (1980) lack the enzyme dihydrofolate reductase (DHFR) due to mutations in the structural genes and therefore require the presence of glycine, hypoxanthine, and thymidine in the culture media. Plasmids pDSVL-MkE (Example 6) or pDSVL-gHuEPO (Example 7B) were transfected along with carrier DNA into CHO DHFR⁻ cells growing in media containing hypoxanthine, thymidine, and glycine in 60 mm culture plates. Plasmid pSVgHuEPO (Example 7A) was mixed with the plasmid pMG2 containing a mouse dihydrofolate reductase gene cloned into the bacterial plasmid vector pBR322 (per Gasser, et al., supra.) The plasmid mixture and carrier DNA was transfected into CHO DHFR⁻ cells. (Cells which acquire one plasmid will generally also acquire a second plasmid). After three days, the cells were dispersed by trypsinization into several 100 mm culture plates in media lacking hypoxanthine and thymidine. Only those cells which have been stably transformed with the DHFR gene, and thereby the EPO gene, survive in this media. After 7–21 days, colonies of surviving cells became apparent. These transformant colonies, after dispersion by trypsinization can be continuously propagated in media lacking hypoxanthine and thymidine, creating new cell strains (e.g., CHO pDSVL-MkEPO, CHO pSVgHuEPO, CHO-pDSVL-gHuEPO).

Culture fluids from the above cell strains were tested in the RIA for the presence of recombinant monkey or human EPO. Media for strain CHO pDSVL-MkEPO contained EPO with immunological properties like that obtained from COS-1 cells transfected with plasmid pDSVL-MkEPO. A representative 65 hour culture fluid contained monkey EPO at 0.60 U/ml.

Culture fluids from CHO pSVgHuEPO and CHO pDSVL-gHuEPO contained recombinant human EPO with immunological properties like that obtained with COS-1 cells transfected with plasmid pSVgHuEPO or pDSVL-gHuEPO. A representative 3 day culture fluid from CHO pSVgHuEPO contained 2.99 U/ml of human EPO and a 5.5 day sample from CHO pDSVL-gHuEPO had 18.2 U/ml of human EPO as measured by the RIA.

The quantity of EPO produced by the cell strains described above can be increased by gene amplification giving new cell strains of greater productivity. The enzyme dihydrofolate reductase (DHFR) which is the product coded for by the DHFR gene can be inhibited by the drug methotrexate (MTX). More specifically, cells propagated in media lacking hypoxanthine and thymidine are inhibited or killed by MTX. Under the appropriate conditions, (e.g., minimal concentrations of MTX) cells resistant to and able to grow in MTX can be obtained. These cells are found to be resistent to MTX due to an amplification of the number of their DHFR genes, resulting in increased production of DHFR enzyme. The surviving cells can, in turn, be treated with increasing concentrations of MTX, resulting in cell strains containing greater numbers of DHFR genes. "Passenger genes" (e.g., EPO) carried on the expression vector along with the DHFR gene or transformed with the DHFR gene are frequently found also to be increased in their gene copy number.

As examples of practice of this amplification system, cell strain CHO pDSVL-MkE was subjected to increasing MTX concentrations (0 nM, 30 nM and 100 nM). Representative 65-hour culture media samples from each amplification step were assayed by RIA and determined to contain 0.60, 2.45 and 6.10 U/ml, respectively. Cell strain CHO pDSVL-gHuEPO was subjected to a series of increasing MTX concentrations of 30 nM, 50 nM, 100 nM, 200 nM, 1 μμM, and 5 μM MTX. A representative 3-day culture media sample from the 100 nM MTX step contained human EPO at 3089±129 u/ml as judged by RIA. Representative 48 hour cultural medium samples from the 100 nM and 1 μM MTX steps contained, respectively, human EPO at 466 and 1352 U/ml as judged by RIA (average of triplicate assays). In these procedures, $1\times10^6$ cells were plated in 5 ml of media in 60 mm culture dishes. Twenty-four hours later the media were removed and replaced with 5 ml of serum-free media (high glucose DMEM supplemented with 0.1 mM non-essential amino acids and L-glutamine). EPO was allowed to accumulate for 48 hours in the serum-free media. The media was collected for assay and the cells were trypsinized and counted. The average RIA values of 467 U/ml and 1352 U/ml for cells grown at 100 nM and 1 μM MTX, respectively, provided actual yields of 2335 U/plate and 6750 U/plate. The average cell numbers per plate were $1.94\times10^6$ and $312\times10^6$ cells, respectively. The effective production rates for these culture conditions were thus 1264 and 2167 $U/10^6$ cells/48 hours.

The cells in the cultures described immediately above are a genetically heterogeneous population. Standard screening procedures are being employed in an attempt to isolate genetically homogeneous clones with the highest production capacity. See, Section A, Part 2, of "Points to Consider in the Characterization of Cell Lines Used to Produce Biologics", Jun. 1, 1984, Office of Biologics Research Review, Center for Drugs and Biologics, U.S. Food and Drug Administration.

The productivity of the EPO producing CHO cell lines described above can be improved by appropriate cell culture techniques. The propagation of mammalian cells in culture generally requires the presence of serum in the growth media. A method for production of erythropoietin from CHO cells in media that does not contain serum greatly facilitates the purification of erythropoietin from the culture medium. The method described below is capable of economically producing erythropoietin in serum-free media in large quantities sufficient for production.

Strain CHO pDSVL-gHuEPO cells, grown in standard cell culture conditions, are used to seed spinner cell culture flasks. The cells are propagated as a suspension cell line in the spinner cell culture flask in media consisting of a 50-50 mixture of high glucose DMEM and Ham's F12 supplemented with 5% fetal calf serum, L-glutamine, Penicillin and Streptomycin, 0.05 mM non-essential amino acids and the appropriate concentration of methotrexate. Suspension cell culture allows the EPO-producing CHO cells to be expanded easily to large volumes. CHO cells, grown in suspension, are used to seed roller bottles at an initial seeding density of $1.5\times10^7$ viable cells per 850 cm$^2$ roller bottle in 200 ml of media. The cells are allowed to grow to confluency as an adherent cell line over a three-day period. The media used for this phase of the growth is the same as used for growth in suspension. At the end of the three-day growth period, the serum containing media is removed and replaced with 100 ml of serum-free media; 50-50 mixture of high glucose DMEM and Ham's F12 supplemented with 0.05 mM non-essential amino acids and L-glutamine. The roller bottles are returned to the roller bottle incubator for a period of 1–3 hours and the media again is removed and replaced with 100 ml of fresh serum-free media. The 1–3 hour incubation of the serum-free media reduces the concentration of contaminating serum proteins. The roller bottles are returned to the incubator for seven days during which erythropoietin accumulates in the serum-free culture media. At the end of the seven-day production phase, the conditioned media is removed and replaced with fresh serum-free medium for a second production cycle. As an example of the practice of this production system, a representative seven-day, serum-free media sample contained human erythropoietin at 3892±409 U/ml as judged by the RIA. Based on an estimated cell density of 0.9 to $1.8\times10^5$ cells/cm$^2$, each 850 cm$^2$ roller bottle contained from 0.75 to $1.5\times10^8$ cells and thus the rate of production of EPO in the 7-day, 100 ml culture was 750 to 1470 $U/10^6$ cells/48 hours.

Culture fluids from cell strain CHO pDSVL-MkEPO carried in 10 nM MTX were subjected to RIA in vitro and in vivo EPO activity assays. The conditioned media sample contained 41.2±1.4 U/ml of MkEPO as measured by the RIA, 41.2±0.064 U/ml as measured by the in vitro biological activity assay and 42.5±5 U/ml as measured by the in vivo biological activity assay. Amino acid sequencing of polypeptide products revealed the presence of EPO products, a principle species having 3 residues of the "leader" sequence adjacent the putative amino terminal alanine. Whether this is the result of incorrect membrane processing of the polypeptide in CHO cells or reflects a difference in structure of the am±no terminus of monkey EPO vis-a-vis human EPO, is presently unknown.

Culture fluids from cell strain CHO pDSVL-gHuEPO were subjected to the three assays. A 5.5 day sample contained recombinant human EPO in the media at a level of 18.2 U/ml by RIA assay, 15.8±4.6 U/ml by in vitro assay and 16.8±3.0 U/ml by in vivo assay.

Culture fluid from CHO pDSVL-gHuEPO cells prepared amplified by stepwise 100 nM MTX were subjected to the three assays. A 3.0 day sample contained recombinant human EPO at a level of 3089±129 U/ml by RIA, 2589±71.5 U/ml by in vitro assay, and 2040±160 U/ml by in vivo assay. Amino acid sequencing of this product reveals an amino terminal corresponding to that designated in FIG. 6.

Cell conditioned media from CHO cells-transfected with plasmid pDSVL-MkE in 10 nM MTX were pooled, and the MTX dialyzed out over several days, resulting in media with an EPO activity of 221±5.1 U/ml (EPO-CCM). To determine the in vivo effect of the EPO-CCM upon hematocrit levels in normal Balb/C mice, the following experiment was conducted. Cell conditioned media from untransfected CHO cells (CCM) and EPO-CCM were adjusted with PBS. CCM was used for the control group (3 mice) and two dose levels of EPO-CCM—4 units per injection and 44 units per injection—were employed for the experimental groups (2 mice/group). Over the course of 5 weeks, the seven mice were injected intraperitoneally, times per week. After the eighth injection, average hematocrit values for the control group were determined to be 50.4%; for the 4U group, 55.1%; and, for the 44U group, 67.9%.

Mammalian cell expression products may be readily recovered in substantially purified form from culture media using HPLC (C$_4$) employing an ethanol gradient, preferably at pH 7.

A preliminary attempt was made to characterize recombinant glycoprotein products from conditioned medium of COS-1 and CHO cell expression of the human EPO gene in comparison to human urinary EPO isolates using both Western blot analysis and SDS-PAGE. These studies indicated that the CHO-produced EPO material had a somewhat higher molecular weight than the COS-1 expression product which, in turn, was slightly larger than the pooled source human urinary extract. All products were somewhat heterogeneous. Neuraminidase enzyme treatment to remove sialic acid resulted in COS-1 and CHO recombinant products of approximately equal molecular weight which were both nonetheless larger than the resulting asialo human urinary extract. Endoglycosidase F enzyme (EC 3.2.1) treatment of the recombinant CHO product and the urinary extract product (to totally remove carbohydrate from both) resulted in substantially homogeneous products having essentially identical molecular weight characteristics.

Purified human urinary EPO and a recombinant, CHO cell-produced, EPO according to the invention were subjected to carbohydrate analysis according to the procedure of Ledeen, et al. *Methods in Enzymology*, 83(Part D), 139–191 (1982) as modified through use of the hydrolysis procedures of Nesser, et al., *Anal. Biochem.*, 142, 58–67 (1984). Experimentally determined carbohydrate constitution values (expressed as molar ratios of carbohydrate in the product) for the urinary isolate were as follows: Hexoses, 1.73; N-acetylglucosamine, 1; N-acetylneuraminic acid, 0.93; Fucose, 0; and N-acetylgalactosamine, 0. Corresponding values for the recombinant product (derived from CHO pDSVL-gHuEPO 3-day culture media at 100 nM MTX) were as follows: Hexoses, 15.09; N-acetylglucosamine, 1; N-acetylneuraminic acid, 0.998; Fucose, 0; and N-acetylgalactosamine, 0. These findings are consistent with the Western blot and SDS-PAGE analysis described above.

Glycoprotein products provided by the present invention are thus comprehensive of products having a primary structural conformation sufficiently duplicative of that of a naturally-occurring erythropoietin to allow possession of one or more of the biological properties thereof and having an average carbohydrate composition which differs from that of naturally-occurring erythropoietin.

EXAMPLE 11

The present example relates to the total manufacture by assembly of nucleotide bases of two structural genes encoding the human species EPO sequence of FIG. 6 and incorporating, respectively "preferred" codons for expression in *E. coli* and yeast (*S. cerevisiae*) cells. Also described is the construction of genes encoding analogs of human EPO. Briefly stated, the protocol employed was generally as set out in the previously noted disclosure of Alton, et al. (WO 83/04053). The genes were designed for initial assembly of component oligonucleotides into multiple duplexes which, in turn, were assembled into three discrete sections. These sections were designed for ready amplification and, upon removal from the amplification system, could be assembled sequentially or through a multiple fragment ligation in a suitable expression vector.

FIGS. 10 through 15 and 17 illustrate the design and assembly of a manufactured gene encoding a human EPO translation product lacking any leader or presequence but including an initial methionine residue at position −1. Moreover, the gene incorporated in substantial part *E. coli* preference codons and the construction was therefore referred to as the "ECEPO" gene.

More particularly, FIG. 10 illustrates oligonucleotides employed to generate the Section 1 of the ECEPO gene encoding amino terminal residues of the human species polypeptide. Oligonucleotides were assembled into duplexes (1 and 2, 3 and 4, etc.) and the duplexes were then ligated to provide ECEPO Section 1 as in FIG. 11. Note that the assembled section includes respective terminal EcoRI and BamHI sticky ends, that "downstream" of the EcoRI sticky end is a XbaI restriction enzyme recognition site; and that "upstream" of the BamHI sticky end is a KpnI recognition site. Section 1 could be readily amplified using the M13 phage vector employed for verification of sequence of the section. Some difficulties were encountered in isolating the section as an XbaI/KpnI fragment from RF DNA generated in *E. coli*, likely due to methylation of the KpnI recognition site bases within the host. Single-stranded phage DNA was therefore isolated and rendered into double-stranded form in vitro by primer extension and the desired double-stranded fragment was thereafter readily isolated.

ECEPO gene Sections 2 and 3 (FIGS. 13 and 15) were constructed in a similar manner from the oligonucleotides of FIGS. 12 and 14, respectively. Each section was amplified in the M13 vector employed for sequence verification and was isolated from phage DNA. As is apparent from FIG. 13, XI, ECEPO Section 2 was constructed with EcoRI and BamHI sticky ends and could be isolated as a KpnI/BglII fragment. Similarly, ECEPO Section 3 was prepared with BamHI and SalI sticky ends and could be isolated from phage RF DNA as a BglII/SalI fragment. The three sections thus prepared can readily be assembled into a continuous DNA sequence (FIG. 7) encoding the entire human species EPO polypeptide with an amino terminal methionine codon (ATG) for *E. coli* translation initiation. Note also that "upstream" of the initial ATG is a series of base pairs substantially duplicating the ribosome binding site sequence of the highly expressed OMP-f gene of *E. coli*.

Any suitable expression vector may be employed to carry the ECEPO. The particular vector chosen for expression of the ECEPO gene as the "temperature sensitive" plasmid pCFM536—a derivative of plasmid pCFM414 (A.T.C.C. 40076)—as described in co-pending U.S. patent application Ser. No. 636,727, filed Aug. 6, 1984 (Published EPO Application No. 136,490), by Charles F. Morris. More specifically, pCFM536 was digested with XbaI and HindIII; the large fragment was isolated and employed in a two-part ligation with the ECEPO gene. Sections 1 (XbaI/KpnI), 2 (KpnI/BglII) and 3 (BglII/SalI) had previously been assembled in the correct order in M13 and the EPO gene was isolated therefrom as a single XbaI/HindIII fragment. This fragment included a portion of the polylinker from M13 mp9 phage spanning the SalI to HindIII sites therein. Control of expression in the resulting expression plasmid, p536, was by means of a lambda $P_L$ promoter, which itself may be under control of the $C_{I857}$ repressor gene (such as provided in *E. coli* strain K12ΔHtrp).

The manufactured ECEPO gene above may be variously modified to encode erythropoietin analogs such as [Asn$^2$, des Pro$^2$ through Ile$^6$]hEPO and [His$^7$]hEPO, as described below.

A. [Asn$^2$, des Pro$^2$ through Ile$^6$]hEPO

Plasmid 536 carrying the ECEPO manufactured gene of FIG. 7 as a XbaI to HindIII insert was digested with HindIII and XhoI. The latter endonuclease cuts the ECEPO gene at a unique, 6 base pair recognition site spanning the last base of the codon encoding Asp$^8$ through the second base of the Arg$^{10}$ codon. A XbaI/XhoI "linker" sequence was manufactured having the following sequence:

| XbaI | +1 | 2 | 7 | 8 | 9 |
|---|---|---|---|---|---|
| | Met | Ala | Asn | Cys | Asp | XhoI |
| 5'-CTAG ATG | GCT | AAT | TGC | GAC-3' | |
| 3'-TAC | CGA | TTA | ACG | CTG | AGCT-5' |

The XbaI/XhoI linker and the XhoI/HindIII ECEPO gene sequence fragment were inserted into the large fragment resulting from XbaI and HindIII digestion of plasmid pCFM526—a derivative of plasmid pCFM414 (A.T.C.C. 40076)—as described in co-pending U.S. patent application Ser. No. 636,727, filed Aug. 6, 1984, by Charles F. Morris, to generate a plasmid-borne DNA sequence encoding *E. coli* expression of the Met$^{-1}$ form of the desired analog.

B. [His$^7$]hEPO

Plasmid 536 was digested with HindIII and XhoI as in part A above. A XbaI/XhoI linker was manufactured having the following sequence:

```
XbaI        +1  2   3   4   5   6   7   8   9 XhoI
         Met Ala Pro Pro Arg Leu Ile His Asp
5'-CTAG ATG GCT CCG CCA CGT CTG ATC CAT GAC-3'
   3'-TAC CGAGGC GGT GCA GAC TAG GTA CTG AGCT-5'
```

The linker and the XhoI/HindIII ECEPO sequence fragment were then inserted into pCFM526 to generate a plasmid-borne DNA sequence encoding *E. coli* expression of the Met$^{-1}$ form of the desired analog.

Construction of a manufactured gene ("SCEPO") incorporating yeast preference codons is as described in the following FIGS. 16 through 21 and 8. As was the case with the ECEPO gene, the entire construction involved formation of three sets of oligonucleotides (FIGS. 16, 18 and 20) which were formed into duplexes and assembled into sections (FIGS. 17, 19 and 21). Note that synthesis was facilitated in part by use of some sub-optimal codons in both the SCEPO and ECEPO constructions, i.e., oligonucleotides 7–12 of Section 1 of both genes were identical, as were oligonucleotides 1–6 of Section 2 in each gene.

The assembled SCEPO sections were sequenced in M13 and Sections 1, 2 and 3 were isolatable from the phage as HindIII/KpnI, KpnI/BglII, and BglII/SalI fragments.

The presently preferred expression system for SCEPO gene products is a secretion system based on *S. cerevisiae* α-factor secretion, as described in co-pending U.S. patent application Ser. No. 487,753, filed Apr. 22, 1983, by Grant A. Bitter, published Oct. 1984 as European Patent Application 0 123,294. Briefly put, the system involves constructions wherein DNA encoding the leader sequence of the yeast s-factor gene product is positioned immediately 5' to the coding region of the exogenous gene to be expressed. As a result, the gene product translated includes a leader or signal sequence which is "processed off" by an endogenous yeast enzyme in the course of secretion of the remainder of the product. Because the construction makes use of the α-factor translation initiation (ATG) codon, there was no need to provide such a codon at the −1 position of the SCEPO gene. As may be noted from FIG. 8, the alanine (+1) encoding sequence is preceded by a linker sequence allowing for direct insertion into a plasmid including the DNA for the first 80 residues of the s-factor leader following the α-factor promoter. The specific preferred construction for SCEPO gene expression involved a four-part ligation including the above-noted SCEPO section fragments and the large fragment of HindIII/SalI digestion of plasmid pαC3. From the resulting plasmid pαC3/SCEPO, the α-factor promoter and leader sequence and SCEPO gene were isolated by digestion with BamHI and ligated into BamHI digested plasmid pYE to form expression plasmid pYE/SCEPO.

EXAMPLE 12

The present example relates to expression of recombinant products of the manufactured ECEPO and SCEPO genes within the expression systems of Example 11.

In use of the expression system designed for use of *E. coli* host cells, plasmid p536 of Example 11 was transformed into AM7 *E. coli* cells previously transformed with a suitable plasmid, pMW1, harboring a $C_{I857}$ gene. Cultures of cells in LB broth (Ampicillin 50 μg/ml and kanamycin 5 μg/ml, preferably with 10 mM MgSO$_4$) were maintained at 28° C. and upon growth of cells in culture to O.D.$_{600}$=0.1, EPO expression was induced by raising the culture temperature to 42° C. Cells grown to about 40 O.D. provided EPO production (as estimated by gel) of about 5 mg/OD liter.

Cells were harvested, lysed, broken with French Press (10,000 psi) and treated with lysozyme and NP-40 detergent. The pellet resulting from 24,000xg centrifugation was solubilized with guanidine HCl and subjected to further purification in a single step by means of C$_4$ (Vydac) Reverse Phase HPLC (EtOH, 0–80%, 50 mM NH$_4$Ac, pH 4.5). Protein sequencing revealed the product to be greater than 95% pure and the products obtained revealed two different amino terminals, A-P-P-R . . . and P-P-R . . . in a relative quantitative ratio of about 3 to 1. This latter observation of hEPO and [des Ala$^1$]hEPO products indicates that amino terminal "processing" within the host cells serves to remove the terminal methionine and in some instances the initial alanine. Radioimmunoassay activity for the isolates was at a level of 150,000 to 160,000 U/mg; in vitro assay activity was at a level of 30,000 to 62,000 U/mg; and in vivo assay activity ranged from about 120 to 720 U/mg. (Cf., human urinary isolate standard of 70,000 U/mg in each assay.) The dose response curve for the recombinant product in the in vivo assay differed markedly from that of the human urinary EPO standard.

The EPO analog plasmids formed in parts A and B of Example 11 were each transformed into pMW1-transformed AM7 *E. coli* cells and the cells were cultured as above. Purified isolates were tested in both RIA and in vitro assays. RIA and in vitro assay values for [Asn$^2$, des-Pro$^2$ through Ile$^6$]hEPO expression products were approximately 11,000 U/mg and 6,000 U/mg protein, respectively, while the assay values for [His$^7$]hEPO were about 41,000 U/mg and 14,000 U/mg protein, respectively, indicating that the analog products were from one-fourth to one-tenth as "active" as the "parent" expression product in the assays.

In the expression system designed for use of *S. cerevisiae* host cells, plasmid pYE/SCEPO was transformed into two different strains, YSDP4 (genotype α pep4-3 trp1) and RK81 (genotype αα pep4-3 trp1). Transformed YSDP4 hosts were grown in SD medium (Methods in Yeast Genetics, Cold Spring Harbor Laboratory, Cold Spring Harbor, N.Y., p. 62 (1983) supplemented with casamino acids at 0.5%, pH 6.5 at 30° C. Media harvested when the cells had been grown to 36 O.D. contained EPO products at levels of about 244 U/ml (97 μg/OD liter by RIA). Transformed RK81 cells grown to either 6.5 O.D. or 60 O.D. provided media with EPO concentrations of about 80–90 U/ml (34 μg/OD liter by RIA). Preliminary analyses reveal significant heterogeneity in products produced by the expression system, likely to be due to variations in glycosylation of proteins expressed, and relatively high mannose content of the associated carbohydrate.

Plasmids PαC3 and pYE in HB101 *E. coli* cells were deposited in accordance with the Rules of Practice of the U.S. Patent Office on Sep. 27, 1984, with the American Type Culture Collection, 12301 Parklawn Drive, Rockville, Md., under deposit numbers A.T.C.C. 39881 and A.T.C.C. 39882, respectively. Plasmids pCFM526 in AM7 cells, pCFM536 in JM103 cells, and pMW1 in JM103 cells were likewise deposited on Nov. 21, 1984 as A.T.C.C. 39932, 39934, and 39933, respectively. *Saccharomyces cerevisiae* strains YSPD4 and RK81 were deposited on Nov. 21, 1984 as A.T.C.C. 20734 and 20733, respectively.

It should be readily apparent from consideration of the above illustrative examples that numerous exceptionally valuable products and processes are provided by the present invention in its many aspects.

Polypeptides provided by the invention are conspicuously useful materials, whether they are microbially expressed products or synthetic products, the primary, secondary or tertiary structural conformation of which was first made known by the present invention.

As previously indicated, recombinant-produced and synthetic products of the invention share, to varying degrees, the in vitro biological activity of EPO isolates from natural sources and consequently are projected to have utility as substitutes for EPO isolates in culture media employed for growth of erythropoietic cells in culture. Similarly, to the extent that polypeptide products of the invention share the in vivo activity of natural EPO isolates they are conspicuously suitable for use in erythropoietin therapy procedures practiced on mammals, including humans, to develop any or all of the effects heretofore attributed in vivo to EPO, e.g., stimulation of reticulocyte response, development of ferrokinetic effects (such as plasma iron turnover effects and marrow transit time effects), erythrocyte mass changes, stimulation of hemoglobin C synthesis (see, Eschbach, et al., supra) and, as indicated in Example 10, increasing hematocrit levels in mammals. Included within the class of humans treatable with products of the invention are patients generally requiring blood transfusions and including trauma victims, surgical patients, renal disease patients including dialysis patients, and patients with a variety of blood composition affecting disorders, such as hemophilia, sickle cell disease, physiologic anemias, and the like. The minimization of the need for transfusion therapy through use of EPO therapy can be expected to result in reduced transmission of infectious agents. Products of the invention, by virtue of their production by recombinant methods, are expected to be free of pyrogens, natural inhibitory substances, and the like, and are thus likely to provide enhanced overall effectiveness in therapeutic processes vis-a-vis naturally derived products. Erythropoietin therapy with products of the present invention is also expected to be useful in the enhancement of oxygen carrying capacity of individuals encountering hypoxic environmental conditions and possibly in providing beneficial cardiovascular effects.

A preferred method for administration of polypeptide products of the invention is by parenteral (e.g., IV, IM, SC, or IP) routes and the compositions administered would ordinarily include therapeutically effective amounts of product in combination with acceptable diluents, carriers and/or adjuvants. Preliminary pharmacokinetic studies indicate a longer half-life in vivo for monkey EPO products when administered IM rather than IV. Effective dosages are expected to vary substantially depending upon the condition treated but therapeutic doses are presently expected to be in the range of 0.1 (~7U) to 100 (~7000U) μg/kg body weight of the active material. Standard diluents such as human serum albumin are contemplated for pharmaceutical compositions of the invention, as are standard carriers such as saline.

Adjuvant materials suitable for use in compositions of the invention include compounds independently noted for erythropoietic stimulatory effects, such as testosterones, progenitor cell stimulators, insulin-like growth factor, prostaglandins, serotonin, cyclic AMP, prolactin and triiodothyronine, as well as agents generally employed in treatment of aplastic anemia, such as methenolene, stanozolol and nandrolone [see, e.g., Resegotti, et al., *Panminerva Medica.*, 23, 243–248 (1981); McGonigle, et al., *Kidney Int.*, 25(2), 437–444 (1984); Pavlovic-Kantera, et al., *Expt. Hematol.*, 8(*Supp.* 8), 283–291 (1980); and Kurtz, *FEBS Letters*, 14a(1), 105–108 (1982)]. Also contemplated as adjuvants are substances reported to enhance the effects of, or synergize, erythropoietin or asialo-EPO, such as the adrenergic agonists, thyroid hormones, androgens and BPA [see, Dunn, "Current Concepts in Erythropoiesis", John Wiley and Sons (Chichester, England, 1983); Weiland, et al., *Blut*, 44(3), 173–175 (1982); Kalmanti, *Kidney Int.*, 22, 383–391 (1982); Shahidi, *New. Eng. J. Med.*, 289, 72–80 (1973); Fisher, et al., *Steroids*, 30(6), 833–845 (1977); Urabe, et al., *J. Exp. Med.*, 149, 1314–1325 (1979); and Billat, et al., *Expt. Hematol.*, 10(1), 133–140 (1982)] as well as the classes of compounds designated "hepatic erythropoietic factors" [see, Naughton, et al., *Acta. Haemat.*, 69, 171–179 (1983)] and "erythrotropins" [as described by Congote, et al. in Abstract 364, Proceedings 7th International Congress of Endocrinology (Quebec City, Quebec, Jul. 1–7, 1984); Congote, *Biochem. Biophys. Res. Comm.*, 115(2), 447–483 (1983) and Congote, *Anal. Biochem.*, 140, 428–433 (1984)] and "erythrogenins" [as described in Rothman, et al., *J. Surg. Oncol.*, 20, 105–108 (1982)]. Preliminary screenings designed to measure erythropoietic responses of ex-hypoxic polycythemic mice pre-treated with either 5-α-dihydrotestosterone or nandrolone and then given erythropoietin of the present invention have generated equivocal results.

Diagnostic uses of polypeptides of the invention are similarly extensive and include use in labelled and unlabelled forms in a variety of immunoassay techniques including RIA's, ELISA's and the like, as well as a variety of in vitro and in vivo activity assays. See, e.g., Dunn, et al., *Expt. Hematol.*, 11(7), 590–600 (1983); Gibson, et al., *Pathology*, 16, 155–156 (1984); Krystal, *Expt. Hematol.*, 11(7), 649–660 (1983); Saito, et al., *Jap. J. Med.*, 23(1), 16–21 (1984); Nathan, et al., *New Eng. J. Med.*, 308(9), 520–522 (1983); and various references pertaining to assays referred to therein. Polypeptides of the invention, including synthetic peptides comprising sequences of residues of EPO first revealed herein, also provide highly useful pure materials for generating polyclonal antibodies and "banks" of monoclonal antibodies specific for differing continuous and discontinuous epitopes of EPO. As one example, preliminary analysis of the amino acid sequences of FIG. 6 in the context of hydropathicity according to Hopp, et al., *P.N.A.S. (U.S.A.)*, 78, pp. 3824–3828 (1981) and of secondary structures according to Chou, et al., *Ann. Rev. Biochem.*, 47, p. 251 (1978) revealed that synthetic peptides duplicative of continuous sequences of residues spanning positions 41–57 inclusive, 116–118 inclusive and 144–166 inclusive are likely to produce a highly antigenic response and generate useful monoclonal and polyclonal antibodies immunoreactive with both the synthetic peptide and the entire protein. Such antibodies are expected to be useful in the detection and affinity purification of EPO and EPO-related products.

Illustratively, the following three synthetic peptides were prepared:

(1) hEPO 41–57, V-P-D-T-K-V-N-F-Y-A-W-K-R-M-E-V-G;

(2) hEPO 116–128, K-E-A-I-S-P-P-D-A-A-S-A-A;

(3) hEPO 144–166, V-Y-S-N-F-L-R-G-K-L-K-L-Y-T-G-E-A-C-R-T-G-D-R. Preliminary immunization studies employing the above-noted polypeptides have revealed a relatively weak positive response to hEPO 41–57, no appreciable response to hEPO 116–128, and a strong positive response to hEPO 144–166, as measured by capacity of rabbit serum antibodies to immunoprecipitate $^{125}$I-labelled human urinary EPO isolates. Preliminary in vivo activity studies on the three peptides revealed no significant activity either alone or in combination.

While the deduced sequences of amino acid residues of mammalian EPO provided by the illustrative examples essentially define the primary structural conformation of mature EPO, it will be understood that the specific sequence of 165 amino acid residues of monkey species EPO in FIG. 5 and the 166 residues of human species EPO in FIG. 6 do not limit the scope of useful polypeptides provided by the invention. Comprehended by the present invention are those various naturally-occurring allelic forms of EPO which past research into biologically active mammalian polypeptides such as human γ interferon indicates are likely to exist. (Compare, e.g., the human immune interferon species reported to have an arginine residue at position No. 140 in EPO published application 0 077 670 and the species reported to have glutamine at position No. 140 in Gray, et al., *Nature*, 295, pp. 503–508 (1982). Both species are characterized as constituting "mature" human γ interferon sequences.) Allelic forms of mature EPO polypeptides may vary from each other and from the sequences of FIGS. 5 and FIG. 6 in terms of length of sequence and/or in terms of deletions, substitutions, insertions or additions of amino acids in the sequence, with consequent potential variations in the capacity for glycosylation. As noted previously, one putative allelic form of human species EPO is believed to include a methionine residue at position 126. Expectedly, naturally-occurring allelic forms of EPO-encoding DNA genomic and cDNA sequences are also likely to occur which code for the above-noted types of allelic polypeptides or simply employ differing codons for designation of the same polypeptides as specified.

In addition to naturally-occurring allelic forms of mature EPO, the present invention also embraces other "EPO products" such as polypeptide analogs of EPO and fragments of "mature" EPO. Following the procedures of the above-noted published application by Alton, et al. (WO/83/04053) one may readily design and manufacture genes coding for microbial expression of polypeptides having primary conformations which differ from that herein specified for mature EPO in terms of the identity or location of one or more residues (e.g., substitutions, terminal and intermediate additions and deletions). Alternately, modifications of cDNA and genomic EPO genes may be readily accomplished by well-known site-directed mutagenesis techniques and employed to generate analogs and derivatives of EPO. Such EPO products would share at least one of the biological properties of EPO but may differ in others. As examples, projected EPO products of the invention include those which are foreshortened by e.g., deletions [Ash$^2$, des-Pro$^2$ through Ile$^6$]hEPO, [des-Thr$^{163}$ through Arg$^{166}$]hEPO and "Δ27-55hEPO", the latter having the residues coded for by an entire exon deleted; or which are more stable to hydrolysis (and, therefore, may have more pronounced or longer lasting effects than naturally-occurring EPO); or which have been altered to delete one or more potential sites for glycosylation (which may result in higher activities for yeast-produced products); or which have one or more cystein residues deleted or replaced by, e.g., histidine or serine residues (such as the analog [His$^7$]hEPO) and are potentially more easily isolated in active form from microbial systems; or which have one or more tyrosine residues replaced by phenylalanine (such as the analogs [Phe$^{15}$]hEPO, [Phe$^{49}$]hEPO, and [Phe$^{145}$]hEPO) and may bind more or less readily to EPO receptors on target cells. Also comprehended are polypeptide fragments duplicating only a part of the continuous amino acid sequence or secondary conformations within mature EPO, which fragments may possess one activity of EPO (e.g., receptor binding) and not others (e.g., erythropoietic activity). Especially significant in this regard are those potential fragments of EPO which are elucidated upon consideration of the human genomic DNA sequence of FIG. 6, i.e., "fragments" of the total continuous EPO sequence which are delineated by intron sequences and which may constitute distinct "domains" of biological activity. It is noteworthy that the absence of in vivo activity for any one or more of the "EPO products" of the invention is not wholly preclusive of therapeutic utility (see, Weiland, et al., supra) or of utility in other contexts, such as in EPO assays or EPO antagonism. Antagonists of erythropoietin may be quite useful in treatment of polycythemias or cases of overproduction of EPO [see, e.g., Adamson, *Hosp. Practice*, 18(12), 49–57 (1983), and Hellmann, et al., *Clin. Lab. Haemat.*, 5, 335–342 (1983)].

According to another aspect of the present invention, the cloned DNA sequences described herein which encode human and monkey EPO polypeptides are conspicuously valuable for the information which they provide concerning the amino acid sequence of mammalian erythropoietin which has heretofore been unavailable despite decades of analytical processing of isolates of naturally-occurring products. The DNA sequences are also conspicuously valuable as products useful in effecting the large scale microbial synthesis of erthropoietin by a variety of recombinant techniques. Put another way, DNA sequences provided by the invention are useful in generating new and useful vital and circular plasmid DNA vectors, new and useful transformed and transfected microbial procaryotic and eucaryotic host cells (including bacterial and yeast cells and mammalian cells grown in culture), and new and useful methods for cultured growth of such microbial host cells capable of expression of EPO and EPO products. DNA sequences of the invention are also conspicuously suitable materials for use as labelled probes in isolating EPO and related protein encoding cDNA and genomic DNA sequences of mammalian species other than human and monkey species herein specifically illustrated. The extent to which DNA sequences of the invention will have use in various alternative methods of protein synthesis (e.g., in insect cells) or in genetic therapy in humans and other mammals cannot yet be calculated. DNA sequences of the invention are expected to be useful in developing transgenic mammalian species which may serve as eucaryotic "hosts" for production of erythropoietin and erythropoietin products in quantity. See, generally, Palmiter, et al., *Science*, 222(4625), 809–814 (1983).

Viewed in this light, therefore, the specific disclosures of the illustrative examples are clearly not intended to be limiting upon the scope of the present invention and numerous modifications and variations are expected to occur to those skilled in the art. As one example, while DNA sequences provided by the illustrative examples include cDNA and genomic DNA sequences, because this application provides amino acid sequence information essential to manufacture of DNA sequence, the invention also comprehends such manufactured DNA sequences as may be constructed based on knowledge of EPO amino acid sequences. These may code for EPO (as in Example 12) as well as for EPO fragments and EPO polypeptide analogs (i.e., "EPO Products") which may share one or more biological properties of naturally-occurring EPO but not share others (or possess others to different degrees).

DNA sequences provided by the present invention are thus seen to comprehend all DNA sequences suitable for use in securing expression in a procaryotic or eucaryotic host cell of a polypeptide product having at least a part of the primary structural conformation and one or more of the biological properties of erythropoietin, and selected from among: (a) the DNA sequences set out in FIGS. 5 and 6; (b) DNA sequences which hybridize to the DNA sequences defined in (a) or fragments thereof; and (c) DNA sequences which, but for the degeneracy of the genetic code, would hybridize to the DNA sequences defined in (a) and (b). It is noteworthy in this regard, for example, that existing allelic monkey and human EPO gene sequences and other mammalian species gene sequences are expected to hybridize to the sequences of FIGS. 5 and 6 or to fragments thereof. Further, but for the degeneracy of the genetic code, the SCEPO and ECEPO genes and the manufactured or mutagenized cDNA or genomic DNA sequences encoding various EPO fragments and analogs would also hybridize to the above-mentioned DNA sequences. Such hybridizations could readily be carried out under the hybridization conditions described herein with respect to the initial isolation of the monkey and human EPO-encoding DNA or more stringent conditions, if desired to reduce background hybridization.

In a like manner, while the above examples illustrate the invention of microbial expression of EPO products in the context of mammalian cell expression of DNA inserted in a hybrid vector of bacterial plasmid and viral genomic origins, a wide variety of expression systems are within the contemplation of the invention. Conspicuously comprehended are expression systems involving vectors of homogeneous origins applied to a variety of bacterial, yeast and mammalian cells in culture as well as to expression systems not involving vectors such as calcium phosphate transfection of cells). In this regard, it will be understood that expression of, e.g., monkey origin DNA in monkey host cells in culture and human host cells in culture, actually constitute instances of "exogenous" DNA expression inasmuch as the EPO DNA whose high level expression is sought would not have its origins in the genome of the host. Expression systems of the invention further contemplate these practices resulting in cytoplasmic formation of EPO products and accumulation of glycosylated and non-glycosylated EPO products in host cell cytoplasm or membranes (e.g., accumulation in bacterial periplasmic spaces) or in culture medium supernatants as above illustrated, or in rather uncommon systems such as *P. aeruginosa* expression systems (described in Gray, et al., *Biotechnology*, 2, pp. 161–165 (1984)).

Improved hybridization methodologies of the invention, while illustratively applied above to DNA/DNA hybridization screenings are equally applicable to RNA/RNA and RNA/DNA screening. Mixed probe techniques as herein illustrated generally constitute a number of improvements in hybridization processes allowing for more rapid and reliable polynucleotide isolations. These many individual processing improvements include: improved colony transfer and maintenance procedures; use of nylon-based filters such as Gene-Screen and GeneScreen Plus to allow reprobing with same filters and repeated use of the filter; application of novel protease treatments [compared, e.g., to Taub, et al. *Anal. Biochem.*, 126, pp. 222–230 (1982)]; use of very low individual concentrations (on the order of 0.025 picomole) of a large number of mixed probes (e.g., numbers in excess of 32); and, performing hybridization and post-hybridization steps under stringent temperatures closely approaching (i.e., within 4° C. and preferably within 2° C. away from) the lowest calculated dissociation temperature of any of the mixed probes employed. These improvements combine to provide results which could not be expected to attend their use. This is amply illustrated by the fact that mixed probe procedures involving 4 times the number of probes ever before reported to have been successfully used in even cDNA screens on messenger RNA species of relatively low abundancy were successfully applied to the isolation of a unique sequence gene in a genomic library screening of 1,500,000 phage plaques. This feat was accomplished essentially concurrently with the publication of the considered opinion of Anderson, et al., supra, that mixed probe screening methods were ". . . impractical for isolation of mammalian protein genes when corresponding RNA's are unavailable.

What is claimed is:

1. A process for the preparation of an in vivo biologically active erythropoietin product comprising the steps of:

(a) growing, under suitable nutrient conditions, host cells transformed or transfected with an isolated DNA sequence selected from the group consisting of (1) the DNA sequences set out in FIGS. 5 and 6, (2) the protein coding sequences set out in FIGS. 5 and 6, and (3) DNA sequences which hybridize under stringent conditions to the DNA sequences defined in (1) and (2) or their complementary strands; and (b) isolating said erythropoietin product therefrom.

2. A process for the preparation of an in vivo biologically active erythropoietin product comprising the steps of transforming or transfecting a host cell with an isolated DNA sequence encoding the mature erythropoietin amino acid sequence of FIG. 6 and isolating said erythropoietin product from said host cell or the medium of its growth.

3. The process according to claim 1 or 2 wherein said host cells are mammalian cells.

4. A process for the production of a glycosylated erythropoietin polypeptide having the in vivo biological property of causing bone marrow cells to increase production of reticulocytes and red blood cells comprising the steps of:

a) growing, under suitable nutrient conditions, vertebrate cells comprising promoter DNA, other than human erythropoietin promoter DNA, operatively linked to DNA encoding the mature erythropoietin amino acid sequence of FIG. 6; and b) isolating said glycosylated erythropoietin polypeptide expressed by said cells.

5. The process of claim 4 wherein said promoter DNA is viral promoter DNA.

6. A process for the production of a glycosylated erythropoietin polypeptide having the in vivo biological property of causing bone marrow cells to increase production of reticulocytes and red blood cells comprising the steps of:

a) growing, under suitable nutrient conditions, vertebrate cells comprising amplified DNA encoding the mature erythropoietin amino acid sequence of FIG. 6; and b) isolating said glycosylated erythropoietin polypeptide expressed by said cells.

7. The process of claim 6 wherein said vertebrate cells further comprise amplified marker gene DNA.

8. The process of claim 7 wherein said amplified marker gene DNA is Dihydrofolate reductase (DHFR) gene DNA.

9. The process according to claims 2, 4 and 6 wherein said cells are mammalian cells.

* * * * *

UNITED STATES PATENT AND TRADEMARK OFFICE
CERTIFICATE OF CORRECTION

PATENT NO. : 5,618,698

DATED : April 8, 1997

INVENTOR(S) : Fu-Kuen Lin

Page 1 of 3

It is certified that error appears in the above-indentified patent and that said Letters Patent is hereby corrected as shown below:

In Abstract, page 1, line 15, "end" should be -- and --.

In Other Publicaitons, page 2, column 1, line 10-11, "EMBO J. (7)" should be -- EMBO J., 5(7) --.

In Other Publications, page 3, column 2, line 61, "Ttransported" should be -- Transported --.

In Other Publications, page 4, column 2, line 31, "Blochem" should be -- Biochem --.

In Other Publications, page 7, column 1, line 22, "Melior" should be -- Mellor --.

In Other Publications, page 7, column 2, line 45, "structure of c?-subunit" should be --structure of α-subunit--.

In Other Publications, page 9, column 2, line 54, "Anal. Blochem" should be -- Anal. Biochem --.

In Other Publications, page 10, column 1, line 1, "Tramontario et al." should be -- Tramontano et al --.

In the Figures, Figure 5C, line 18
GTGfGTGGGGAAGCAGGGCGGJAGGGGTGGAGCTGGGATGCGAGfGAGAACCGTGAAGAC should be

GTGTGTGGGGAAGCAGGGCGGTAGGGGTGGAGCTGGGATGCGAGTGAGAACCGTGAAGAC

In the Figures, FIG. 13, line 4, "GTTGGTCAAC" should be -GTTGGTCAAC-
              CAACCACTTG                CAACCAGTTG In the Figures, FIG. 18, line 9, "AAGCTGTTTTGAGAGGTGAAGCCT" should be -
AAGCTGTTTTGAGAGGTCAAGCCT- Column 1, line 63, "sequences The mRNA" should be -- sequences. The mRNA --.

UNITED STATES PATENT AND TRADEMARK OFFICE
CERTIFICATE OF CORRECTION

PATENT NO. : 5,618,698
DATED : April 8, 1997
INVENTOR(S) : Fu-Kuen Lin

It is certified that error appears in the above-indentified patent and that said Letters Patent is hereby corrected as shown below:

Column 2, line 60, "Note frequently" should be -- More frequently --.

Column 4, line 30, "(U.S.A.), pp. 6461-6464" should be -- (U.S.A.), 79, pp. 6461-6464 --.

Column 4, line 64, "of the human" should be -- of human --.

Column 5, line 5, "60, pp. 6838-6842" should be -- 80, pp. 6838-6842 --.

Column 8, line 20, "Blood, 4(2)" should be -- Blood, 64(2) --.

Column 10, line 41, "residue position -1)." should be -- residue (at position -1) --.

Column 11, line 11, "functional vital and circular" should be -- functional viral and circular --.

Column 15, line 12, "Example 6 and 7" should be -- Examples 6 and 7 --.

Column 16, line 65, "added, the tubes" should be -- added, and the tubes --.

Column 17, line 45, "(2) HincII" should be -- (2) HincII --.

Column 21, line 32, "FIG. 9, below" should be -- FIG. 9, --.

Column 23, line 61, "providing a SalI recognition" should be -- providing a SalI recognition --.

UNITED STATES PATENT AND TRADEMARK OFFICE
CERTIFICATE OF CORRECTION

PATENT NO. : 5,618,698
DATED : April 8, 1997
INVENTOR(S) : Fu-Kuen Lin

It is certified that error appears in the above-indentified patent and that said Letters Patent is hereby corrected as shown below:

Column 25, line 10, "Example E" should be -- Example 6 --.

Column 26, line 64, "1μμM" should be -- 1μM --.

Column 27, line 9, "collected for assay" should be -- collected for RIA assay --.

Column 27, line 14, "and 312x10$^6$cells" should be -- 3.12 x 10$^6$ cells --.

Column 28, line 19, "the am+no terminus" should be -- the amino terminus --.

Column 28, line 33, CHO cells-transfected should be -- cells transfected --.

Column 28, line 46, "intraperitoneally, times" should be -- intraperitoneally, 3 times --.

Column 29, line 48, "17 illustrate" should be -- 7 illustrate --.

Column 30, line 11, "FIG. 13, XI" should be -- FIG. 13 --.

Column 31, line 38, "Oct. 1984" should be -- Oct. 31, 1984 --.

Column 31, line 41, "yeast s-factor" should be -- yeast α-factor --.

Column 31, line 52, "the s-factor" should be -- the α-factor --.

Column 34, line 54, "116-118" should be -- 116-128 --.

Column 35, line 4, "resopnse" should be -- response --.

Column 35, line 57, "[Ash$^2$" should be -- [Asn$^2$ --.

Signed and Sealed this

Fourth Day of November, 1997

BRUCE LEHMAN

Attest:

Attesting Officer

Commissioner of Patents and Trademarks